(12) United States Patent
Yaghi et al.

(10) Patent No.: US 8,314,245 B2
(45) Date of Patent: Nov. 20, 2012

(54) PREPARATION OF FUNCTIONALIZED ZEOLITIC FRAMEWORKS

(75) Inventors: Omar M. Yaghi, Los Angeles, CA (US); Hideki Hayashi, Los Angeles, CA (US); Rahul Banerjee, Los Angeles, CA (US); Kyo Sung Park, Los Angeles, CA (US); Bo Wang, Los Angeles, CA (US); Adrien P. Cote, Los Angeles, CA (US)

(73) Assignees: The Regents of the University of Michigan, Ann Arbor, MI (US); The Regents of the University of California, Oakland, CA (US)

( * ) Notice: Subject to any disclaimer, the term of this patent is extended or adjusted under 35 U.S.C. 154(b) by 934 days.

(21) Appl. No.: 11/680,386

(22) Filed: Feb. 28, 2007

(65) Prior Publication Data

US 2007/0202038 A1 Aug. 30, 2007

Related U.S. Application Data

(60) Provisional application No. 60/886,492, filed on Jan. 24, 2007, provisional application No. 60/777,739, filed on Feb. 28, 2006.

(51) Int. Cl.
*C07F 3/06* (2006.01)
*B01J 32/00* (2006.01)
*B01J 20/28* (2006.01)

(52) U.S. Cl. ......... 548/108; 502/400; 502/401; 502/439
(58) Field of Classification Search .................. 548/108; 502/400, 401, 439
See application file for complete search history.

(56) References Cited

U.S. PATENT DOCUMENTS

| | | | |
|---|---|---|---|
| 3,144,418 A | 8/1964 | Hill et al. |
| 4,359,327 A | 11/1982 | Armand et al. |
| 5,629,523 A | 5/1997 | Ngo et al. |
| 5,648,508 A | 7/1997 | Yaghi |
| RE35,908 E | 9/1998 | Kitaguchi et al. |
| 5,862,796 A | 1/1999 | Seki et al. |
| 5,880,471 A | 3/1999 | Schelten et al. |
| 5,940,460 A | 8/1999 | Seidel et al. |
| 6,072,181 A | 6/2000 | Hassard et al. |
| 6,312,902 B1 | 11/2001 | Shultz et al. |
| 6,348,607 B1 | 2/2002 | Müller et al. |
| 6,479,680 B1 | 11/2002 | Bassler et al. |
| 6,479,826 B1 | 11/2002 | Klann et al. |
| 6,518,441 B2 | 2/2003 | Grosch et al. |
| 6,545,281 B1 | 4/2003 | McGregor et al. |
| 6,617,467 B1 | 9/2003 | Mueller et al. |
| 6,624,318 B1 | 9/2003 | Mueller et al. |
| 6,727,371 B2 | 4/2004 | Muller et al. |
| 6,893,564 B2 | 5/2005 | Mueller et al. |
| 6,929,679 B2 | 8/2005 | Muller et al. |
| 6,930,193 B2 | 8/2005 | Yaghi et al. |
| 6,965,026 B2 | 11/2005 | Zaworotko et al. |
| 6,979,544 B2 | 12/2005 | Keen |
| 7,008,607 B2 | 3/2006 | Muller et al. |
| 7,119,219 B2 | 10/2006 | Muller et al. |
| 2003/0078311 A1 | 4/2003 | Muller et al. |
| 2004/0110950 A1 | 6/2004 | Li et al. |
| 2004/0225134 A1 | 11/2004 | Yaghi et al. |
| 2004/0265670 A1 | 12/2004 | Mueller et al. |

FOREIGN PATENT DOCUMENTS

| | | |
|---|---|---|
| CA | 2 387 122 | 2/2001 |
| CA | 2 414 756 | 1/2003 |
| CA | 2 414 779 | 1/2003 |
| DE | 44 08 772 | 9/1994 |
| DE | 197 23 950 | 12/1998 |
| DE | 198 35 907 | 2/2000 |
| DE | 198 47 629 | 4/2000 |
| DE | 199 36 547 | 2/2001 |
| DE | 100 15 246 | 10/2001 |
| DE | 100 32 884 | 1/2002 |
| DE | 100 32 885 | 1/2002 |
| DE | 101 11 230 | 9/2002 |
| DE | 101 43 195 | 3/2003 |
| EP | 0 557 116 | 8/1993 |
| EP | 0 727 608 | 8/1996 |
| EP | 0 790 253 | 8/1997 |
| EP | 1 280 090 A1 | 1/2003 |
| JP | 2004024247 | 1/2004 |
| WO | WO 97/46711 | 12/1997 |
| WO | WO 99/05151 | 2/1999 |
| WO | WO 00/78837 | 12/2000 |
| WO | WO 01/16209 | 3/2001 |
| WO | WO 01/27186 | 4/2001 |
| WO | WO 02/070526 | 9/2002 |
| WO | WO 02/088148 | 11/2002 |

(Continued)

OTHER PUBLICATIONS

Huang et al, "Ligand-directed strategy for zeolite-type metal-organic frameworks:zinc(II) imidazolates with unusual zeolitic topologies", Angew. Checm. Int. Ed. (2006) published online (Jan. 27, 2006).*
Tian et al, "Two polymorphs of Cobalt(II) imidazolate polymers synthesized solvothermally by using one organic template N,N-dimethylacetamide", Inorganic Chemistry, vol. 43, No. 15, 2004, pp. 4631-4635.*
Huang et al, "A new route to supramolecular isomers via molecular templating:nanosized molecular polygons of copper(II) 2-methylimidazolates", J.Am.Chem.Soc. (2004), 126, pp. 13218-13219.*
Tian et al, "[Co5(im)10.2MB]: A metal-organic open-framework with zeolite-like topology", Angew. Chem. Int. Ed., (2002), 41, No. 8, pp. 1384-1386.*
U.S. Appl. No. 10/270,642, filed Oct. 16, 2002, Mueller et al.
U.S. Appl. No. 10/611,863, filed Jul. 3, 2003, Mueller et al.
U.S. Appl. No. 10/983,629, filed Nov. 9, 2004, Hesse et al.
Bondi, A., "van der Waals Volumes and Radii," Journal of Phys. Chem., Mar. 16, 1964, vol. 68, No. 3, pp. 441-451.

(Continued)

*Primary Examiner* — David M Brunsman
(74) *Attorney, Agent, or Firm* — Brooks Kushman P.C.

(57) ABSTRACT

The disclosure provides zeolitic frameworks for gas separation, gas storage, catalysis and sensors. More particularly the disclosure provides zeolitic frameworks (ZIFs). The ZIF of the disclosure comprises any number of transition metals or a homogenous transition metal composition.

25 Claims, 27 Drawing Sheets
(21 of 27 Drawing Sheet(s) Filed in Color)

FOREIGN PATENT DOCUMENTS

| | | |
|---|---|---|
| WO | 02/099822 A2 | 12/2002 |
| WO | WO 03/035717 | 5/2003 |
| WO | WO 03/044228 A1 | 5/2003 |
| WO | 2006/116340 A1 | 11/2006 |
| WO | 2007/131955 A1 | 11/2007 |
| WO | 2009/020745 A9 | 8/2009 |
| WO | 2009/105255 A2 | 8/2009 |
| WO | 2010/012656 A1 | 2/2010 |
| WO | 2010/078337 A1 | 7/2010 |

OTHER PUBLICATIONS

Bennett, J.M. and J.V. Smith, "Positions of Cations and Molecules in Zeolites with the Faujastie-Type Framework I. Dehydrated Ca-Exchanged Faujasite," Mat. Res. Bull., vol. 3, No. 8, 1968, pp. 633-642.
Hoskins, B.F. and R. Robson, "Infinite Polymeric Frameworks Consisting of Three Dimensionally Linked Rod-Like Segments," J. Am. Chem. Soc., 1989, vol. 111, pp. 5962-5964.
Fagan, P.J. and M.D. Ward, "Building Molecular Crystals," Sci. Am., Jul. 1992, pp. 48-54.
Stein, A., S.W. Keller and T.E. Mallouk, "Turning Down the Heat, Design and Mechanism in Solid-State Synthesis," Mar. 12, 1993, vol. 259, pp. 1558-1564.
Russell, V.A., C.C. Evans, W.Li and M.D. Ward, "Nanoporous Molecular Sandwiches: Pillared Two-Dimensional Hydrogen-Bonded Networks with Adjustable Porosity," Science, Apr. 25, 1997, vol. 276, pp. 575-579.
Husing, N. and U. Schubert, "Aerogels-Airy Materials: Chemistry, Structure, and Properties," Agnew. Chem. Int. Ed., 1998, vol. 37, pp. 22-45.
Menon, V.C. and S. Komarneni, "Porous Adsorbents for Vehicular Natural Gas Storage: A Review," J. of Porous Materials, 1998, vol. 5, pp. 43-58.
Jones, C.W., K. Tsuji and M.E. Davis, "Organic-Functionalized Molecular Sieves as Shape-Selective Catalysts," Nature, May 7, 1998, vol. 393, pp. 52-54.
Fujita, M., "Self-Assembly of [2]Catenanes Containing Metals in Their Backbones," Accounts of Chemical Research, 1999, vol. 32, No. 1, pp. 53-61.
Li, H., M. Eddaoudi, M. O'Keeffe and O.M. Yaghi, "Design and Synthesis of an Exceptionally Stable and Highly Porous Metal-Organic Framework," Nature, Nov. 18, 1999, vol. 402, pp. 276-279.
Li, H., C.E. Davis, T.L. Groy, D.G. Kelley and O.M. Yaghi, Coordinately Unsaturated Metal Centers in the Extended Porous Framework of $Zn_3(BDC)_3 \cdot 6CH_3OH$ (BDC = 1,4-Benzenedicarboxylate), J. Am. Chem. Soc., 1998, vol. 120, pp. 2186-1287.
Kiang, Y.-H, G.B. Gardner, S. Lee, Z. Xu and E.B. Lobkovsky, "Variable Pore Size, Variable Chemical Functionality, and an Example of Reactivity Within Porous Phenylacetylene Silver Salts," J. Am. Chem. Soc., 1999, vol. 121, pp. 8204-8215.
Eddaoudi, M., H. Li and O.M. Yaghi, "Highly Porous and Stable Metal-Organic Frameworks: Structure Design and Sorption Properties," J. Am. Chem. Soc., 2000, vol. 122, pp. 1391-1397.
Noro, S., S. Kitagawa, M. Kondo and K. Seki, "A New, Methane Adsorbent, Porous Coordination Polymer, $[\{CuSiF_6(4,4\text{-bipyridine})_2\}_n]$," Angew. Chem. Int. Ed., 2000, vol. 39, No. 12, pp. 2081-2084.
Yaghi, O.M., M. O'Keeffe and M. Kanatzidis, "Design of Solids from Molecular Building Blocks: Golden Opportunities for Solid State Chemistry," J. Solid State Chem., 2000, vol. 152, pp. 1-2.
Reineke, T.M., M. Eddaoudi, D. Moler, M. O'Keeffe and O.M. Yaghi, "Large Free Volume in Maximally Interpenetrating Networks: The Role of Secondary Building Units Exemplified by $Tb_2(ADB)_3$ $[CH_3]_2SO]_416$ [$(CH_3)_2SO]^1$, " J. Am. Chem. Soc., 2000, vol. 122, pp. 4843-4844.
Eddaoudi, M., D.B. Moler, H. Li, B. Chen, T.M. Reineke, M. O'Keeffe and O.M. Yaghi, "Modular Chemistry: Secondary Building Units as a Basis for the Design of Highly Porous and Robust Metal-Organic Carboxylate Frameworks," Acc. Chem. Res., 2001, vol. 34, pp. 319-330.
Seki, K., "Design of an Adsorbent with an Ideal Pore Structure for Methane Adsorption Using Metal Complexes," Chem. Commun., 2001, 1496-1497.
Kim, J., B. Chen, T.M. Reineke, H. Li, M. Eddaoudi, D.B. Moler, M.O 'Keeffe and O.M. Yaghi, "Assembly of Metal-Organic Frameworks from Large Organic and Inorganic Secondary Building Units: New Examples and Simplifying Principles for Complex Structures," J. Am. Chem. Soc., 2001, vol. 123, pp. 8239-8274.
Guillou, N., Q. Gao, P.M. Forster, J. Chang, M. Norgues, S. Park, G. Ferey and A.K. Cheetham, "Nickel (ii) Phosphate VSB-5: A Magnetic Nanoporous Hydrogenation Catalyst with 24-Ring Tunnels," Angew. Chem. Int. Ed., 2001, vol. 40, No. 15, pp. 2831-2834.
Naumov, P., G. Jovanovski, M. Ristova, I.A. Razak, S. Cakir, S. Chantrapromma, H. Fun and S. Weng NG, "Coordination of Deprotonated Saccharin in Copper(II) Complexes. Structural Role of the Saccharinate Directed by the Ancillary N-heterocyclic Ligands," Z. Anorg. Allg. Chem., 2002, vol. 628, pp. 2930-2939.
Wallner, H. and K. Gatterer, "Growth of Pure $Ni(OH)_2$ Single Crystals from Solution—Control of the Crystal Size," Z. Anorg. Allg. Chem., 2002, vol. 628, pp. 2818-2820.
Patoux, S. and C. Masquelier, "Lithium Insertion into Titanium Phosphates, Silicates and Sulfates," Chemistry of Materials, 2002, vol. 14, No. 12, pp. 5057-5068.
Rosi, N., M. Eddaoudi, J. Kim et al., "Infinite Secondary Building Units & Forbidden Catenation in Metal-Organic Frameworks", Angew. Chem. Int. Ed., 2002, 41, No. 2, pp. 284-285.
Eddaoudi, M., J. Kim, N. Rosi et al., "Systematic Design of Pore Size & Functionality in Isoreticular MOFs & Their Application in Methane Storage", Science, vol. 295, Jan. 18, 2002, pp. 469-472.
Seki, K., "Surface Area Evaluation of Coordination Polymers Having Rectangular Micropores", Langmuir 2002, 18, pp. 2441-2443.
Seki, K. and W. Mori, "Syntheses & Characterization of Microporous Coordination Polymers with Open Frameworks", J. Phys. Chem. B, 2002, 106, pp. 1380-1385.
Rosi, N. L., J. Eckert, M. Eddaoudi et al., "Hydrogen Storage in Microporous Metal-Organic Frameworks", Science, vol. 300, May 16, 2003, pp. 1127-1129.
Yaghi, O.M., M. O'Keeffe, N. W. Ockwig et al., "Reticular Synthesis and the Design of New Materials", Nature, vol. 423, Jun. 2003, pp. 705-714.
McGregor, Douglas S. et al., "Semi-Insulating Bulk GaAs Thermal Neutron Imaging Arrays," IEEE Transactions on Nuclear Science, vol. 43, No. 3, Jun. 1996, pp. 1357-1364.
Rose, A., "Sputtered Boron Films on Silicon Surface Barrier Detectors," Nuclear Instruments and Methods, 52, 1967, pp. 166-170.
Feigl, B. et al., "Der Gd-Neutronenzahler," Nuclear Instruments and Methods, 61, Wien, Austria, 1968, pp. 349-356.
Mireshghi, A. et al., "High Efficiency Neutron Sensitive Amorphous Silicon Pixel Detectors," IEEE Transactions on Nuclear Science, vol. 41, No. 4, Aug. 1994, pp. 915-921.
Foulon, F. et al., "Neutron Detectors Made From Chemically Vapour Deposited Semiconductors," Proc. MRS, 487, 1998, pp. 591-596.
Dulloo, A.R. et al., "Radiation Response Testing of Silicon Carbide Semiconductor Neutron Detectors for Monitoring Thermal Neutron Flux," Report 97-9TK1-Nusic-R1, Westinghouse STC, Pittsburgh, PA, Nov. 18, 1997, pp. 6-1-6-14.
Knoll, Glenn F., Radiation Detection and Measurement, 3rd Ed. John Wiley & Sons, Inc., New York, 2000, Chapter 14, pp. 505-508.
Garber, D.I. et al., "Neutron Cross Sections," 3rd Edition, vol. 11, Curves, Brookhaven National Laboratory, Upton, Jan. 1976, pp. 11-13 & pp. 23-24.
McLane, Victoria et al., "Neutron Cross Sections," vol. 2, Neutron Cross Section Curves, Academic Press, San Diego, CA, 1988, pp. 12-13 & pp. 26-27.
McGregor, Douglas, S. et al., "Thin-Film-Coated Bulk GaAs Detectors for Thermal and Fast Neutron Measurements," Nuclear Instruments and Methods in Physics Research A 466, 2001, pp. 126-141.
McGregor, Douglas, S. et al., "Design Considerations for Thin Film Coated Semiconductor Thermal Neutron Detectors—I: Basics Regarding Alpha Particle Emitting Neutron Reactive Films," Nuclear Instruments & Methods, A 500, 2003, pp. 272-308.
Puckett, P.R. et al., "Thin Film Processes II," Chapter V-2, J.L. Vossen and W. Kern, Eds., Academic Press, Boston, 1991, pp. 749, 768-770.
Sze, S .M. , "VLSI Technology," McGraw-Hill, New York, 1983.
Ruska, W.S., "Microelectronic Processing," McGraw-Hill, New York, 1987.

McGregor, Douglas, S. et al., "Self-Biased Boron-10 Coated High-Purity Epitaxial GaAs Thermal Neutron Detectors," IEEE Transactions on Nuclear Science, vol. 47, No. 4, Aug. 2000, pp. 1364-1370.
Klann, Raymond T. et al., "Development of Coated Gallium Arsenide Neutron Detectors," Conference Record of ICONE-8, 8TH International Conf. on Nuclear Eng., Apr. 2-6, 2000, Baltimore, MD, pp. 1-6.
McGregor, Douglas, S. et al., "New Surface Morphology for Low Stress Thin-Film-Coated Thermal Neutron Detectors," IEE Transactions on Nuclear Science, vol. 49, No. 4, Aug. 2002, pp. 1999-2004.
http://www.mems-exchange.org/.
http://physics.nist.gov/MajResProj/rfcell/drawings.html.
Schelten, J. et al., "A New Neutron Detector Development Based on Silicon Semiconductor and LiF Converter," Physica B 234-236, 1997, pp. 1084-1086.
Atomnaya Energiya, Soviet Atomic energy, Russian Original, vol. 62, No. 4, Apr. 1987, pp. 316-319.
Allier, C.P., "Micromachined Si-Well Scintillator Pixel Detectors," Chapter 8, 2001, pp. 122-134.
McGregor, Douglas S. et al., "Bulk GaAs-Based Neutron Detectors for Spent Fuel Analysis," Proceedings of ICONE 8, 8th Int'l Conf. on Nuclear Eng., Baltimore, MD, Apr. 2-6, 2000, pp. 1-5.
De Lurgio, Patrick M. et al., "A Neutron Detector to Monitor the Intensity of Transmitted Neutrons for Small-Angle Neutron Scattering Instruments," Elsevier Science B.V., Nuclear Instruments and Methods in Physics Research A 505, 2003, pp. 46-49.
Klann, Raymond T. et al., "Development of Semiconductor Detectors for Fast Neutron Radiography," 15th Int'l. conf. on Applications of Accelerators in Research and Industry, Nov. 2000, pp. 1-4.
Gersch, H.K. et al., "The Effect of Incremental Gamma-Ray Doses and Incremental Neutron Fluences Upon the Performance of Self-Biased 10B-Coated High-Purity Epitaxial GaAs Thermal Neutron Detectors," Nuclear Instruments and Methods in Physics Research A 489, Feb. 12, 2002, pp. 85-98.
McGregor, Douglas S. et al., "Thin-Film-Coated Detectors for Neutron Detection," J. of Korean Assoc. For Radiation Protection, vol. 26, 2001, pp. 167-175.
McGregor, Douglas, S. et al., "Designs for Thin-Film-Coated Semiconductor Thermal Neutron Detectors," University of Michigan, Ann Arbor, Michigan, Nov. 14, 2001, pp. 1-6.
McGregor, Douglas S. et al., "Recent Results From Thin-Film-Coated Semiconductor Neutron Detectors," Proceedings of SPIE, vol. 4784, 2002, pp. 164-182.
Chae et al.,"A route to high surface area, porosity and inclusion of large molecules in crystals," Nature, 2004, vol. 427, pp. 523-527.
Eddaoudi, M., J. Kim, , J. B. Wachter et al., "Porous Metal-Organic Polyhedra: 25Å Cuboctahedron Constructed from 12 $Cu_2$ $(CO_2)_4$ Paddle-Wheel Building Blocks," J. Am. Chem. Soc., 2001, 123, pp. 4368-4369.
Biradha, K., Y. Hongo & M. Fujita, "Open Square-Grid Coordination Polymers of the Dimension 20x20 Å: Remarkably Stable & Crystalline Solids Even After Guest Removal," Angew. Chem. Int. Ed., 2000, 39, No. 21, pp. 3843-3845 .
Li, Hailian, C.E. Davis, T.L. Groy, D.G. Kelley, O.M. Yaghi, "Coordinatively Unsaturated Metal Centers in the Extended Porous Framework of $Zn_3$6$CH_3$OH (BDC=1,4-Benzenedicarboxylate)," J. Am. Chem. Soc. 1998, 120, pp. 2186-2187.
Yaghi, O.M., G. Li, H. Li, "Selective binding and removal of guests in a microporous metal-organic framework," Nature, vol. 378(6558), Dec. 14, 1996, pp. 703-706.
Yaghi, O.M., C.E. Davis, G. Li, and H. Li, "Selective Guest Binding by Tailored Channels in a 3-D Porous Zinc (II)—Benzenetricarboxylate Network," J. Am. Chem. Soc. 1997, 199, pp. 2861-2868.
Yaghi, O.M., H. Li, "Hydrothermal Synthesis of a Metal-Organic Framework Containing Large Rectangular Channels," J. Am. Chem. Soc. 1995, 117, pp. 10401-10402.
Yaghi, O.M., H. Li, C. Davis, D. Richardson and T.L. Groy, "Synthetic Strategies, Structure Patterns, and Emerging Properties in the Chemistry of Modular Porous Solids," Acc. Chem. Res. 1998, 31, pp. 474-484.

Li, H., M. Eddaoudi, D.A. Richardson and O.M. Yaghi, Porous Germanates : Synthesis, Structure, and Inclusion Properties of $Ge_7O_{14.5}F_2$•[ $(CH_3)_2NH_2$]$_3$ $(H_2O)_{0.86}$, J. Am. Chem. Soc. , 1998, 120, pp. 8567-8568.
Li, H., M. Eddaoudi, T.L. Groy and O.M. Yaghi, Establishing Microporosity in Open Metal—Organic Frameworks: Gas Sorption Isotherms for Zn(BDC) (BDC = 1,4-Benzenedicarboxylate), J. Am Chem. Soc. 1998, 120, pp. 8571-8572.
Li, H. and O.M. Yaghi, "Transformation of Germanium Dioxide to Microporous Germanate 4-Connected Nets," J. Am Chem. Soc. 1998, 120, pp. 10569-10570.
Reineke, T.M., M. Eddaoudi, M. Fehr, D. Kelley and O.M. Yaghi, "From Condensed Lanthanide Coordination Solids to Microporous Frameworks Having Accessible Metal Sites," J. Am. Chem. Soc. 1999, 121, pp. 1651-1657.
Li, H., M. Eddaoudi and O.M. Yaghi, "An Open-Framework Germanate with Polycubane-Like Topology," Angew. Chem. Int. Ed. 1999, 38, No. 5, pp. 653-655.
Reineke, T.M., M. Eddaoudi, M. O'Keeffe and O.M. Yaghi, "A Microporous Lanthanide—Organic Framework," Angew. Chem. Int. Ed. 1999, 38, No. 17, pp. 2590-2594.
Chen, B., M. Eddaoudi, T.M. Reineke, J.W. Kampf, M. O'Keeffe and O.M. Yaghi, $Cu_2$(ATC)•6$H_2$O: Design of Open Metal Sites in Porous Metal-Organic Crystals (ATC: 1,3,5,7-Adamantane Tetracarboxylate), J. Am. Chem. Soc. 2000, 122, pp. 11559-11560.
Chae, H.K., M. Eddaoudi, J. Kim, S.I. Hauck, J.F. Hartwig, M. O'Keeffe and O.M. Yaghi, "Tertiary Building Units: Synthesis, Structure, and Porosity of a Metal-Organic Dendrimer Framework (MODF-1)," J. Am. Chem. Soc. 2001, 123, pp. 11482-11483.
Braun, M.E., C.D. Steffek, J. Kim, P.G. Rasmussen and O.M. Yaghi, "1,4-Benzenedicarboxylate derivatives as links in the design of paddle-wheel units and metal-organic frameworks," Chem. Commun., 2001, pp. 2532-2533.
Barton, T.J., L.M. Bull, W.G. Klemperer, D.A. Loy, B. McEnaney, M. Misono, P.A. Monson, G. Pez, G.W. Scherer, J.C. Vartuli and O.M. Yaghi, "Tailored Porous Materials," Chem. Mater. 1999, 11, pp. 2633-2656.
Eddaoudi, M., J. Kim, M. O'Keeffe and O.M. Yaghi, "$Cu_2$[o-Br-$C_6H_3$$_{(CO2)}$$_2$]$_2$ $(H_2O)_2$•(DMF)$_8$ $(H_2O)_2$: A Framework Deliberately Designed to Have the NbO Structure Type," J. Am. Chem. Soc., 2002, vol. 124, No. 3, pp. 376-377.
Rosi, N. L., M. Eddaoudi, J. Kim, M. O'Keeffe and O.M. Yaghi, "Advances in the chemistry of metal-organic frameworks," CrystEngComm, 2002, 4(68), pp. 401-404.
Plevert, J., R. Sanchez-Smith, T.M. Gentz, H. Li, T.L. Groy, O.M. Yaghi and M. O'Keeffe, "Synthesis and Characterization of Zirconogermanates," Inorganic Chemistry, vol. 42, No. 19, 2003, pp. 5954-5959.
Vodak, D.T., K. Kim, L. Iordanidis, P.G. Rasmussen, A.J. Matzger and O.M. Yaghi, "Computation of Aromatic $C_3N_4$ Networks and Synthesis of the Molecular Precursor $N(C_3N_3)_3Cl_6$," Chem. Eur. J. 2003, 9, pp. 4197-4201.
Olaf Delgado Friedrichs, Michael O'Keeffe and Omar M. Yaghi, "Three-periodic nets and tilings: regular and quasiregular nets," Acat Cryst., 2003, A59, pp. 22-27.
Olaf Delgado Friedrichs, Michael O'Keeffe and Omar M. Yaghi, "Three-periodic nets and tilings: semiregular nets," Acat Cryst., 2003, A59, pp. 515-525.
Hailian Li, Jaheon Kim, Michael O'Keeffe and Omar M. Yaghi, "[$Cd_{16}In_{64}S_{134}$]$^{44-}$: 31-Å Tetrahedron with a Large Cavity," Angew. Chem. Int. Ed., 2003, 42, pp. 1819-1821.
Chae, H.K., J. Kim, O.D. Friedrichs, M. O'Keeffe and O.M. Yaghi, "Design of Frameworks with Mixed Triangular and Octahedral Building Blocks Exemplified by the Structure of [$Zn_4O(TCA)_2$] Having the Pyrite Topology," Angew. Chem. Int. Ed, 2003, 42, pp. 3907-3909.
Plevert, J., T.M. Gentz, T.L. Groy, M. O'Keeffe and O.M. Yaghi, "Layered Structures Constructed from New Linkages of $Ge_7$(O,OH,F)19 Clusters," Chem. Mater., 2003, 15, pp. 714-718.
Duren, T., L. Sarkisov, O.M. Yaghi and R.Q. Snurr, "Design of New Materials for Methane Storage," Langmuir, 2004, 20, pp. 2683-2689.

Rowsell, J.L.C., A.R. Millward, K.S. Park and O.M. Yaghi, "Hydrogen Sorption in Functionalized Metal-Organic Frameworks," J. Am. Chem. Soc., 2004, 126, pp. 5666-5667.

Rowsell, J.L.C., O.M. Yaghi, "Metal-organic frameworks: a new class of porous materials," Microporous and Mesoporous Materials 73 (2004), pp. 3-14.

Rosi, N.L., J. Kim, M. Eddaoudi, B. Chen, M. O'Keeffe and O.M. Yaghi, "Rod Packings and Metal-Organic Frameworks Constructed from Rod-Shaped Secondary Building Units," J. Am. Chem. Soc., 2005, 127, pp. 1504-1518.

Chen, B., N. W. Ockwig, F.R. Fronczek, D.S. Contreras and O.M. Yaghi, "Transformation of a Metal-Organic Framework from the NbO to PtS Net," Inorganic Chemistry, vol. 44, No. 2, 2005, pp. 181-183.

Banerjee, R. et al., "High-Throughput Synthesis of Zeolitic Imidazolate Frameworks and Application to CO2 Capture," Science, American Assn for the Advancement of Science, Washington, D.C., v. 319, n. 5865, Feb. 15, 2008, pp. 939-943.

Bogdashev, N. N. et al., "Study of the Anodic Behavior of Cobalt, Nickel, and Copper in Methanol Solutions during Electrochemical Synthesis of N-metal-substituted Azoles," Database Caplus [Online] Chemical Abstracts Service, Columbus, OH, 1976, XP-002447401, 1 page.

Lehnert et al., "Die Kristallstruktur des Eisen(II)-Derivates des Imidazols," Zeitschrift fuer Anorganische unde Allgemeine Chemie, v. 444, No. 1, 1978, pp. 91-96 (Abstract included).

Lehnert et al., "Darstellung und Kristallstruktur des Mangan(II)- und Zink(II)-Derivates des Imidazols," Zeitschrift fuer Anorganische unde Allgemeine Chemie, v. 464, No. 1, 1980, pp. 187-194 (Abstract included).

Liu, Y. et al., "Molecular Building Blocks Approach to the Assembly of Zeolite-Like metal-Organic Frameworks (SMOFs) with Extra-Large Cavities," Chemical Communications, v. 2006, n. 14, Feb. 2, 2006, pp. 1488-1490.

Rettig, S.J. et al., "Polybis(4-azabenzimidazolato)-iron(II) and -cobalt(II) 3-D single diamond-like framework materials which exhibit spin canting and ferromagnetic ordering at low temperatures," J. of the Chem. Soc., v. 2000, n. 21, Sep. 21, 2000, pp. 3931-3937.

Zhang, J-P et al., "Crystal Engineering of Binary Metal Imidazolate and Triazolate Frameworks," Chemical Communications, v. 2006, n. 16, Jan. 23, 2006, pp. 1689-1699.

Park, Kyo Sung et al., "Exceptional Chemical and Thermal Stability of Zeolitic Imidazolate Frameworks," Proc. of the Nat'l Academy of Sciences of the US (PNAS), Nat'l Ac. of Science, v. 103, n. 27, Jul. 5, 2006, pp. 10186-10191.

Extended Ep Search Report dated Dec. 3, 2010 in corresponding EP Appn. 07757619.7, filed Feb. 28, 2007, 7 pages.

\* cited by examiner (a)

(b)

Benzimidazolate
SOD : ZIF-7  (T = Zn)
RHO : ZIF-11 (T = Zn)

4-Azabenzimidazolate
dia : ZIF-23 (T = Zn)

Purinate
LTA : ZIF-20 (T = Zn)
LTA : ZIF-21 (T = Co)

5-Azabenzimidazolate
LTA : ZIF-22 (T = Zn)

ZIF-20

ZIF-21

ZIF-22

ZIF-23

PREPARATION OF FUNCTIONALIZED ZEOLITIC FRAMEWORKS

CROSS REFERENCE TO RELATED APPLICATIONS

This application claims priority under 35 U.S.C. §119(e) to U.S. Provisional Application No. 60/777,739, filed Feb. 28, 2006, and to U.S. Provisional Application No. 60/886,492, filed Jan. 24, 2007, the disclosures of which are incorporated herein by reference in their entirety.

STATEMENT REGARDING FEDERALLY SPONSORED RESEARCH OR DEVELOPMENT

This invention was made with Government support under Grant No. DE-FG02-06ER15813, awarded by the Department of Energy and DMR0242630, awarded by the National Science Foundation. The government has certain rights in the invention.

FIELD OF THE INVENTION

In at least one aspect, the present invention relates to crystalline zeolites and to methods of use thereof.

BACKGROUND

A large segment of the global economy ($350 billion) is based on the use of crystalline microporous zeolites in petrochemical cracking, ion-exchange for water softening and purification, and in the separation of gases. Zeolite structures are composed of tetrahedral $Si(Al)O_4$ units covalently joined by bridging O atoms to produce ~150 different types of framework. A long-standing challenge is to incorporate transition metal ions and organic units within their pores and, more desirably, to do so as an integral part of the zeolite framework. This ability would be useful in many catalytic applications because the pores would be lined with a high concentration of ordered transition metal sites whose electronic and steric properties can be tailored by functionalization of the organic links. However, the vision of achieving such a zeolite that combines these features remains largely unrealized.

SUMMARY

An embodiment of the present invention provides a zeolitic framework, comprising the general structure M-L-M, wherein M comprises a transition metal and L is a linking moiety comprising a structure selected from the group consisting of I, II, III, or any combination thereof:

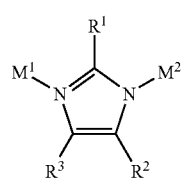

(I)

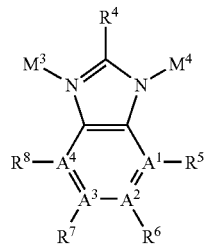

(II)

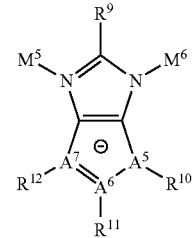

(III)

wherein A, $A^1$, $A^2$, $A^3$, $A^4$, $A^5$, $A^6$, and $A^7$ can be either C or N, wherein $R^5$-$R^8$ are present when $A^1$ and $A^4$ comprise C, wherein $R^1$, $R^4$ or $R^9$ comprise a non-sterically hindering group that does not interfere with M, wherein $R^2$, $R^3$, $R^5$, $R^6$, $R^7$, $R^8$, $R^{10}$, $R^{11}$, $R^{12}$ are each individually an alkyl, halo-, cyano-, or nitro-, wherein $M^1$, $M^2$, $M^3$, $M^4$, $M^5$, $M^6$ each comprise a transition metal (these are instances of M), wherein when the linking group comprises structure III, $R^{10}$, $R^{11}$ and $R^{12}$ are each individually electron withdrawing groups. In one embodiment $R^1$, $R^4$ and $R^9$ are individually small groups selected from the group consisting of H, methyl-, halo-, cyano-, and ethyl-. In another embodiment, $R^{10}$, $R^{11}$ and $R^{12}$ are each individually selected from the group consisting of a nitro-, cyano-, fluoro- and chloro-group. In one embodiment, the linking moeity is an imidazolate or an imidazolate derivative. In a further embodiment the imidazolate or imidazolate derivate is selected from the group consisting of IV, V, VI, VII, VIII, and IX:

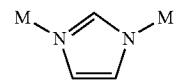

IV

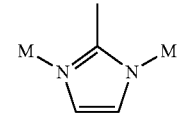

V

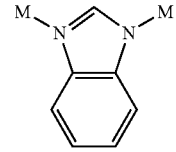

VI

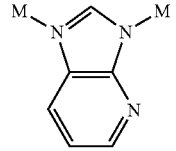

VII

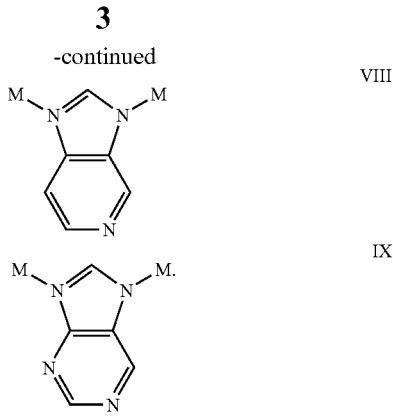

In one embodiment, the imidazolate or imidazolate derivative is selected from the group consisting of a substituted imidazolate; a benzimidazolate comprising a methyl-, nitro-, cyano-, or chloro-group; an azabenzimidazolate; and an azabenzimidazolate wherein one or two carbon atoms on the benzimidazolate are replaced by nitrogen. The transition metal is selected from the group consisting of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg and Uub. In one aspect, a zeolitic framework comprises a heterogeneous combination of transition metals. In yet another embodiment, the zeolitic framework comprises homogenous transition metal(s) but a heterogeneous combination of linking moieties. In a further embodiment, a zeolitic framework comprises a heterogeneous mixture of transition metals and linking moieties.

In at least one variation, the present invention provides a zeolitic framework wherein the zeolitic framework comprises a framework structure selected from the group consisting of ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EON, EPI, ERI, ESV, ETR, EUO, EZT, FAR, FAU, FER, FRA, GIS, GIU, GME, GON, GOO, HEU, IFR, IHW, ISV, ITE, ITH, ITW, IWR, IWV, IWW, JBW, KFI, LAU, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG, and ZON, wherein the framework comprises a plurality of transition metal linked by a linking moeity set forth in any one or more of structure I-IX.

Variations of zeolitic frameworks of the invention can comprise one or more of the following characteristics: a surface area of a pore of the plurality of pores is greater than about 2000 m$^2$/g; a surface area of a pore of the plurality of pores is about 3,000-18,000 m$^2$/g; a surface area of a pore of the plurality of pores is about 3,000-6,000 m$^2$/g; a pore of the plurality of pores comprises a pore volume 0.1 to 0.99 cm$^3$/g; a pore of the plurality of pores comprises a pore volume of 0.4-0.5 cm$^3$/g; a framework density of about 0.17 g/cm$^3$; atomic coordinates as set forth in any one of the tables described herein.

Some zeolitic frameworks of the invention may be interpenetrating. Furthermore, some zeolitic frameworks of the invention can be used to adsorbed chemical species (e.g., ammonia, carbon dioxide, carbon monoxide, hydrogen, amines, methane, oxygen, argon, nitrogen, argon, organic dyes, polycyclic organic molecules, and combinations thereof). Some zeolitic frameworks of the invention can be used for gas storage, in sensors and as a catalyst.

DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
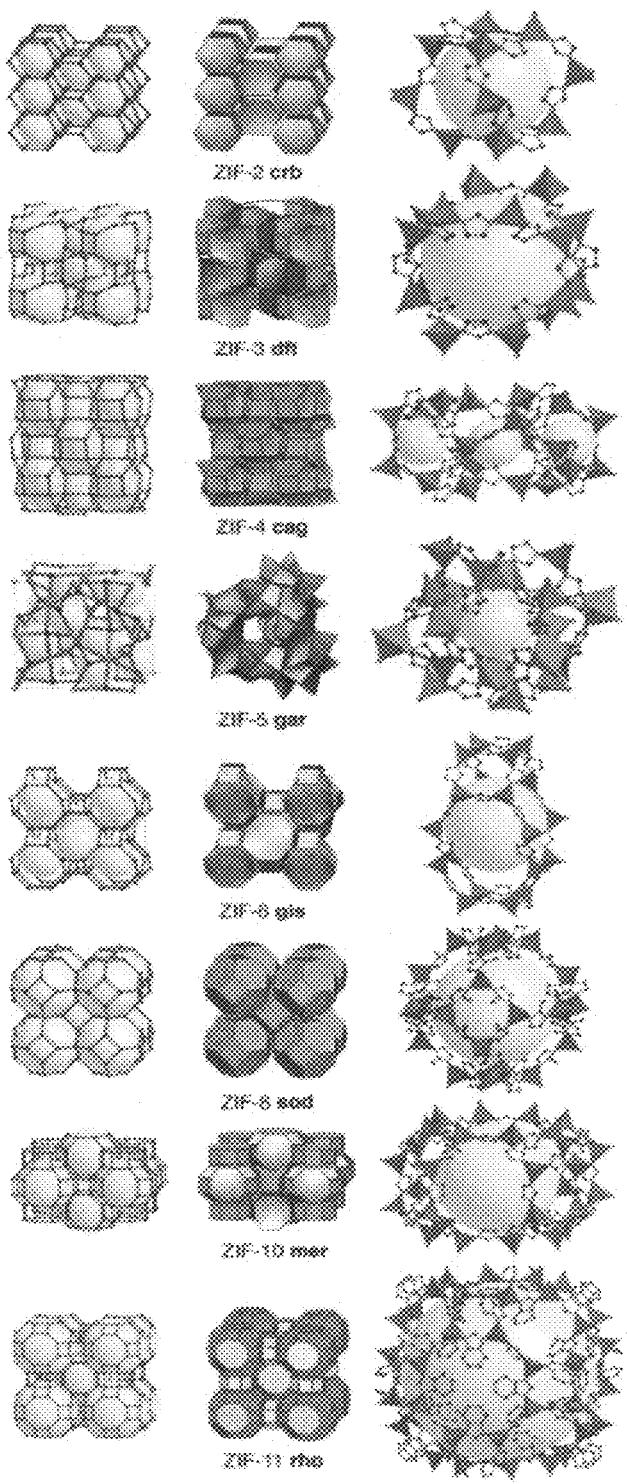
FIG. 1 shows the single crystal x-ray structures of ZIFs. (Left and Center) In each row, the net is shown as a stick diagram (Left) and as a tiling (Center). (Right) The largest cage in each ZIF is shown with ZnN$_4$ tetrahedra in gray, and, for ZIF-5, InN6 octahedra in gray. H atoms are omitted for clarity.

As used herein and in the appended claims, the singular forms "a," "and," and "the" include plural referents unless the context clearly dictates otherwise. Thus, for example, reference to "a pore" includes a plurality of such pore and reference to "the metal" includes reference to one or more metals known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Zeolitic frameworks are a class of porous materials that potentially have the advantages both of inorganic zeolites (e.g., high stability) and of MOFs (e.g., high porosity and organic functionality), which could be applied to highly efficient catalysis and separations. From a synthetic perspective, zeolitic framework topologies can be directed by the molecular structure of the organic linker and rationalized by examining the resulting linker-linker interactions in the zeolitic frameworks. The potential difficulty in predicting zeolitic structures, such as is always encountered in zeolite chemistry, can be overcome by further detailing the linker requirements for forming the basic secondary building units (cube in the case LTA) in the structure.

Existing zeolites are crystalline aluminosilicates having ordered channel and cage structures and containing micropores which are typically smaller than about 0.9 nm. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolite Structure Types", Elsevier, 5th edition, Amsterdam 2001. Specific examples are zeolites having a pentasil structure, in particular the types assigned by X-ray analysis to the ABW, AGO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG and ZON structure and to mixed structures of two or more of the above mentioned structures.

The concept of a default structure (a naturally preferred high-symmetry topology most often adopted by a solid-state material) does not apply directly either to silicates or imidazolate. The 145° angle makes it impossible for the highest symmetry 4-coordinated structure of Fd3m diamond to form; therefore, lower symmetries are invariably found for silicas. Nature prefers $P3_121$ quartz over the $P4_12_12$ cristobalite polymorph, but by only 1 or 2 kJ/mol, and >10 forms of silica are known to be of essentially equal energy (on the scale of bond energies). To reproducibly prepare these and related structures, one needs a structure-directing agent, and this agent is a key to zeolite synthesis. The disclosure shows that structure-directing agents (amide solvent media and linker functionalization) along with control of reaction conditions are effective in achieving a wide variety of zeolitic structures.

To date, no metal-organic analogues based on the important FAU or LTA topologies exist due to difficulty imposed by the presence of two types of large cages (super- and β-cages for FAU, α- and β-cages for LTA). The dislcosure identifies a strategy to produce an LTA imidazolate framework in which both the link geometry and link-link interactions play a decisive structure-directing role. The disclosure provides, for example, the synthesis and crystal structures of porous zeolitic structures that are expanded analogues of zeolite A, their cage walls are functionalized, and their metal ions can be changed without changing the underlying LTA topology; these are attributes highly sought after in zeolite chemistry but not before combined in one material.

As used herein, a "core" refers to a repeating unit or units found in a framework. Such a framework can comprise a homogenous repeating core or a heterogenous repeating core structure. A core comprises a transition metal and a linking moiety. A plurality of cores linked together defines a framework.

A "linking moiety" refers to a mono-dentate or bidentate compound that bind a transition metal or a plurality of transition metals, respectively.

A "zeolitic framework," as used herein, refers to a framework of repeating cores having a zeolite-type structure.

A "zeolitic imidizolate framework" or "ZIF" refers to a zeolitic framework comprising a zeolitic structure having an imidizole, imidizolate-derivative, or imidizolate linking group.

The disclosure provides zeolitic frameworks comprising a network of homogenous transition metal or heterogeneous transition metals linked by a homogenous or heterogeneous linking moiety. The zeolitic frameworks of the disclosure can comprise any of the networks currently defined in the Atlas of Zeolite Structure Types known in the literature. The zeolitic frameworks of the disclosure provide nanoporous structure useful for filtration, gas storage and the like, as more fully described herein.

The disclosure also provide a general synthesis of structures having zeolite framework topologies in which all tetrahedral atoms are transition metals, and the linking moieties comprise organic linkers comprising nitrogen, sulfur or oxygen organic molecules (e.g., such as imidazolate (IM) units).

The compositions of the disclosure comprise a zeolite tetrahedral net comprising a transition metal core and a linking moeity. Useful transition metal comprise any one or more of the following: Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, and Uub. A linker useful in the zeolite compositions of the disclosure can be selected from the group consisting of structure I, II, III, and any combination thereof:

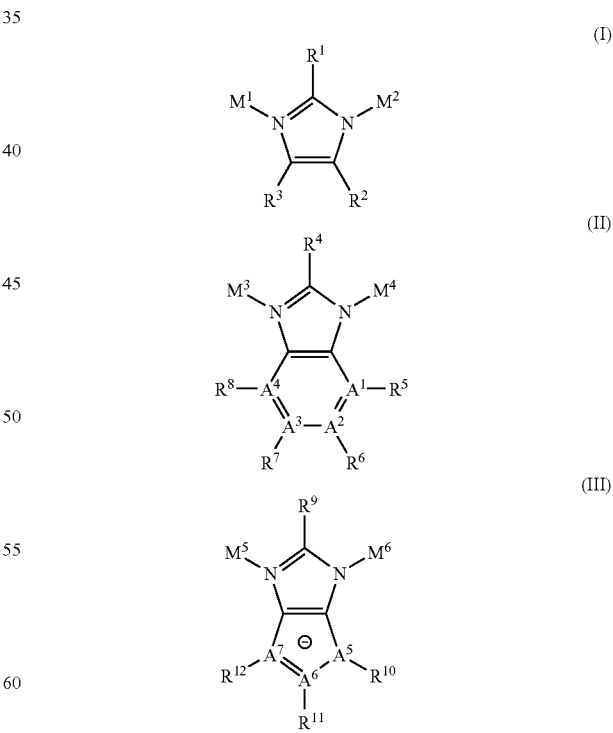

wherein A, $A^1$, $A^2$, $A^3$, $A^4$, $A^5$, $A^6$, and $A^7$ can be either C or N, wherein $R^5$-$R^8$ are present when $A^1$-$A^4$ comprise C, wherein $R^1$, $R^4$ or $R^9$ comprise a non-sterically hindering group (e.g., alkyl group) that does not interfere with a transition metal (M) linked to the linking moiety, wherein $R^2$, $R^3$, $R^5$, $R^6$, $R^7$, $R^8$, $R^{10}$, $R^{11}$, $R^{12}$ are each individually an alkyl, aryl-, halo-, cyano- or nitro-, wherein $M^1$, $M^2$, $M^3$, $M^4$, $M^5$, $M^6$ each comprise a transition metal, wherein when the linking group comprises structure III, $R^{10}$, $R^{11}$ and $R^{12}$ are each individually electron withdrawing groups. In one aspect, $R^1$, $R^4$ and $R^9$ are individually small group selected from the group consisting of H, methyl-, halo-, cyano-, and ethyl-. In another aspect, when the linking moiety is structure III, $R^{10}$, $R^{11}$ and $R^{12}$ are each individually selected from the group consisting of a nitro-, cyano-, fluoro-, and chloro-group. In a variation of the present invention, an alkyl group can have from 1 to 10 carbon atoms and an aryl group can have from 1 to 5 phenyl rings. In another aspect, the linking moiety can be bidentate or monodentate. A zeolitic framework can comprise a combination of bidentate or monodentate linking moeities. As described more fully below, the linking group can comprise an imidizole or imidizolate moiety such as a member selected from the group consisting of IV, V, VI, VII, VIII, and IX:

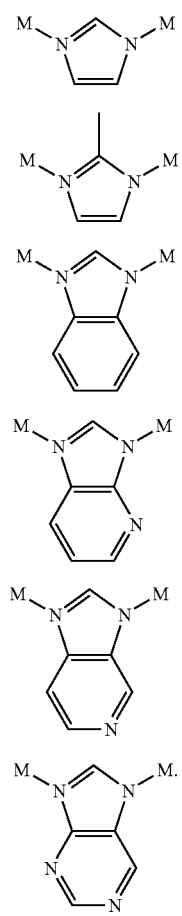

IV

V

VI

VII

VIII

IX

For example, hetercyclic rings including imidazolate compounds and derivative such as substituted imidazolate, benzimidazolate, methyl-, nitro-, cyano, or chloro-groups, azabenzimidazolate, azabenzimidazolte wherein one or two carbon atoms on the benzimidazolate are replaced by nitrogen and the like can be used.

The zeolitic framework (e.g., a ZIF) of the disclosure can take any framework/structure. For example, using the methods of the disclosure, ZIFs having any of the following framework codes can be obtained: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EON, EPI, ERI, ESV, ETR, EUO, EZT, FAR, FAU, FER, FRA, GIS, GIU, GME, GON, GOO, HEU, IFR, IHW, ISV, ITE, ITH, ITW, IWR, IWV, IWW, JBW, KFI, LAU, LEV, LIO, LIT, LOS, LOV, LTA, LTL, LTN, MAR, MAZ, MEI, MEL, MEP, MER, MFI, MFS, MON, MOR, MOZ, MSE, MSO, MTF, MTN, MTT, MTW, MWW, NAB, NAT, NES, NON, NPO, NSI, OBW, OFF, OSI, OSO, OWE, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN, SFO, SGT, SIV, SOD, SOS, SSY, STF, STI, STT, SZR, TER, THO, TON, TSC, TUN, UEI, UFI, UOZ, USI, UTL, VET, VFI, VNI, VSV, WEI, WEN, YUG, and ZON A transition metal and linking moiety core have been used to generate a plurality of zeolitic frameworks. For example, zeolitic imidazolate frameworks (ZIFs) have been synthesized as crystals by copolymerization of transition metals with imidazolate-type links. The ZIF crystal structures are based on the nets of a plurality of distinct aluminosilicate zeolites: tetrahedral Si(Al) and the bridging O are replaced with transition metal ion and an imidazolate link, respectively. Study of the gas adsorption and thermal and chemical stability of the ZIFs demonstrated their porosity (Langmuir surface area of about 1,810 m$^2$/g), high thermal stability (up to 550° C.), and remarkable chemical resistance to boiling alkaline water and organic solvents.

Imidazole, for example, can lose a proton to form IM. The core of such frameworks can be formulated T(Im)$_2$ (Im=imidazolate and its derivatives, T=tetrahedrally bonded metal ion) and are similar to the (Al)SiO$_2$ frameworks of (alumino)silicate zeolites; in particular the T-Im-T angle of about 145° is close to the Si—O—Si angle typically found in zeolites In examining the dense-phases Co(IM)2 and Zn(IM) 2, whose structures are based on nets of linked CoN$_4$ or ZnN$_4$ tetrahedra, the angle is as depicted in Scheme 1.

Scheme I

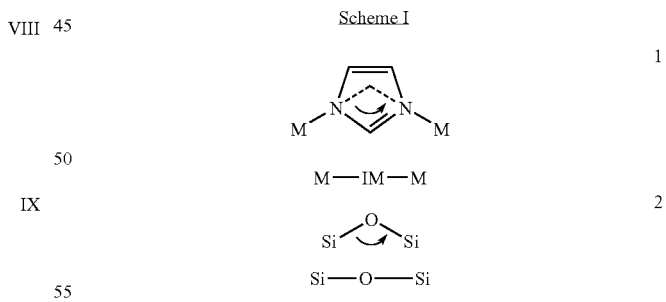

Accordingly, under the right conditions metal IMs adopt open-framework zeolite structures. Indeed, a number of new Fe(II) (5), Co(II), Cu(II), and Zn(II) IM compounds have structures that are based on zeolite-like tetrahedral nets.

The disclosure provides a general strategy that has led to zeolitic structures based on other zeolite nets. The disclosure confirms the porosity of ZIFs of the disclosure and unlike other metal-organic compounds, the zeolitic frameworks (ZIFs) have exceptional chemical stability in refluxing organic solvents, water, and aqueous alkaline solution, a finding that has not been described previously. These results point to the potential applications and rich structural diversity of this as-yet-undeveloped class of porous materials.

A zeolitic framework of the disclosure, such as a ZIF, can be synthesized by using solvothermal methods. Highly crystalline materials were obtained by combining the requisite hydrated metal salt (e.g., nitrate) and imidazole-type linker in an amide solvent such as N,N-diethylformamide (DEF). The resulting solutions were heated (85-150° C.) and zeolitic frameworks of the disclosure where precipitated after 48-96 hours and were readily isolated. Single crystals suitable for x-ray structure analysis were selected from the precipitate. FIG. 1 illustrates examples of precipitated structures. In FIG. 1, the metal center of each structure is coordinated by the N atoms of IM to give overall neutral frameworks. The five-membered IM ring, as depicted in FIG. 1, serves as the bridging/linking unit between the transition metal centers and imparts angle 1 of ~145° throughout the frameworks via coordinating N atoms in the 1,3-positions of the ring. The organic components of the zeolitic framework provides organically lined cages and channels rather than a silicate oxide surface as in prior zeolites.

The zeolitic frameworks of the disclosure are comparable with some of the very porous MOF compounds in surface area and pore volume, and they outperform traditional crystalline microporous materials such as zeolites and ordered mesoporous silicas. Although not required and not wanting to be bound by any theory, this performance may be due in part to the fully exposed edges and faces of the organic links; characteristics that have been proposed as key to creating exceptionally high surface areas.

The frameworks comprising a core, wherein the core comprises a plurality of transition metals linked by linking moiety having a structure selected from I-IX, comprises a plurality of pores having a surface area greater than about 2000 $m^2/g$ (e.g., about 3,000-18,000 $m^2/g$ or about 3,000-6,000 $m^2/g$). The plurality of pores of a framework of the disclosure comprises a pore volume 0.1 to 0.99 $cm^3/cm^3$ (e.g., about 0.4-0.5 $cm^3/cm^3$). A framework of the disclosure comprises a density of about 0.17 $g/cm^3$. A zeolitic framework of the disclosure can comprise a core comprising the atomic coordinates as set forth in any one of the tables herein.

In another aspect, the zeolitic framework set forth above may include an interpenetrating frameworks that increases the surface area of the framework. Although the frameworks of the disclosure may advantageously exclude such interpenetration, there are circumstances when the inclusion of an interpenetrating framework may be used to increase the surface area.

In one embodiment of the disclosure, a gas storage material comprising a zeolitic framework is provided. Advantageously, the zeolitic framework includes one or more sites for storing gas molecules. Gases that may be stored in the gas storage material of the disclosure include gas molecules comprising available electron density for attachment to the one or more sites on the surface are of a pore or interpenetrating porous network. Such electron density includes molecules having multiple bonds between two atoms contained therein or molecules having a lone pair of electrons. Suitable examples of such gases include, but are not limited to, the gases comprising a component selected from the group consisting of ammonia, argon, carbon dioxide, carbon monoxide, hydrogen, and combinations thereof. In a particularly useful variation the gas storage material is a hydrogen storage material that is used to store hydrogen ($H_2$). In another particularly useful variation, the gas storage material is a carbon dioxide storage material that may be used to separate carbon dioxide from a gaseous mixture.

In a variation of this embodiment, the gaseous storage site comprises a pore in a zeolitic framework. In a refinement, this activation involves removing one or more chemical moieties (guest molecules) from the zeolitic framework. Typically, such guest molecules include species such as water, solvent molecules contained within the zeolitic framework, and other chemical moieties having electron density available for attachment.

The zeolitic framework used in the embodiments of the disclosure include a plurality of pores for gas adsorption. In one variation, the plurality of pores has a unimodal size distribution. In another variation, the plurality of pores have a multimodal (e.g., bimodal) size distribution.

The disclosure also provide chemical sensors (e.g. resistometric sensors) capable of sensing the presence of an analyte of interest. There is considerable interest in developing sensors that act as analogs of the mammalian olfactory system. However, may such sensor systems are easily contaminated. The porous structures of the disclosure provide a defined interaction area that limits the ability of contaminate to contact a sensor material the passes through the porous structure of the zeolitic framework of the disclosure. For example, various polymers are used in sensor systems including conductive polymers (e.g., poly(anilines) and polythiophenes), composites of conductive polymers and non-conductive polymers and composites of conductive materials and non-conductive materials. In resistometric systems conductive leads are separated by the conductive material such that a current traverse between the leads and through the sensor material. Upon binding to an analyte, the resistance in the material changes and detectable signal is thus generated. Using the zeolitic framework of the disclosure, the area surrounding the sensor material is limited and serves as a "filter" to limit contaminants from contacting the sensor material, thus increasing sensor specificity.

The disclosure further provides zeolitic catalyst comprising a zeolitic framework of the disclosure. The zeolitic material of the disclosure, as crystalline material or as molding, can be used in the catalytic conversion of organic molecules. Reactions of this type are, for example, oxidations, the epoxidation of olefins, e.g. the preparation of propylene oxide from propylene and $H_2O_2$ the hydroxylation of aromatics, e.g. the preparation of hydroquinone from phenol and $H_2O_2$ or the conversion of toluene into cresol, the conversion of alkanes into alcohols, aldehydes and acids, isomerization, reactions, for example the conversion of epoxides into aldehydes.

The invention is illustrated in the following examples, which are provided by way of illustration and are not intended to be limiting.

EXAMPLES

To illustrate the potential for synthetic diversity of the disclosure, Table 1 demonstrates zeolite topologies DFT, GIS, and MER resulting from the methods of the disclosure. Furthermore, the disclosure demonstrates that the ZIFs of the disclosure are not restricted to purely tetrahedral nets. The first example of an IM based on a mixed-coordination net, $In_2Zn_3(IM)_{12}$ with In(III) in octahedral coordination environment, is also reported. This structure has the topology of the $Al_2Si_3O_{12}$ part of a garnet, such as grossularite $Ca_3Al_2Si_3O_{12}$. The synthesis of this structure hints at the extraordinarily rich chemistry using linking moieties of the disclosure, such as IMs.

TABLE 1

Composition, structure, and net parameters of ZIF series of compounds

| ZIF-n | Composition | Net* | Zeolite† | T/V,‡ nm⁻³ | d,§ Å | N¶ |
|---|---|---|---|---|---|---|
| ZIF-1 | Zn(IM)2 | crb | BCT | 3.64 | 6.94 | 12 |
| ZIF-2 | Zn(IM)2 | crb | BCT | 2.80 | 6.00 | 12 |
| ZIF-3 | Zn(IM)2 | dft | DFT | 2.66 | 8.02 | 16 |
| ZIF-4 | Zn(IM)2 | cag | — | 3.68 | 2.04 | 20 |
| ZIF-5 | In2Zn3(IM)12 | gar | — | 3.80 | 3.03 | 20 |
| ZIF-6 | Zn(IM)2 | gls | GIS | 2.31 | 8.80 | 20 |
| ZIF-7 | Zn(PhIM)2 | sod | SOD | 2.50 | 4.31 | 24 |
| ZIF-8 | Zn(MeIM)2 | sod | SOD | 2.47 | 11.60 | 24 |
| ZIF-9 | Co(PhIM)2 | sod | SOD | 2.51 | 4.31 | 24 |
| ZIF-10 | Zn(IM)2 | mer | MER | 2.25 | 12.12 | 24 |
| ZIF-11 | Zn(PhIM)2 | rho | RHO | 2.01 | 14.64 | 48 |
| ZIF-12 | Co(PhIM)2 | rho | RHO | 2.01 | 14.64 | 48 |

*For definitions of three-letter abbreviations, see Reticular Chemistry Structure Resource (http:~~okeeffe-ws1.la.asu.edu/RCSR/home.htm).
†T/V is the density of metal atoms per unit volume.
§d is the diameter of the largest sphere that will fit into the framework.
¶N is the number of vertices of the largest cage.

Table 1 summarizes topology, density, and pore size data for some of the ZIFs of the disclosure. The nets of the structures are denoted by a three-letter symbol that is often the same as that of the corresponding zeolite net. The density of ZIFs are denoted by using the traditional zeolite measure of number of tetrahedral vertices per unit volume (T/V). In an IM framework containing, for example, Zn(II), the Zn . . . Zn distance is ~6.0 Å, whereas the corresponding Si . . . Si distance in a silicate is ~3.0 Å; accordingly, the density (T/V) of an IM analog (i.e., ZIF) of a silicate zeolite is eight times less. For the structures reported here, T/V is in the range 2.0-3.7 nm (Table 1). For comparison, the density for oxide zeolites is 12-20 nm⁻³, and for the lowest-density known oxide framework it is 7.1 nm⁻³. Also provided are examples of the size of the sphere that will fit into the cavities without contacting the van der Waals internal surface of the framework. The atom nearest to the center of the cavity is H, a van der Waals radius of 1.2 Å was used for H in determining the fitting sphere size. Note that this value is an approximate indicator of the cage volume because in some cases the cages are elliptical. The table also gives the number of vertices of the largest cage in each structure; this value ranges from 12 (crb) to 48(rho).

In FIG. 1, eight nets of the ZIF structures of the disclosure are depicted in three ways. First, as stick diagrams of the nets; next, the same structures decomposed into tiles (generalized polyhedra or cages that combine to completely fill space). For some structures (i.e., cag, gis, and sod) there is just one kind of tile. Finally, the largest cage in the real structure of representative IMs is shown on the right. Replacement of Zn(II) by Co(II) makes essentially no metrical difference to the structure; thus, ZIF-7 and -11 are virtually identical to ZIF-9 and -12, respectively.

Porosity and Stability of ZIFs. Certain ZiFs were prepared at the gram scale to allow detailed investigation of the their properties. A structural feature of these ZIFs is that they possess large pores (11.6 and 14.6 Å in diameter for ZIF-8 and -11, respectively) connected through small apertures (3.4 and 3.0 Å across for ZIF-8 and -11, respectively). The pore sizes are approximately twice as large as those of their zeolite counterparts by virtue of the longer IM linking units; however, the existence of side chain or ring on the link renders the aperture sizes to the lower limit for molecular sieves (Table 2).

TABLE 2

Structural characteristic of ZIF-8 and -11 calculated from single crystal x-ray analysis

| | Pore aperture diameter, Å | | | | | |
|---|---|---|---|---|---|---|
| ZIF-n | 8-ring | 6-ring | 4-ring | Pore diameter, Å | Surface area, m²/g | Pore volume cm³/g |
| ZIF-8 | — | 3.4 | * | 11.6 | 1,947 | 0.663 |
| ZIF-11 | 3.0 | 3.0 | * | 14.6 | 1,676 | 0.582 |

All calculations were based on the Free Volume routine of CERIUS² software (Version 4.2; MatSci; Analysis, Inc, San Diego; probe radius 1.4 Å, medium grid) and on the single crystal x-ray structures of ZIF-8 and -11 with guests removed and disorder effects averaged.
*The aperture sizes of the 4-rings in both ZIF-S and -11 are negligible.

Thermal gravimetric analysis (TGA) performed on as-synthesized ZIF-8 and -11 revealed these compounds' thermal stability. The TGA trace for ZIF-8 showed a gradual weight-loss step of 28.3% (25-450° C.), corresponding to partial loss of guest species [1 N,N-dimethylformamide (DMF) and 3 $H_2O$; calcd. 35.9%], followed by a plateau (450-550° C.). More impressively, the TGA trace for ZIF-11 revealed a sharp weight-loss step of 22.8% (25-250° C.), corresponding to the escape of all N,Ndiethylformamide (DEF) solvent molecules trapped in the pores (0.9 DEF; calcd. 23.3%), despite the fact that DEF is actually much larger than the aperture of ZIF-11 in size. The TGA trace of ZIF-11 also showed a long plateau in the temperature range 250-550° C., indicating its high thermal stability in the absence of guest molecules. The guests in ZIF-8 and -11 were released without damaging the frameworks, as evidenced by the coincidence of the powder x-ray diffraction (PXRD) patterns of a ZIF-8 sample and a ZIF-11 sample heated to and held at 500 and 300° C., respectively, in $N_2$ atmosphere with the PXRD patterns simulated from single crystal structures. Such high thermal stability of ZIFs (up to 550° C. in $N_2$) is well beyond that of the permanently porous cubic structure of MOF-5 (decomposes at 450° C. in $N_2$), only matched by very few MOFs having relatively dense structures.

The amide guests included in as-synthesized ZIF-8 and -11 could be more readily removed by solvent-exchange. The thermogravimetric behavior of ZIF-8 and -11 were significantly simplified after they were immersed in organic solvents, such as methanol. To remove the guest species from the frameworks and prepare the evacuated forms of ZIF-8 and -11 for gas-sorption analysis, the as-synthesized ZIF samples were immersed in methanol at ambient temperature for 48 hours, and evacuated at ambient temperature for 5 h, then at an elevated temperature (300° C. for ZIF-8; 180° C. for ZIF-11) for 2 h. ZIF samples thus obtained were optimally evacuated, as evidenced by their well maintained PXRD patterns and the long plateau (25-550° C.) in their TGA traces.

Figure 2:
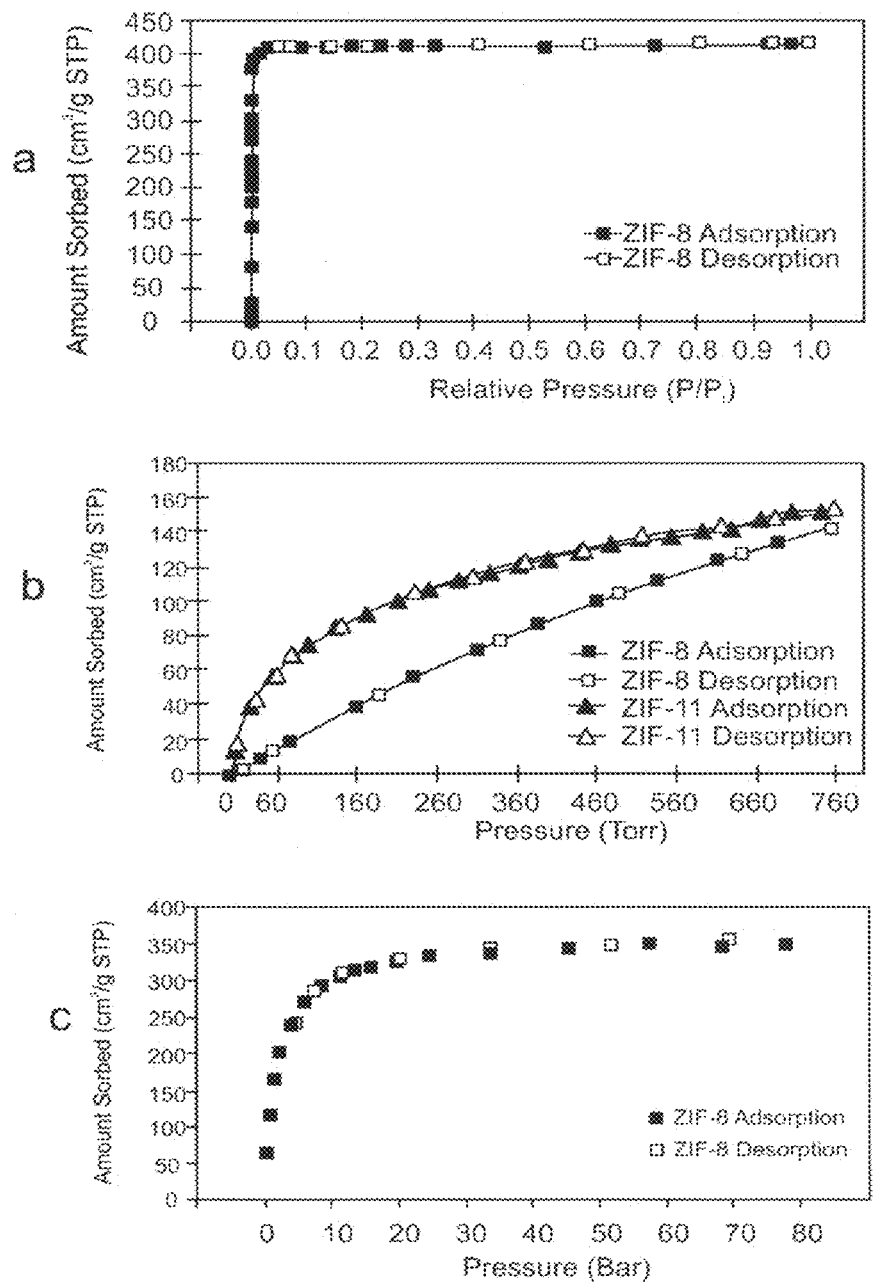
FIG. 2A-C shows the gas-sorption isotherms for prototypical ZIFs. (a) Nitrogen isotherm at 77 K for ZIF-8 sod. (b) Hydrogen isotherms at 77 K for ZIF-8 sod and ZIF-11 rho. (c) High-pressure hydrogen isotherm at 77 K for ZIF-8 sod.

The architectural rigidity and consequently the permanent porosity of evacuated ZIF-8 and -11 were unequivocally proven by gas-sorption analysis. Type I nitrogen sorption isotherm behavior was observed for ZIF-8 (FIG. 2a), which reveals its microporous nature. Apparent surface areas of 1,810 m²/g (Langmuir model) and 1,630 m²/g [Brunauer-Emmett-Teller (BET) model] for ZIF-8 were obtained by using the data points on the adsorption branch in the range of $P/P_0$=0.01-0.10, and a micropore volume of 0.636 cm³/g for ZIF-8 was obtained based on a single data point at $P/P_0$=0.10. The experimental surface area and micropore volume values of ZIF-8 fit well with the predictions based on its single crystal structure (Table 2). These surface areas surpass the highest values reported for zeolites and ordered mesoporous silica-type materials. Conversely, ZIF-11 was nonporous to nitrogen because its aperture size (3.0 Å) was smaller than the kinetic diameter of nitrogen (3.6 Å); however, it was able to take up hydrogen. Both ZIF-8 and -11 showed reversible hydrogen sorption behavior (FIG. 2b). Interestingly, the initial hydrogen uptake of ZIF-11 was much higher than that of ZIF-8, because of its unique cage interior, which is composed of protruding benzene side rings of the PhIM links around which favorable hydrogen sorption sites may be generated. However, ZIF-8 was similar to ZIF-11 in hydrogen uptake when the adsorbate pressure approached 1 atm [145 cm$^3$/g at standard temperature and pressure (STP)] or 12.9 mg/g for ZIF-8; 154 cm$^3$/g STP or 13.7 mg/g for ZIF-11). This result is expected because ZIF-8 has higher surface area and pore volume (Table 2). The ultimate hydrogen capacity of ZIF-8 was uncovered in a high-pressure (up to 80 bar) hydrogen sorption measurement at 77 K on a large batch of evacuated ZIF-8 (0.724 g), which showed 350 cm$^3$/g STP (31 mg/g) at 55 bar. The hydrogen uptake of ZIF-8 and its Langmuir surface area (1,810 m$^2$/g) fit well in a linear relationship proposed recently based on our high-pressure hydrogen sorption measurements on a series of MOFs with high surface areas.

Figure 3:
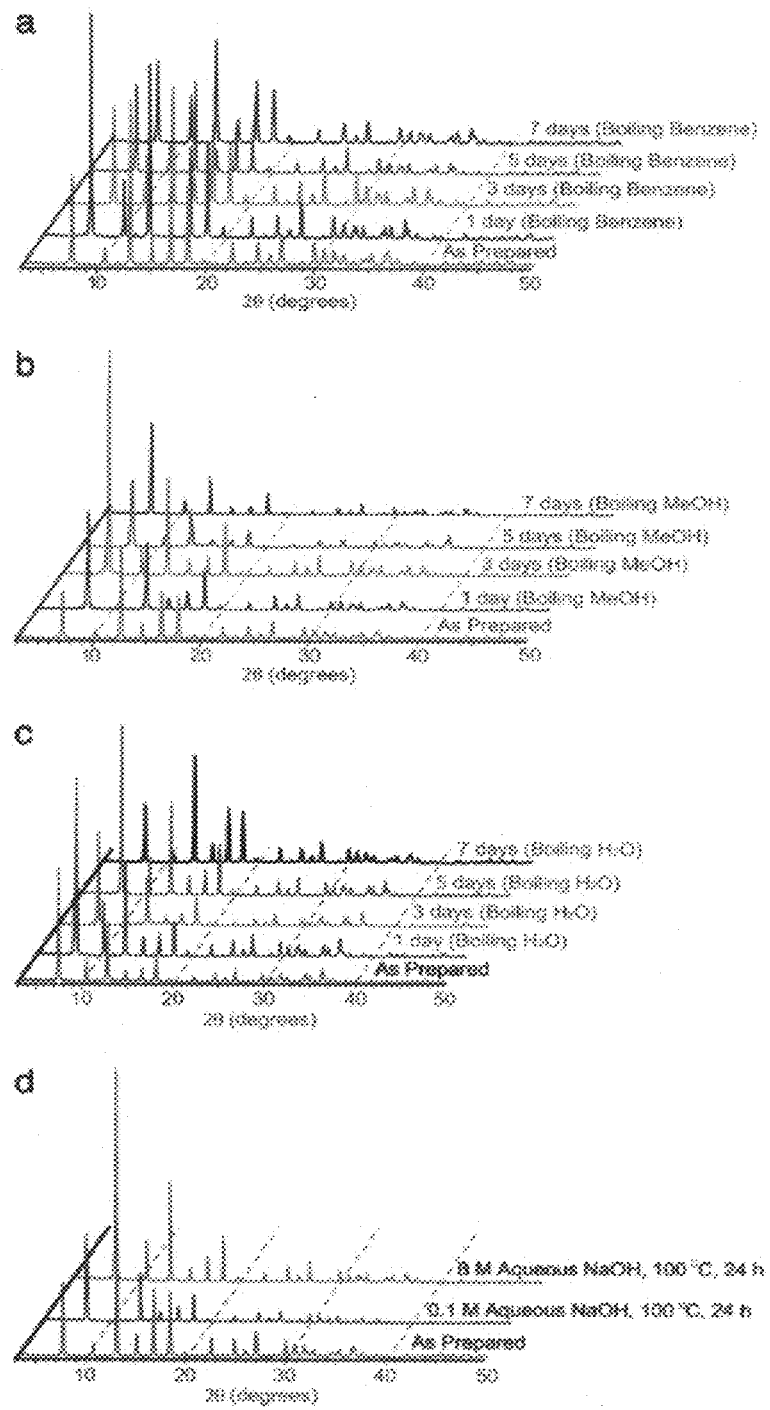
FIG. 3A-D shows the PXRD patterns for ZIF-8 samples measured during chemical stability tests. (a) In refluxing benzene at 80° C. for up to 7 days. (b) In refluxing methanol at 65° C. for up to 7 days. (c) In refluxing water at 100° C. for up to 7 days. (d) In refluxing aqueous NaOH solution for up to 1 day.

The chemical stability of ZIFs was examined by suspending samples of ZIF-8 and -11 in boiling benzene, methanol, water, and aqueous sodiumhydroxide (FIG. 3), conditions that reflect extreme operational parameters of typical industrial chemical processes. ZIF samples were immersed in the desired solvent for 1-7 days at ambient temperature, 50° C., and at the boiling point of each medium. During this process, samples were periodically observed under an optical microscope and found to be insoluble under each of these conditions. PXRD patterns collected for each sample at designated intervals showed that the solid samples of ZIF-8 and -11 maintained their full crystallinity and were impervious to the boiling organic solvents for 7 days. Both ZIFs sustained their structures in water at 50° C. for 7 days. ZIF-8 thus was further probed and shown to be unchanged for up to 24 hours in 0.1 and 8 M aqueous sodium hydroxide at 100° C. The hydrothermal stability of ZIF-8 is superior to those of original MCM and SBA types of ordered mesoporous silica, even rivaling the ultrastable derivatives of these materials.

Typical ZIF Synthesis. Benzimidazole, 2-methylimidazole, Indium nitrate pentahydrate and cobalt nitrate hexahydrate were purchased from the Aldrich Chemical Co. and imidazole, N,N-dimethylformamaide (DMF), N-methylpyrrolidinone (NMP) were purchased from the Fisher Scientific International Inc. N,N-diethylformamide (DEF) was obtained from BASF Corporation. Zinc nitrate tetrahydrate was purchased from the EM Science. All starting materials were used without further purifications. All experimental operations were performed in air. (ZIF syntheses are exemplified here by the synthesis of ZIF-8) A solid mixture of zinc nitrate tetrahydrate $Zn(NO_3)_2.4H_2O$ (0.210 g, 8.03×10$^{-4}$ mol) and 2-methylimidazole (H-MeIM) (0.060 g, 7.31×10$^{-4}$ mol) was dissolved in 18 ml of DMF in a 20-ml vial. The vial was capped and heated at a rate of 5° C./min to 140° C. in a programmable oven and held at this temperature for 24 h, then cooled at a rate of 0.4° C./min to room temperature. After removal of mother liquor from the mixture, chloroform (20 ml) was added to the vial. Colorless polyhedral crystals were collected from the upper layer, washed with DMF (10 ml×3), and dried in air for 10 min (yield: 0.032 g, 25% based on H-MeIM). The product was formulated by using elemental microanalysis as $Zn(MeIM)_2.(DMF).(H_2O)_3$ ($C_{11}H_{23}N_5O_4Zn$; Calcd. C, 37.25; H, 6.54; N, 19.74. Found. C, 37.69; H, 5.22; N, 19.58). The purity of ZIF-8 product has also been confirmed by PXRD analysis.

Single Crystal X-Ray Diffraction Studies. All of the intensity data were collected on a SMART APEX CCD diffractometer (Bruker-AXS, Madison, Wis.) with graphite monochromated MoKα (λ=0.71073 Å) radiation. Structures were solved by direct methods, and successive difference Fourier syntheses were made with the SHELXTL software package (Bruker-AXS). Crystal data are as follows: ZIF-1 (crb, monoclinc form): monoclinic, space group P2$_1$/n; a=9.740, b=15.266, c=14.936 Å, β=98.62°; V=2195.8 Å$^3$, R1=0.0423. ZIF-2 (crb, orthorhombic form): orthorhombic, space group Pbca; a=9.679, b=c=24.114 Å; V=5707 Å$^3$, R=0.0591. ZIF-3 (dft): tetragonal, space group P4$_2$/mnm; a=b=18.970, c=16.740 Å; V=6024.3 (1) Å$^3$, R1=0.0610. ZIF-4 (cag): orthorhombic, space group Pbca; a=b=15.395, c=18.426 Å; V=4342.2 Å$^3$, R1=0.0406. ZIF-5 (gar): cubic, space group Ia3d; a$_o$=21.9619 Å; V=0592.8 Å$^3$, R1=0.0191. ZIF-6 (gis): tetragonal, space group I4$_1$/amd; a=b=18.515, c=20.245 Å; V=6940.2 Å$^3$, R1=0.0642. ZIF-7: [sod-Zn(II)-PhIM form]: hexagonal, space group R3; a=b=22.989, c=15.763 Å; V=7214 Å$^3$, R1=0.0707. ZIF-8: [sod-Zn(II)-MeIM form]: cubic, space group I4/3m; a$_o$=16.9910 Å; V=4905.2 Å$^3$, R1=0.0314. ZIF-9 [sod-Co(II)-PhIM form]: hexagonal, space group R3; a=b=22.9437, c=15.747 Å; V=7178.8 Å$^3$, R1=0.0979. ZIF-10 (mer): tetragonal, space group I4/mmm; a=b=27.0608, c=19.406 Å; V=14211 Å$^3$, R1=0.0636. ZIF-11 [rho-Zn(II)-PhIM form]: cubic, space group Pm3m; a$_o$=28.7595 Å; V=23787.2 Å, R1=0.0787. ZIF-12 [rho-Co(II)-PhIM form]: cubic, space group Pm3m; a$_o$=28.7595 Å; V=23787.2 Å$^3$, R1=0.1064. Atomic coordinates are available for download from the Cambridge Crystallographic Data Centre by citing deposition numbers 602535 (ZIF-1), 602536 (ZIF-2), 602537 (ZIF-3), 602538 (ZIF-4), 602539 (ZIF-5), 602540 (ZIF-6), 602541 (ZIF-7), 602542 (ZIF-8), 602543 (ZIF-9), 602544 (ZIF-10), 602545 (ZIF-11), 602546 (ZIF-12).

PXRD Studies. Powder x-ray data were collected by using a D8-Advance θ-2θ diffractometer (Bruker) in reflectance Bragg-Brentano geometry employing Ni-filtered CuKα line focused radiation at 1,600 W (40 kV, 40 mA) power and equipped with a Na(Tl) scintillation detector fitted with a 0.2-mm radiation entrance slit. Samples were mounted on zero background sample holders by dropping powders from a wide-blade spatula and then leveling the sample surface with a razor blade. All samples were ground before PXRD experiment.

TGA. All samples were run on a Q-500 series thermal gravimetric analyzer (TA Instruments, New Castle, Del.) with samples held in platinum pans in a continuous-flow nitrogen atmosphere. Samples were heated at a constant rate of 5° C./min during all TGA experiments.

Gas-Sorption Measurements. All low-pressure gas-sorption experiments (up to 1 atm) were performed on a Autosorb-1C automatic volumetric instrument (Quantachrome, Boynton Beach, Fla.). High-pressure hydrogen sorption experiments (up to 80 bar) were performed on a HPA-100 volumetric instrument (VTI, Hialeah, Fla.) equipped with a home-made liquid nitrogen cooling system to sustain a constant coolant bath level. The compressibility factors of high-pressure gases were determined by using the REFPROP program [Version 7.0; National Institute of Standards and Technology (NIST), Gaithersburg, Md.] and the NIST Standard Reference Data Base 23. Before gas-sorption analysis, ZIF-8 and -11 samples were immersed in methanol at ambient temperature for 48 hours and evacuated at ambient temperature for 5 h, then at an elevated temperature (300° C. for ZIF-8, 180° C. for ZIF-11) for 2 h.

(ZIF-1 crb): Zn(IM)2.(Me2NH). A solid mixture of zinc nitrate tetrahydrate Zn(NO3)2.4H2O (0.09 g, 3.44×10$^{-4}$ mol) and imidazole (H-IM) (0.15 g, 2.20×10$^{-3}$ mol) was dissolved in 18 mL DMF in a 20-mL vial. The vial was capped and heated for 24 hours in a 85° C. isothermal oven. The vial was then removed from the oven and allowed to cool to room temperature naturally. Colorless cubic crystals of ZIF-1 thus produced were washed with DMF (3 mL×3) and dried in air (10 min) (yield: 0.014 g, 17% based on zinc nitrate tetrahydrate). Elemental analysis C8H13N5Zn=Zn(IM)2.(Me2NH): Calcd. C, 39.28; H, 5.36; N, 28.65. Found C, 39.47; H, 4.39; N, 27.13. FT-IR: (KBr 4000-400 cm$^{-1}$): 3445 (br), 3103(w), 2935(w), 2385(w), 2355(w), 1647(s), 1499 (m), 1418(w), 1403(w), 1321(w), 1291(w), 1245(w), 1184 (w), 1087(s), 1026(w), 985(w), 960(m), 837(w), 761(m), 680 (m), 603(w).

(ZIF-3 dft): Zn(IM)2. A solid mixture of zinc nitrate tetrahydrate Zn(NO3)2.4H2O (0.010 g, 3.82×10$^{-5}$mol) and imidazole (H-IM) (0.030 g, 4.41×10$^{-4}$mol) was added in a 4-mL vial and dissolved in a mixed solvent of DMF (2 mL) and NMP (1 mL). The vial was capped and heated for 4 d in a 85° C. isothermal oven. The vial was then removed from the oven and allowed to cool to room temperature naturally. Several prism-shaped crystals formed at the bottom of the vial along with some white powder-like precipitate. The crystals of ZIF-3 were collected manually for single crystal X-ray structure determination.

(ZIF-4 cag): Zn(IM)2.(DMF)(H2O) A solid mixture of zinc nitrate tetrahydrate Zn(NO3)2.4H2O (0.040 g, 1.53×10$^{-4}$mol) and imidazole (H-IM) (0.030 g, 4.41×10$^{-4}$mol) was dissolved in 3 mL DMF in a 4-mL vial. The vial was capped and heated at a rate of 5° C./min to 130° C. in a programmable oven, held at this temperature for 48 hours, then cooled at a rate of 0.4° C./min to room temperature. Colorless rhombohedral crystals of ZIF-4 thus produced were washed with DMF (3 mL×3) and dried in the air (10 min) (yield: 0.021 g, 47% based on zinc nitrate tetrahydrate). Elemental analysis: C9H15N5O2Zn=Zn(IM)2.(DMF)(H2O): Calcd. C, 37.19; H, 5.20; N, 24.10. Found C, 38.02; H, 4.14; N, 26.74. FT-IR: (KBr 4000-400 cm$^{-1}$): 3427(br), 3111(w), 2926(w), 2856 (w), 1688(m), 1612(br), 1502(m), 1392(w), 1282(w), 1247 (w), 1176(w), 1091(s), 986(w), 961(m), 846(w), 770(m), 680 (m), 490(br).

(ZIF-5 gar): In2Zn3(IM)12 Indium nitrate pentahydrate, In(NO3)3.5H2O (0.156 g, 4.0×10$^{-4}$mol), zinc nitrate tetrahydrate Zn(NO3)2.4H2O (0.026 g, 1.0×10$^{-4}$mmol) and imidazole (H-IM) (0.136 g, 2×10$^{-3}$mol) were dissolved in a mixed solvent of DEF/nbutanol (4 mL/2 mL,). After the addition of small amount of tetraethylammonium hydroxide (35% aqueous solution), the mixture was transferred into a Teflon-lined Parr stainless steel vessel (23 mL) and heated at 150° C. for 72 hours under autogenous pressure. Pale-yellow crystals thus produced were washed with ethanol and dried in air (yield: 70%, based on zinc nitrate tetrahydrate). Elemental analysis: C36H36N24Zn3In2=In2Zn3(IM)12: Calcd. C, 35.14; H, 2.95; N, 27.32. Found C, 33.97; H, 2.82; N, 26.22. Zn/In molar ratio: Calcd, 1.50, Found, 1.52. FT-IR (KBr4000-400 cm$^{-1}$): 3433 (br), 3132 (m), 3112 (m), 2601 (w), 2524 (w), 1697 (m), 1605 (m).

ZIF-5 was formulated as In2Zn3(IM)12 based on single crystal X-ray structure. We found the high In/Zn ratio employed in the synthesis was important to the formation of ZIF-5. However, high Indium content also resulted in small amount of amorphous In-rich impurities (indium oxide or indium hydroxide) as evidenced by the electron microprobe analysis (EMPA) result of the "bright spots" on crystal surfaces. The content of such impurities was calculated to be 3.3%-4.4% based on the elemental analysis results of C, H, N for the bulk product. Nevertheless, the elemental analysis result of Zn/In molar ratio for a small number of the clearest crystals manually separated from the bulk product match the proposed formula well.

(ZIF-7 sod): Zn(PhIM)2.(H2O)3. A solid mixture of zinc nitrate tetrahydrate Zn(NO3)2.4H2O (0.030 g, 1.15×10$^{-4}$mol) and benzimidazole (H-PhIM) (0.010 g, 8.46× 10$^{-5}$mol) was dissolved in 3 mL DMF in a 4-mL vial. The vial was capped and heated at a rate of 5° C./min to 130° C. in a programmable oven, held at this temperature for 48 hours, then cooled at a rate of 0.4° C./min to room temperature. After removal of mother liquor from the mixture, chloroform (3 mL) was added to the vial. Colorless cubic crystals of ZIF-7 were collected from the upper layer, washed with DMF (3 mL×3) and dried in air (10 min) (yield: 0.015 g, 37% based on H-PhIM). Elemental analysis C14H16N4O3Zn=Zn(IM)2.(H2O)3: Calcd. C, 47.54; H, 4.56; N, 15.84. Found. C, 46.95; H, 3.57; N, 16.40. FT-IR: (KBr 4000-400 cm$^{-1}$): 3450(br), 3063(w), 2930(w), 1678(s), 1622(w), 1479(s), 1387(m), 1306(m), 1286(m), 1245(s), 1209(w), 1189(m), 1123(m), 1097(m), 1011(m), 914(m), 781(m), 746(s), 654(m), 476(m), 435(m).

(ZIF-8 sod): Zn(MeIM)2.(DMF).(H2O)3. A solid mixture of zinc nitrate tetrahydrate Zn(NO3)2.4H2O (0.210 g, 8.03× 10$^{-4}$mol) and 2-methylimidazole (H-MeIM) (0.060 g, 7.31× 10$^{-4}$mol) was dissolved in 18 mL DMF in a 20-mL vial. The vial was capped and heated at a rate of 5° C./min to 140° C. in a programmable oven, held at this temperature for 24 hours, then cooled at a rate of 0.4° C./min to room temperature. After removal of mother liquid from the mixture, chloroform (20 mL) was added to the vial. Colorless polyhedral crystals of the product were collected from the upper layer, washed with DMF (10 mL×3) and dried in air (10 min) (yield: 0.032 g, 25% based on H-MeIM). Elemental analysis. C11H23N5O4Zn=Zn(MeIM)2.(DMF).(H2O)3 Calcd. C, 37.25; H, 6.54; N, 19.74. Found. C, 37.69; H, 5.22; N, 19.58 FT-IR: (KBr 4000-400 cm$^{-1}$): 3460(w), 3134(w), 2930(m), 2854(w), 2767(w), 2487(w), 2457(w), 1693(s), 1591(w), 1459(s), 1428(s), 1392(m), 131 1(s), 1265(w), 1189(m), 1148(s), 1091(m), 1000(m), 960(w), 766(s), 695(m), 664(m), 425(s).

(ZIF-9 sod): Co(PhIM)2.(DMF)(H2O). A solid mixture of cobalt nitrate hexahydrate Co(NO3)2.6H2O (0.210 g, 7.21× 10$^{-4}$mol) and benzimidazole (H-PhIM) (0.060 g, 5.08×10$^{-4}$mol) was dissolved in 18 mL DMF in a 20-mL vial. The vial was capped and heated at a rate of 5° C./min to 130° C. in a programmable oven, held at this temperature for 48 hours, then cooled at a rate of 0.4° C./min to room temperature. Purple cubic crystals thus produced were washed with DMF (3 mL×3) and dried in air (10 min) (yield: 0.030 g, 30% based on H-PhIM). Elemental analysis C17H19N5O2Co=Co(PhIM)2.(DMF)(H2O) Calcd. C, 53.13; H, 4.98; N, 18.22. Found. C, 52.82; H, 4.25; N, 18.23. FT-IR: (KBr 4000-400 cm$^{-1}$): 3442(br), 3071(w), 2926(w), 1678(s), 1612(w), 1467(s), 1387(w), 1302(w), 1287(m), 1242(s), 1206(w), 1186(w), 1126(w), 1096(w), 1011(w), 916(w), 780(w), 750(s), 660(w), 600(br), 560(w), 475(w).

(ZIF-10 mer): Zn(IM)2. A solid mixture of zinc nitrate tetrahydrate Zn(NO3)2.4H2O (0.010 g, 3.82×10$^{-5}$mol) and imidazole (H-IM) (0.030 g, 4.41×10$^{-4}$mol) was dissolved in 3 mL DMF in a 4-mL vial. The vial was capped and heated for 4 d in an isothermal oven at 85° C. The reaction mixture was then allowed to cool to room temperature naturally. Several block-shape crystals of ZIF-10 formed on the wall and bottom, and were separated by hand and collected for single crystal X-ray structure determination.

(ZIF-11 rho) Zn(PhIM)2.(DEF)0.9. A solid mixture of zinc nitrate tetrahydrate Zn(NO3)2.4H2O (0.60 g, 2.3×10$^{-3}$ mol) and benzimidazole (H-PhIM) (4.2 g, 3.5×10$^{-2}$ mol) was dissolved in 360 mL DEF in a 500-mL wide-mouth glass jar. The capped jar was heated for 4 d in an isothermal oven at 100° C. The jar was then removed from the oven, and allowed to cool to room temperature naturally. Cubic colorless crystals formed on the walls of the jar along with a crystalline powder at the bottom. Although the powder and crystals were proven to be the same phase by powder X-ray diffraction, only the crystals on the wall were used for bulk characterizations. The powder and mother liquor was removed by repeating the cycle of decanting, washing with DMF and sonicating several times. Colorless crystals of ZIF-11 were collected by filtration, washed with DMF (200 mL×2) and dried in the air (30 min) (yield: 0.21 g, 23% based on Zn(NO3)2.4H2O). Elemental analysis C18H21N5O1Zn1=Zn(PhIM)2.(DEF) 0.9 Calcd. C, 56.94; H, 5.10; N, 17.59. Found: C, 55.69; H, 4.64; N, 17.58. FT-IR (KBr, 4000-400 cm$^{-1}$): 3452(br), 3091 (w), 3056(w), 2981(w), 2941(w), 2876(w), 2781(w), 2525 (w), 1939(w), 1903(w), 1783(w), 1668(s), 1618(m), 1467(s), 1397(w), 1367(w), 1307(m), 1282(m), 1247(m), 1212(w), 1187(m), 1121(m), 1001(m), 911(m), 826(w), 771(m), 751(s), 645(m), 553(m), 520(m), 475(m).

(ZIF-12 rho): Co(PhIM)2. A solid mixture of cobalt nitrate hexahydrate Co(NO3)2.6H2O (0.010 g, 3.44×10$^{-5}$ mol) and benzimidazole (H-PhIM) (0.030 g, 2.54×10$^{-5}$ mol) was dissolved in 3 mL DEF in a 4-mL vial. The capped vial was heated for 2 d in an isothermal oven at 130° C. The reaction mixture was then allowed to cool to room temperature naturally. Several cubic crystals of ZIF-12 formed at the bottom and on the wall of the vial, and they were collected for single crystal X-ray structure determination.

ZIF-2 and ZIF-6 were discovered by combinatorial experimentation utilizing a 96-well glass plate (Zinsser, maximum 0.300 mL reaction mixture per well) as reaction vessel. A 0.150 M solution of imidazole in DMF and a 0.075M solution of Zn(NO3)2.4H2O in DMF were used as stock solutions. After the 96-well glass plate was loaded with mixtures of stock solutions dispensed by a programmed liquid handler (Gilson, model 215), it was covered with a PTFE sheet, sealed by fastening the sheet with a metal clamp, then heated in a 85° C. isothermal oven for 3 days. After reaction, the products were examined under an optical microscope and characterized by single-crystal X-ray diffraction.

(ZIF-2 crb): Zn(IM)2. 0.265 mL imidazole stock solution (0.150 M, 3.98×10$^{-4}$ mol) and 0.035 mL Zn(NO3)2.4H2O stock solution (0.075 M, 2.63×10$^{-6}$ mol). The product was in the form of small rod-shaped single crystals.

(ZIF-6 gis): Zn(IM)2. 0.257 mL imidazole stock solution (0.150 M, 3.86×10$^{-5}$ mol) and 0.043 mL Zn(NO3)2.4H2O stock solution (0.075 M, 3.23×10$^{-6}$ mol). The product was in the form of large inter-grown blocks, which could be cut into small single crystals under an optical microscope.

Figure 4:
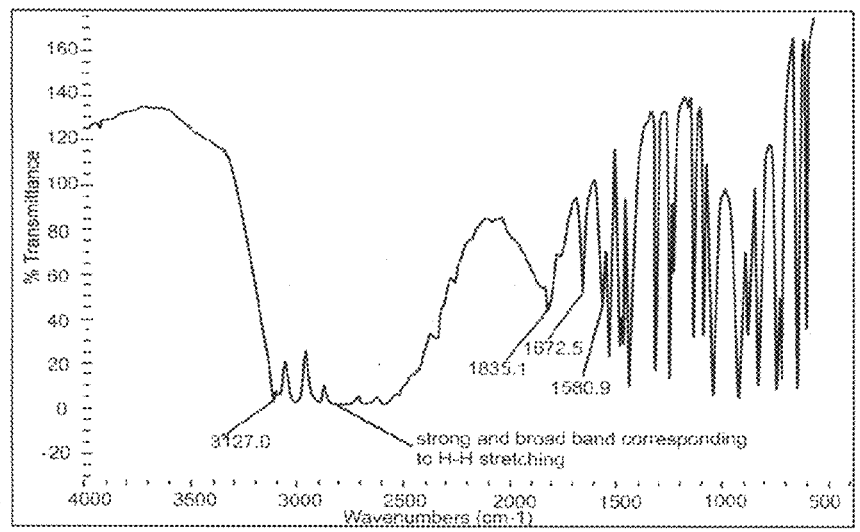
FIG. 4A-B provides the FT-IR spectra of (a) imidazole and (b) ZIF-5 (gar), In$_2$Zn$_3$(IM)$_{12}$.
Figure 4:
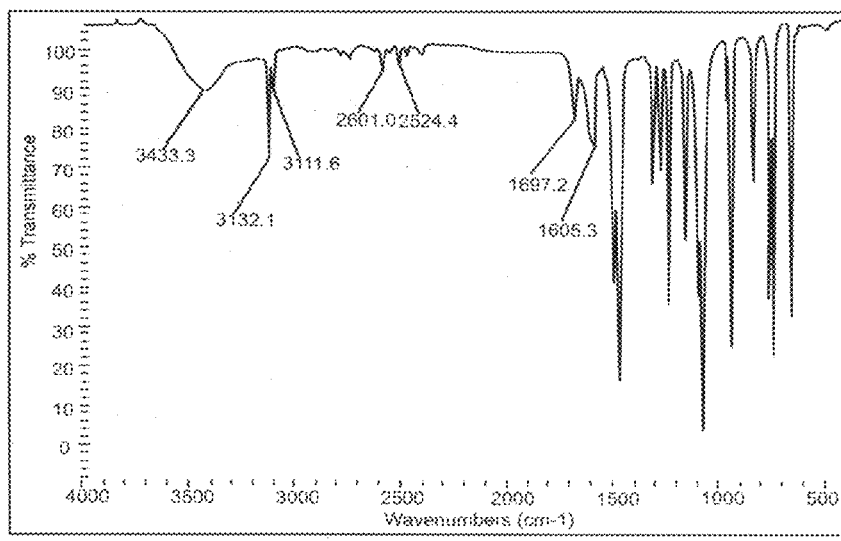
Figure 5:
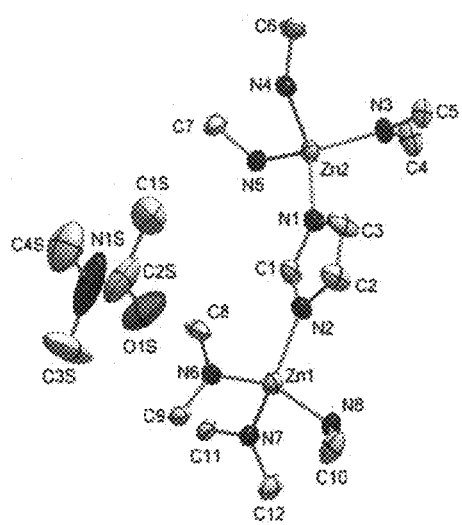
FIG. 5 is an ORTEP diagram of the Asymmetric Unit of ZIF-1 including dimethyl acetamide guest molecule.
Figure 6:
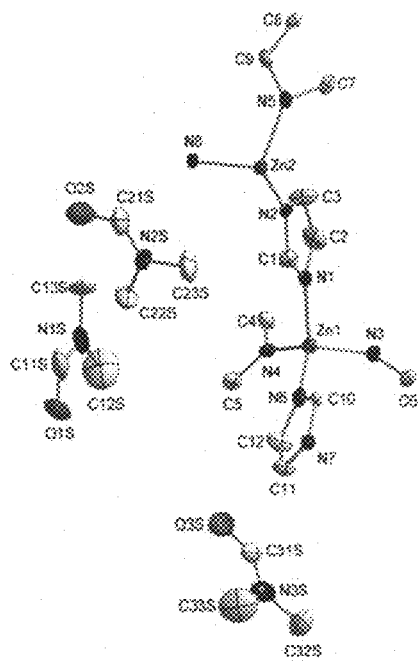
FIG. 6 is an ORTEP diagram of the asymmetric unit of ZIF-2 including guest dimethylformamide molecules. Ellipsoids are displayed at the 50% probability level.
Figure 7:
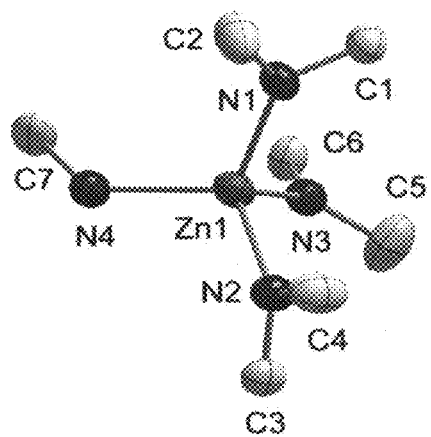
FIG. 7 is an ORTEP diagram of the asymmetric unit of ZIF-3 framework.
Figure 8:
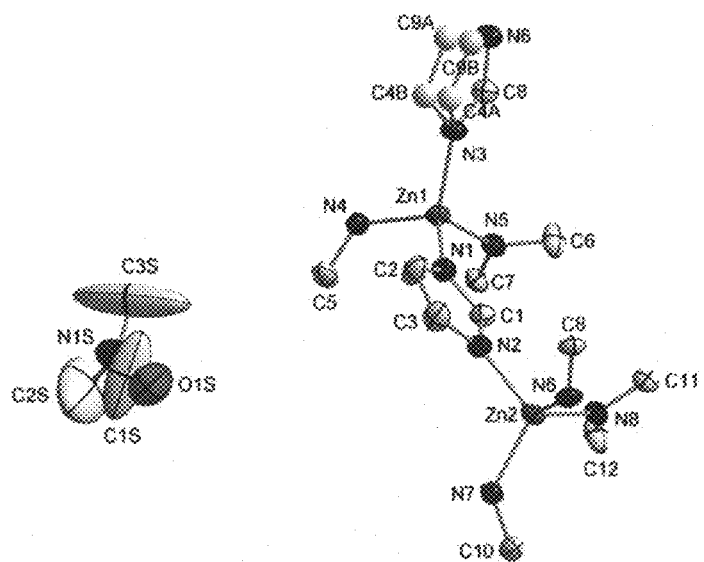
FIG. 8 is an ORTEP diagram of the asymmetric unit of ZIF-4 including guest dimethylformamide molecule.
Figure 9:
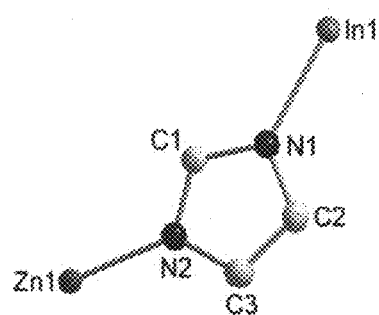
FIG. 9 is an ORTEP diagram of the asymmetric unit of the ZIF-5 framework. Ellipsoids are displayed at the 50% probability level.
Figure 10:
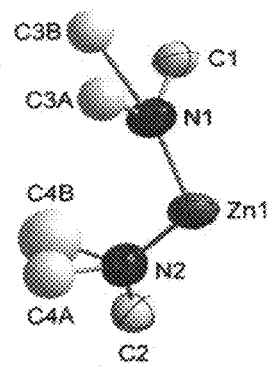
FIG. 10 is an ORTEP diagram for the asymmetric unit of the ZIF-6 framework.
Figure 11:
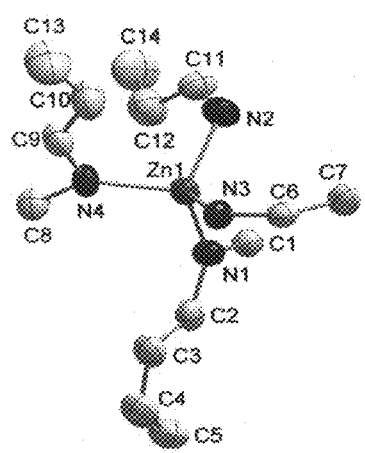
FIG. 11 is an ORTEP representative of the asymmetric unit of the ZIF-7 framework.
Figure 12:
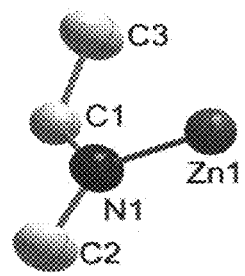
FIG. 12 is an ORTEP diagram of the asymmetric unit of the ZIF-8 framework.
Figure 13:
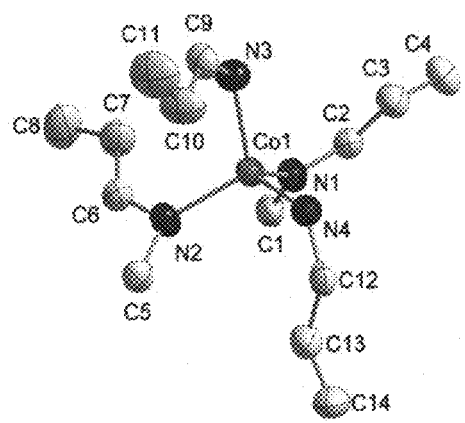
FIG. 13 is an ORTEP diagram of the asymmetric unit of the ZIF-9 framework.
Figure 14:
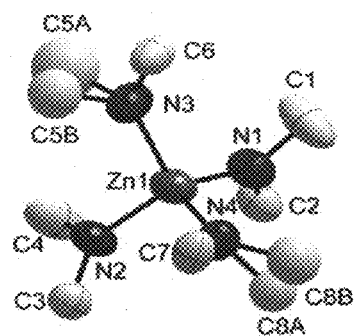
FIG. 14 is an ORTEP diagram of the asymmetric unit of ZIF-10 framework.
Figure 15:
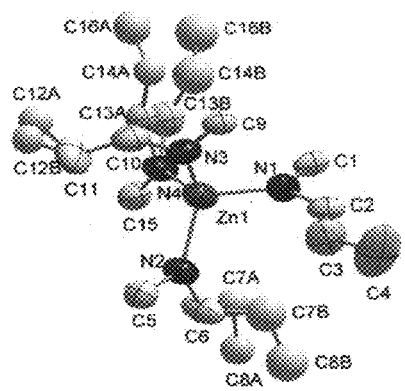
FIG. 15 is an ORTEP diagram of the asymmetric unit of the ZIF-11 framework.
Figure 16:
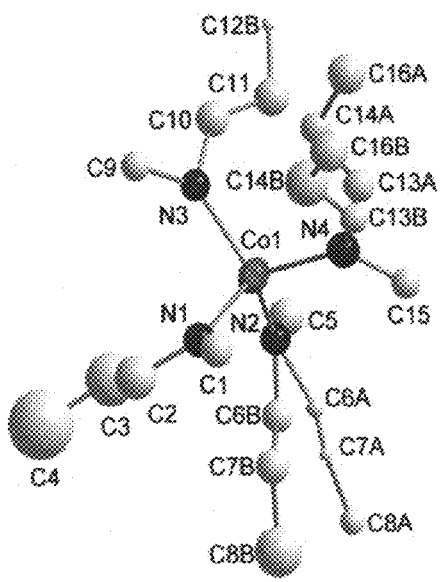
FIG. 16 is an ORTEP diagram of the asymmetric unit of ZIF-12 framework.
Figure 17:
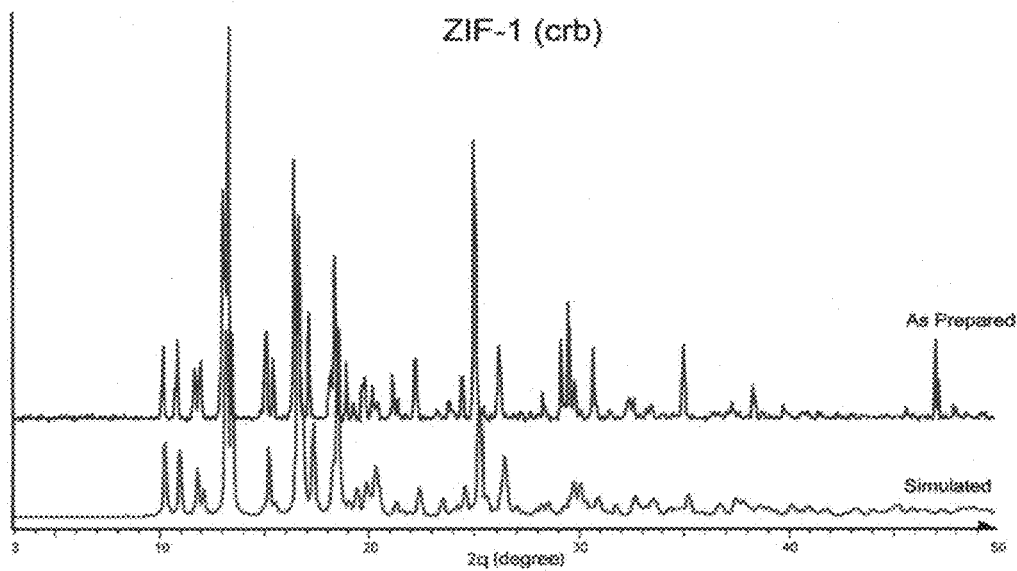
FIG. 17 shows a comparison of the experimental PXRD pattern of as-prepared ZIF-1 (top) with the one simulated from its single crystal structure (bottom). The very high degree of correspondence between the patterns indicates that the bulk material has the same structure as the single crystal.
Figure 18:
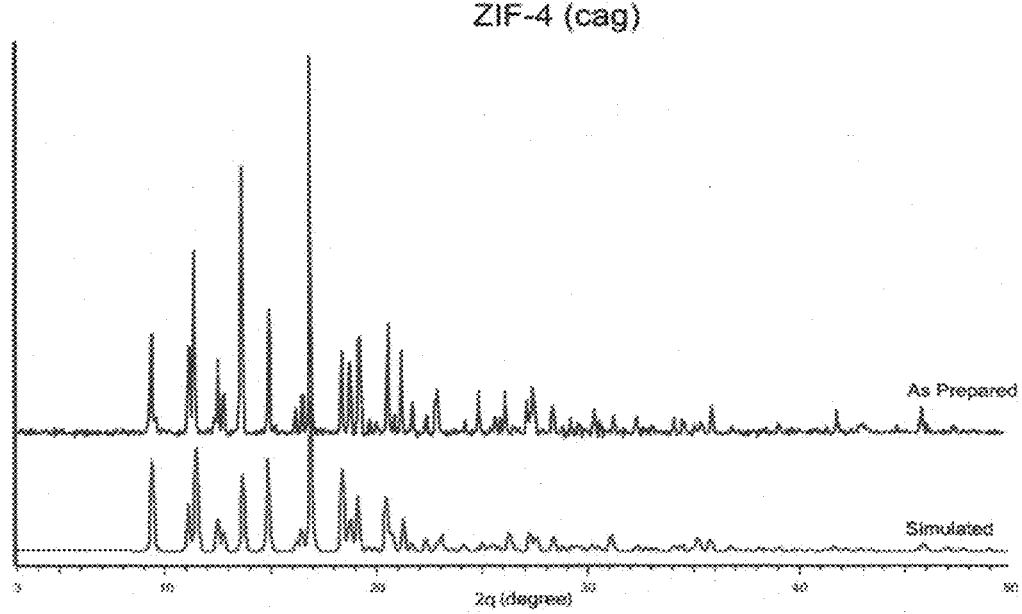
FIG. 18 shows a comparison of the experimental PXRD pattern of as-prepared ZIF-4 (top) with the one simulated from its single crystal structure (bottom). The very high degree of correspondence between the patterns indicates that the bulk material has the same structure as the single crystal.
Figure 19:
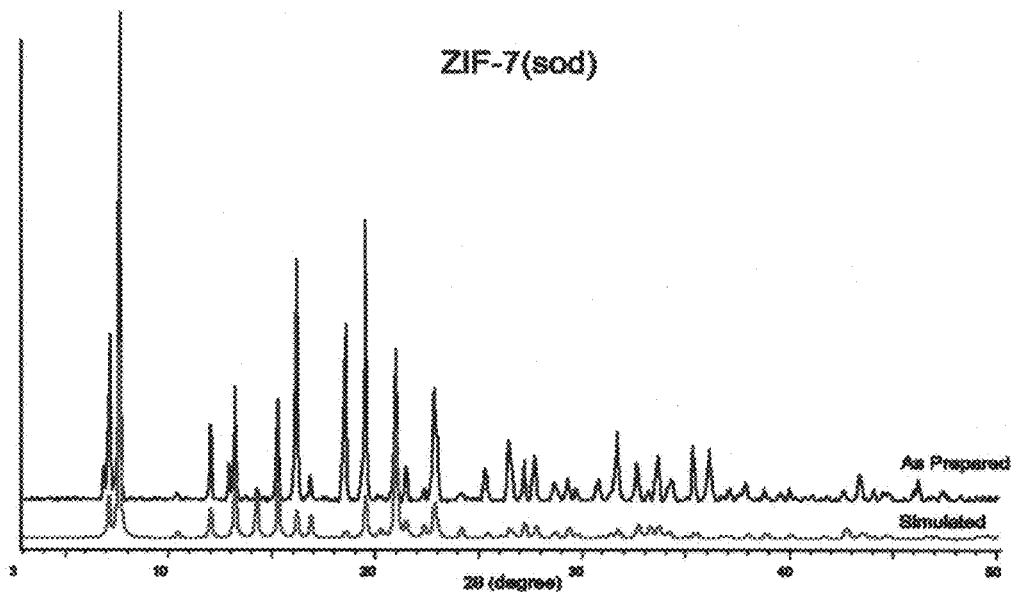
FIG. 19 shows a comparison of the experimental PXRD pattern of as-prepared ZIF-7 (top) with the one simulated from its single crystal structure (bottom). The very high degree of correspondence between the patterns indicates that the bulk material has the same structure as the single crystal.
Figure 20:
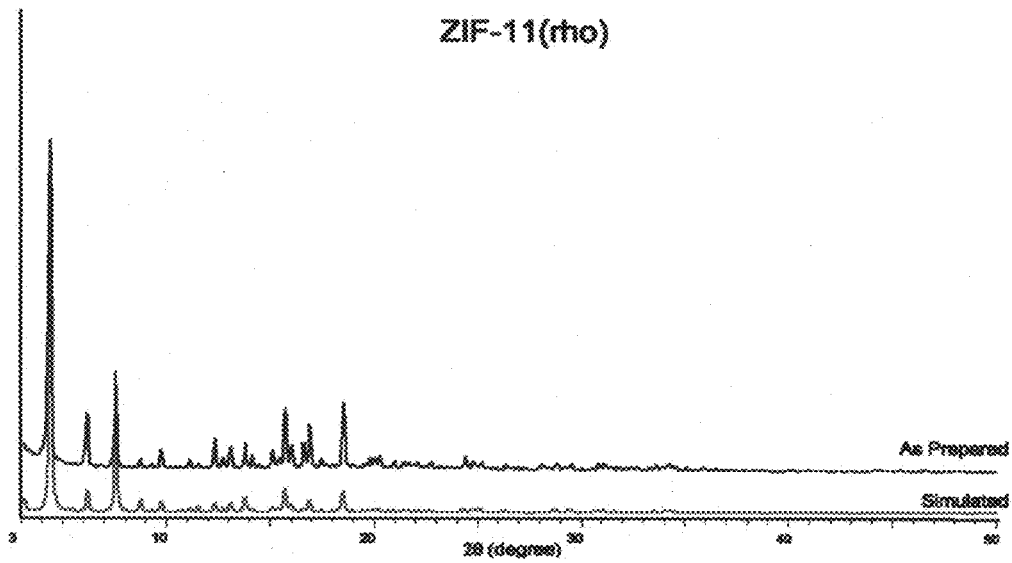
FIG. 20 shows a comparison of the experimental PXRD pattern of as-prepared ZIF-11 (top) with the one simulated from its single crystal structure (bottom). The very high degree of correspondence between the patterns indicates that the bulk material has the same structure as the single crystal.
Figure 21:
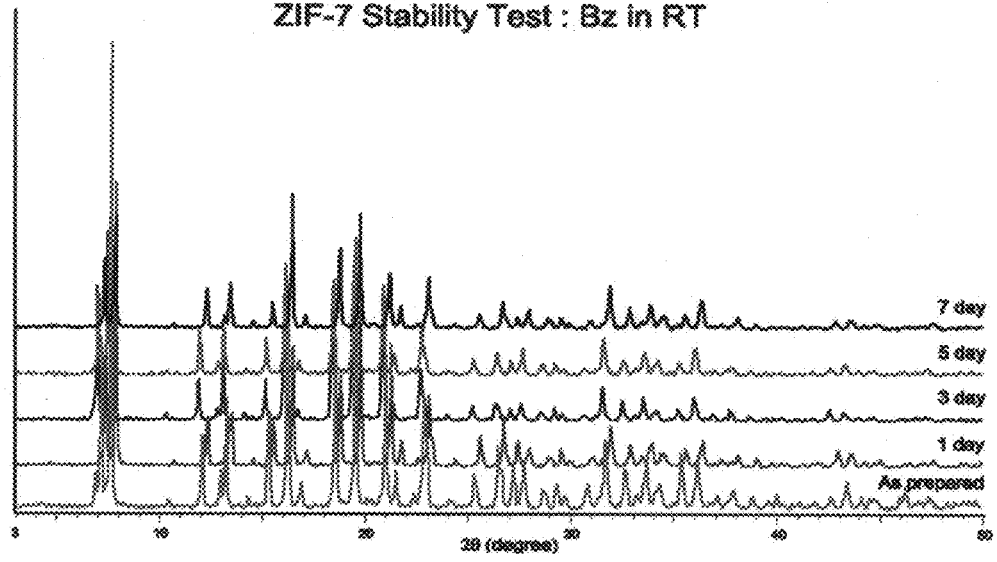
FIG. 21 shows PXRD patterns of ZIF-7 collected during stability test in benzene at room temperature. The framework structure of ZIF-7 was unchanged after 7 days.
Figure 22:
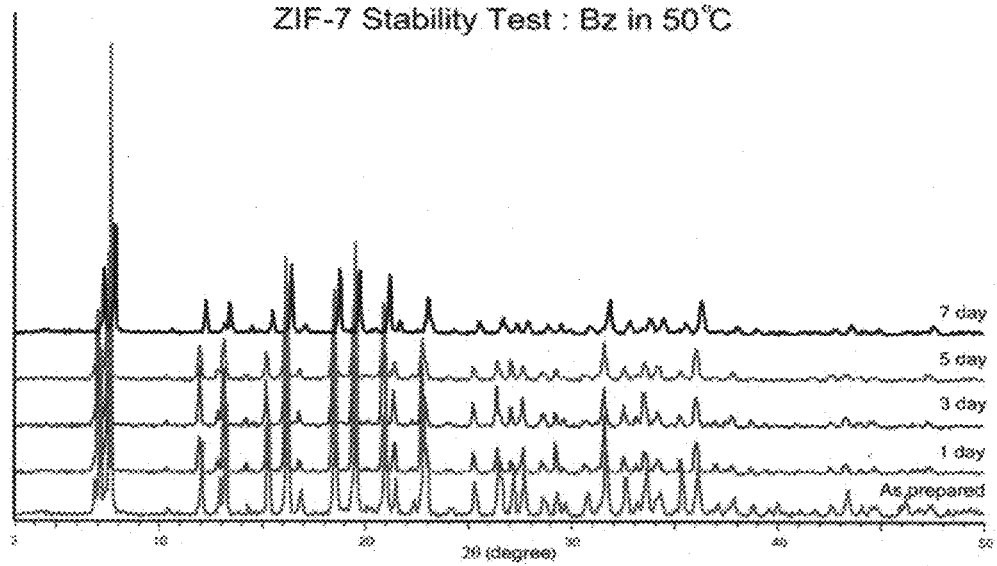
FIG. 22 shows PXRD patterns of ZIF-7 collected during stability test in benzene at 50° C. The framework structure of ZIF-7 was unchanged after 7 days.
Figure 23:
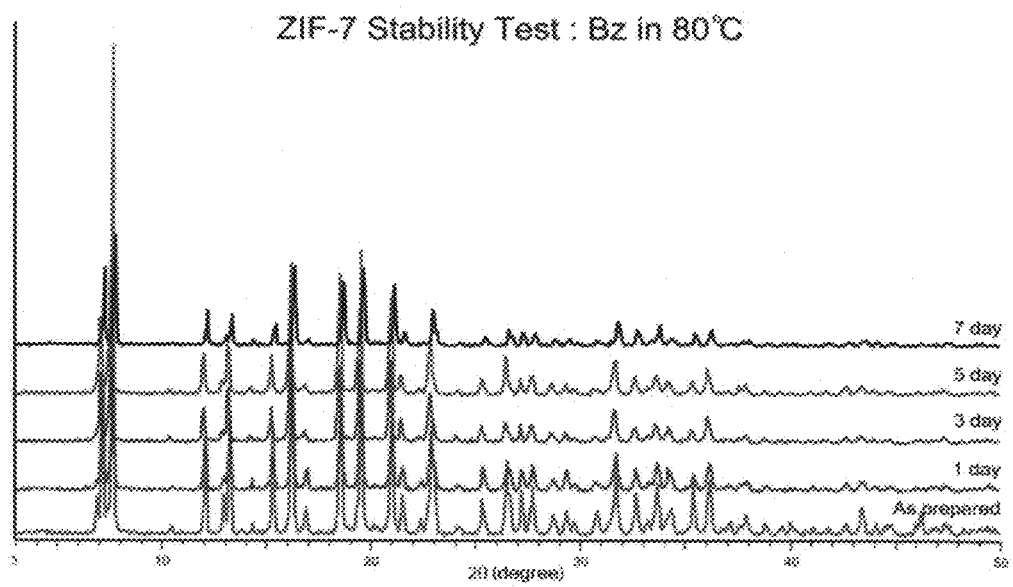
FIG. 23 shows PXRD patterns of ZIF-7 collected during stability test in benzene at 80° C. The framework structure of ZIF-7 was unchanged after 7 days.
Figure 24:
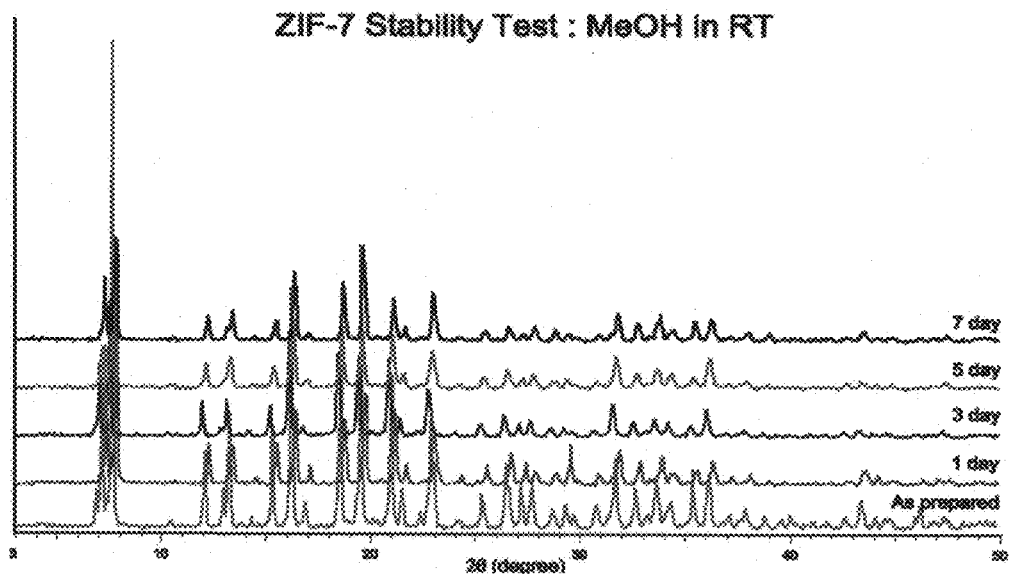
FIG. 24 shows PXRD patterns of ZIF-7 collected during stability test in methanol at room temperature. The framework structure of ZIF-7 was unchanged after 7 days.
Figure 25:
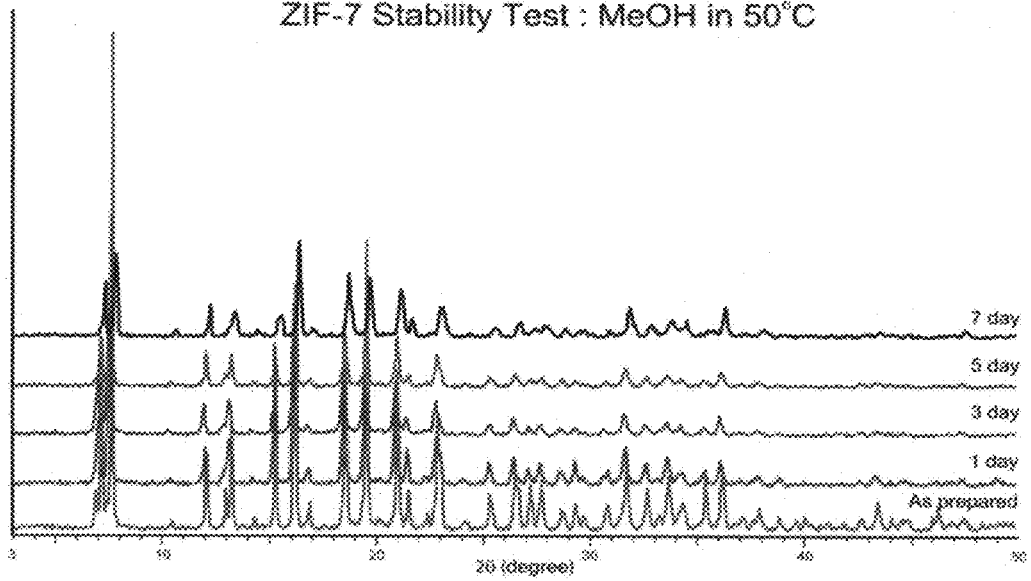
FIG. 25 shows PXRD patterns of ZIF-7 collected during stability test in methanol at 50° C. The framework structure of ZIF-7 was unchanged after 7 days.
Figure 26:
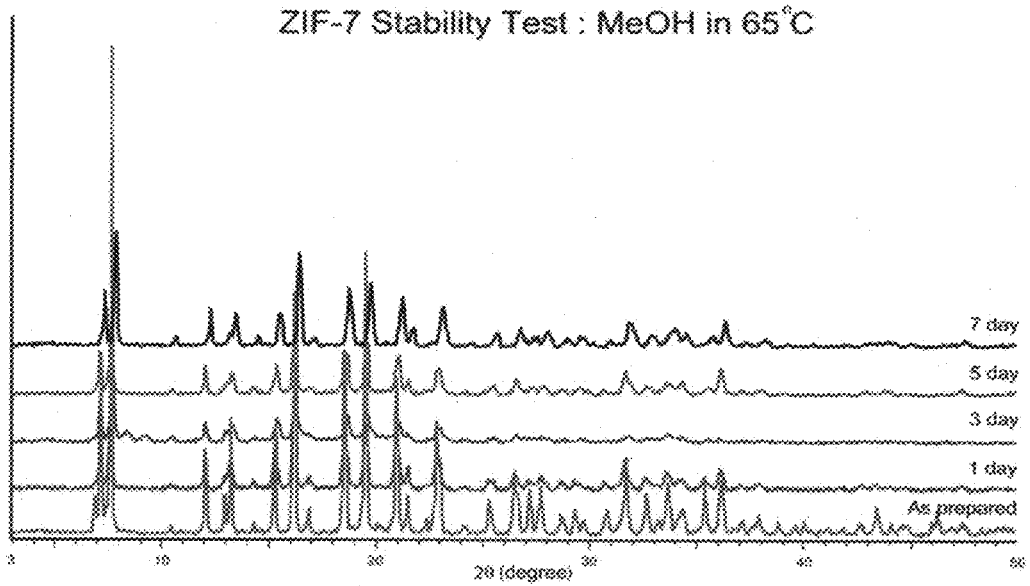
FIG. 26 shows PXRD patterns of ZIF-7 collected during stability test in refluxing methanol. The framework structure of ZIF-7 was unchanged after 7 days.
Figure 27:
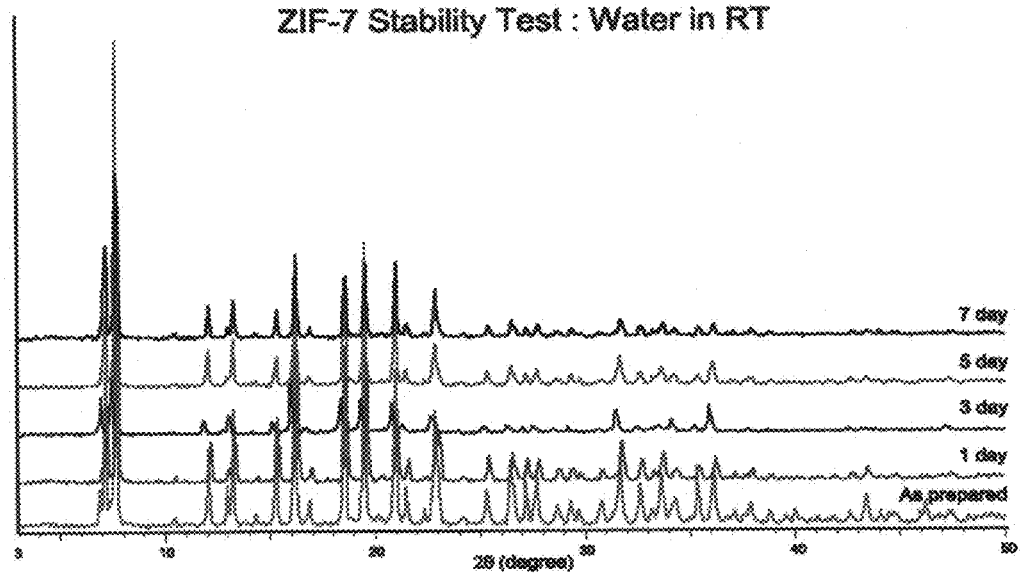
FIG. 27 shows PXRD patterns of ZIF-7 collected during stability test in water at room temperature. The framework structure of ZIF-7 was unchanged after 7 days.
Figure 28:
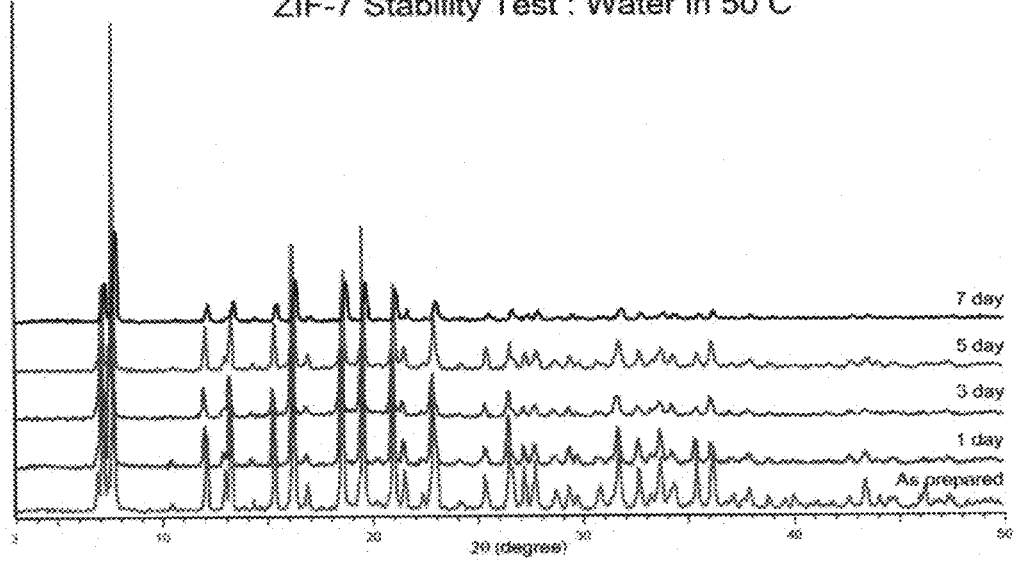
FIG. 28 shows PXRD patterns of ZIF-7 collected during stability test in water at 50° C. The framework structure of ZIF-7 was unchanged after 7 days.
Figure 29:
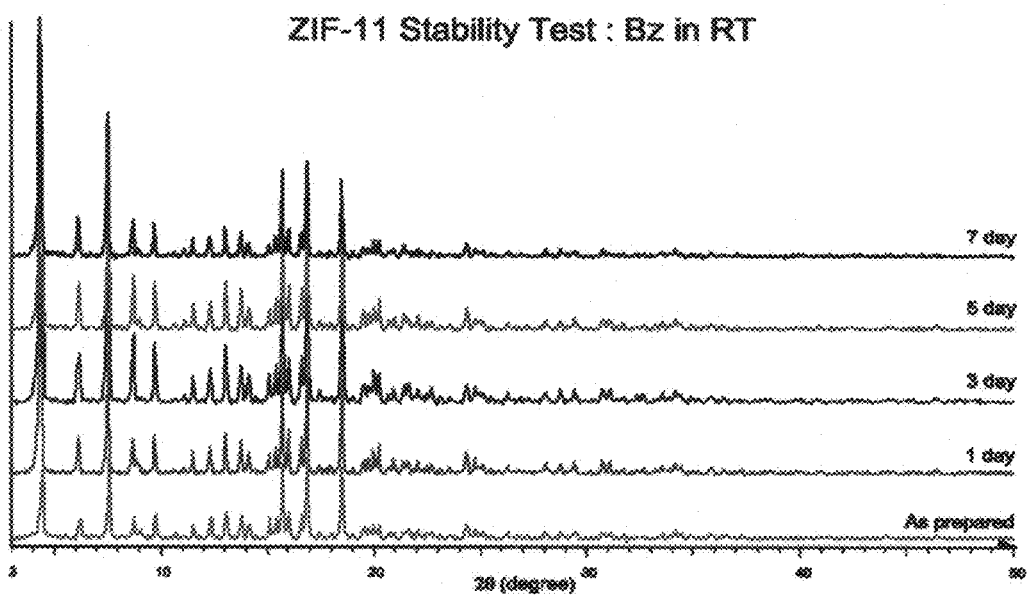
FIG. 29 shows PXRD patterns of ZIF-11 collected during stability test in benzene at room temperature. The framework structure of ZIF-11 was unchanged after 7 days.
Figure 30:
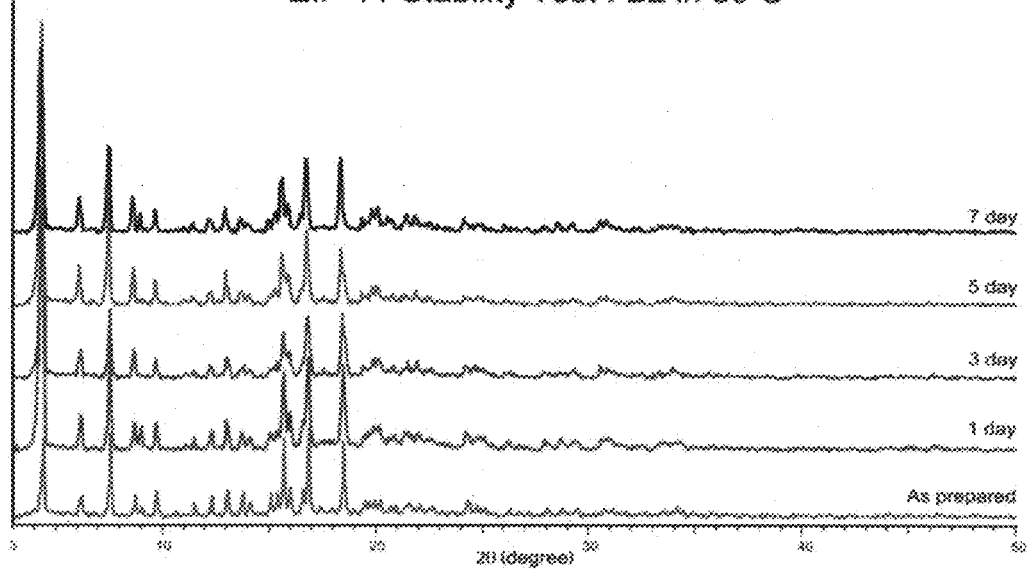
FIG. 30 shows PXRD patterns of ZIF-11 collected during stability test in refluxing benzene. The framework structure of ZIF-11 was unchanged after 7 days.
Figure 31:
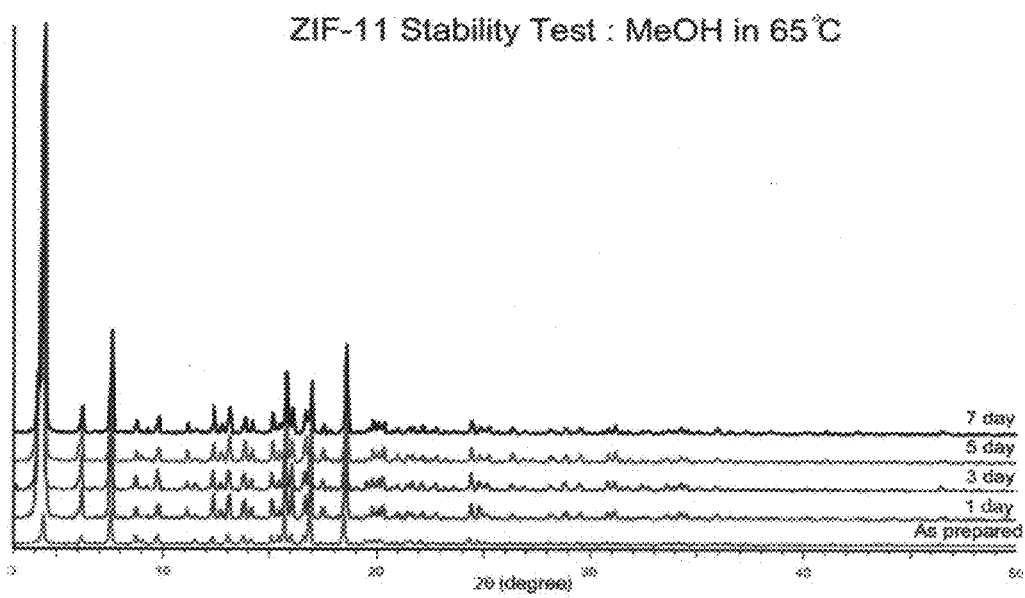
FIG. 31 shows PXRD patterns of ZIF-11 collected during stability test in refluxing methanol. The framework structure of ZIF-11 was unchanged after 7 days.
Figure 32:
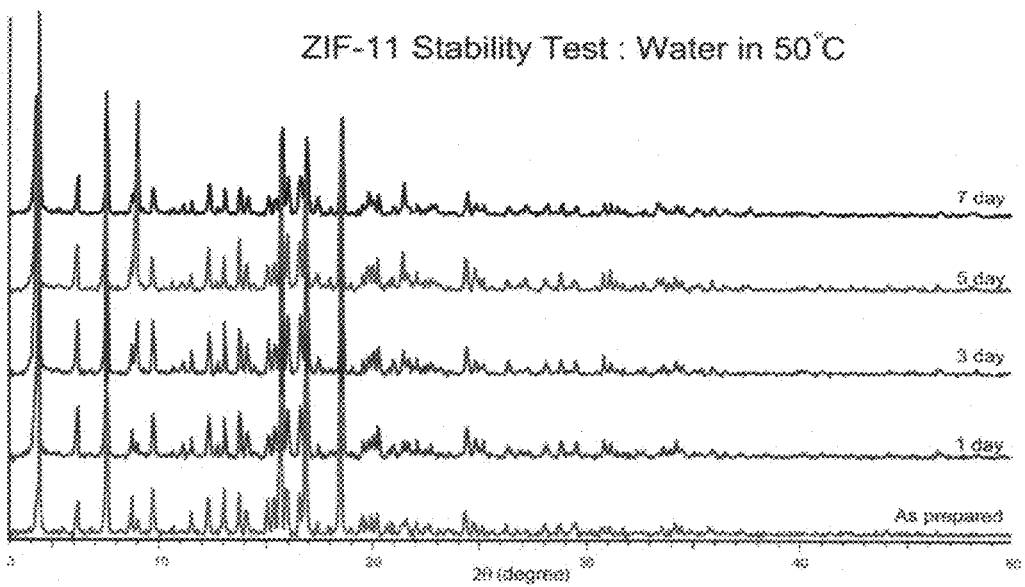
FIG. 32 shows PXRD patterns of ZIF-11 collected during stability test in water at 5° C. The framework structure of ZIF-11 was unchanged after 7 days.
Figure 33:
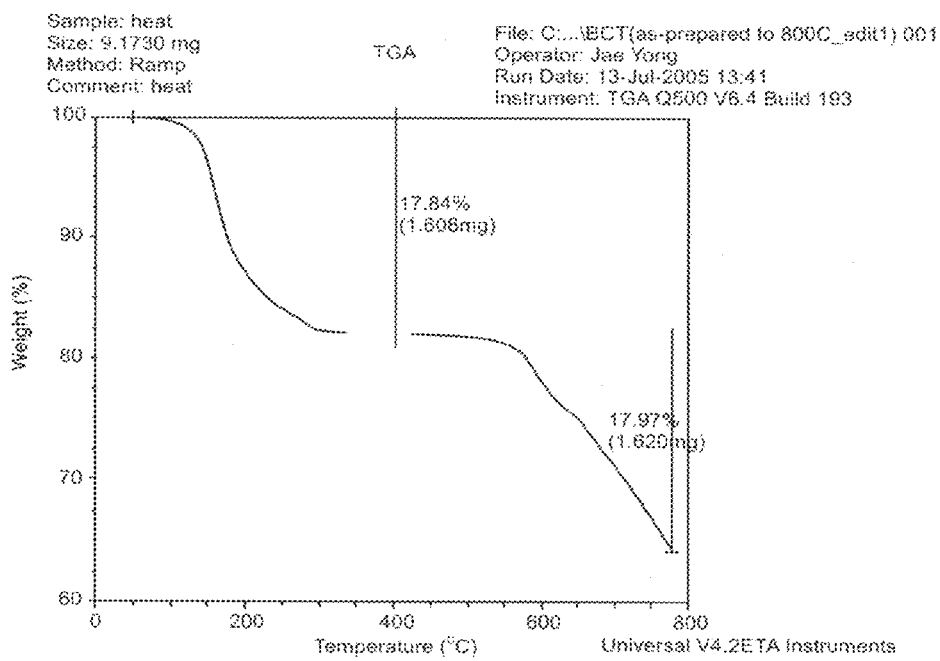
FIG. 33 shows TGA trace of as-synthesized ZIF-1 (crb).
Figure 34:
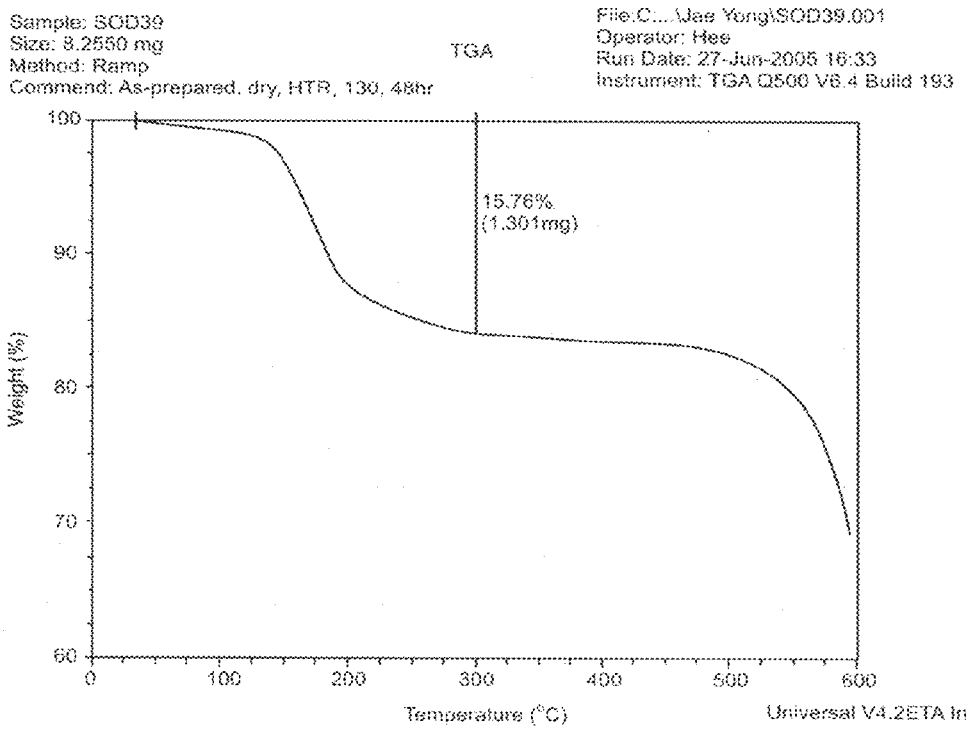
FIG. 34 shows TGA trace of as-synthesized ZIF-7 (sod).

The FT-IR spectrum of imidazole shows many characteristics of nitrogen-containing heterocycle. For pyrazoles, imidazoles, triazoles and tetrazoles, the C—H stretch absorbs near 3125 cm$^{-1}$. The double bonds on the ring absorb with several bands between 1665-1430 cm$^{-1}$ when the ring system is not substituted so as to allow the formation of tautomers. The NH group absorbs strongly between 3335-2500 cm$^{-1}$, and in many cases is very similar in shape to the OH stretch of the carboxylic acid dimmer. In the imidazoles, this band is accompanied by a weak band near 1820 cm$^{-1}$. As shown in FIG. 4(b), the complete disappearance of the strong and broad NH band between 3350-2500 cm$^{-1}$ and the associated weak band near 1820 cm$^{-1}$ indicates that the imidazole links in ZIF-5 In2Zn3(IM)12 has been fully deprotonated.

ZIF-20: Zn(Pur)$_2$.(DMF)$_{0.75}$(H$_2$O)$_{1.5}$. A solid mixture of zinc nitrate tetrahydrate Zn(NO$_3$)$_2$.4H$_2$O (65 mg, 0.25 mmol, EM Science) and purine (150 mg, 1.25 mmol, Fluka or Sigma) was dissolved in 5 mL DMF (Fisher) in a 20-mL vial to obtain a slightly suspended solution. The vial was tightly capped and heated in a 65° C. isothermal oven for 3 days to yield pale yellow octahedral crystals along with small amount of powder. After cooling the vial to room temperature naturally, the powder product was removed by decanting with mother liquor and DMF (5 mL×3). The crystals were dried in air for 30 min [yield: 48 mg, 50% based on Zn(NO$_3$)$_2$.4H$_2$O]. Elemental analysis: Calcd for Zn(Pur)$_2$.(DMF)$_{0.75}$(H$_2$O)$_{1.5}$: C, 38.17; H, 3.73; N, 31.80. Found C, 37.93; H, 3.52; N, 31.85%. FT-IR (KBr, 4000-400 cm$^{-1}$): 3433(br), 3098(w), 3065(w), 3036(w), 2930(w), 2856(w), 1670(s), 1589(s), 1568(m), 1477(s), 1398(s), 1310(s), 1221(s), 1192(m), 1094 (m), 1020(w), 924(m), 804(m), 791(m), 683(w), 644(m), 621 (w), 575(w), 498(w), 403(w).

ZIF-21: Co(Pur)$_2$.(DMF)(H$_2$O). A solid mixture of cobalt (II) nitrate hexahydrate Co(NO$_3$)$_2$.6H$_2$O (146 mg, 0.502 mmol, Aldrich) and purine (300 mg, 2.50 mmol) were dissolved in DMF (5 mL) in a 20-mL vial. To the solution, 2.0 M dimethylamine solution in MeOH (1.25 mL, 2.50 mmol, Aldrich) was added. The vial was tightly capped and heated in a 85° C. isothermal oven for 24 hours to yield purple octrahedral crystals. After cooling the vial to room temperature naturally, the crystals were rinsed with DMF (5 mL×3) and dried in air for 1 hour [yield: 92 mg, 47% based on Co(NO$_3$)$_2$.6H$_2$O]. Elemental analysis: Calcd for Co(Pur)$_2$.(DMF)(H$_2$O): C, 40.22; H, 3.89; N, 32.47. Found C, 40.36; H, 3.93; N, 32.16%. FT-IR (KBr, 4000-400 cm$^{-1}$): 3418(br), 3086(w), 2924(w), 2855(w), 1665(s), 1589(s), 1560(m), 1468(s), 1443 (w), 1396(s), 1308(s), 1234(w), 1207(s), 1188(s), 1109(m), 916(m), 804(m), 791(w), 677(w), 648(m), 623(w), 573(w), 500(w).

ZIF-22: Zn(5-Azabenzimidazolato)$_2$.(DMF)$_{0.75}$(H$_2$O)$_2$. A solid mixture of zinc nitrate tetrahydrate Zn(NO$_3$)$_2$.4H$_2$O (52 mg, 0.20 mmol) and 5-azabenzimidazole (238 mg, 2.00 mmol, Aldrich) was dissolved in 2 mL DMF in a 4-mL vial to obtain a white precipitate. The vial was tightly capped and heated in a 150° C. isothermal oven for 3 days to yield pale yellow octahedral crystals along with small amount of powder. After cooling the vial to room temperature naturally, the powder product was removed by decanting with mother liquor and DMF (4 mL×3). The crystals were dried in air for 30 min [yield: 68 mg, 87% based on Zn(NO$_3$)$_2$.4H$_2$O]. Elemental analysis: Calcd for Zn(5-Azabenzimidazolato)$_2$. (DMF)$_{0.75}$(H$_2$O)$_2$: C, 43.61; H, 4.43; N, 24.09. Found C, 43.74; H, 4.33; N, 24.24%. FT-IR (KBr, 4000-400 cm$^{-1}$): 3422(br), 3067(br), 2930(w), 2858(w), 1672(s), 1601(s), 1572(w), 1468(s), 1439(m), 1408(w), 1385(s), 1342(w), 1313(s), 1285(m), 1234(s), 1205(w), 1186(m), 1173(w), 1096(m), 1063(w), 1038(w), 1016(m), 991(w). 918(s), 816 (m), 793(m), 660(m), 644(m), 613(m), 565(w), 467(w), 420 (w).

ZIF-23: Zn(4-Azabenzimidazolato)$_2$.(H$_2$O)$_{0.25}$. A solid mixture of zinc nitrate tetrahydrate Zn(NO$_3$)$_2$.4H$_2$O (52 mg, 0.20 mmol) and 4-azabenzimidazole (119 mg, 1.00 mmol, Aldrich) was dissolved in 1 mL DMF in a 4-mL vial. The vial was tightly capped and heated in a 100° C. isothermal oven for 1 day to yield pale yellow prism crystals. After cooling the vial to room temperature naturally, the crystals were rinsed with DMF (5 mL×3) and dried in air for 30 min [yield: 55 mg, 90% based on Zn(NO$_3$)$_2$.4H$_2$O]. The same product was obtained in the reaction at different temperature (65 and 150°

C.), at which ZIF-20 and -22 were synthesized, respectively. Reaction with a different ligand/metal ratio (1:10, instead of 1:5) as used in a synthesis of ZIF-21 also gave the same compound. Elemental analysis: Calcd for Zn(4-Azabenzimidazolato)$_2$.(H$_2$O)$_{0.25}$: C, 47.08; H, 2.80; N, 27.45. Found C, 47.00; H, 2.82; N, 27.84%. FT-IR (KBr, 4000-400 cm$^{-1}$): 3439(br), 3080(m), 3053(m), 2937(w), 1919(w), 1879(w), 1850(w), 1665(m), 1597(s), 1574(w), 1474(s), 1406(s), 1395 (w), 1313(m), 1290(s), 1263(w), 1225(m), 1186(m), 1117 (w), 1042(w), 1013(w), 959(w), 918(m), 802(m), 771(s), 667 (m), 652(s), 594(w), 569(w), 503(m), 490(w).

Experimental and Refinement Details for ZIF-1 (crb). A colorless cubic crystal (0.15×0.10×0.10 mm$^3$) of ZIF-1 was placed in a 0.3 mm diameter borosilicate capillary along with a small amount of mother liquor, which was flame sealed, and mounted on a Bruker SMART APEX CCD diffractometer while being flash frozen to 223(2) K in a liquid N2 cooled stream of nitrogen gas. Using 951 reflections chosen from the full data set, it was determined that the crystal was twinned by a rotation of 180° about the real axis [0.234-0.935 1.000]. Using the orientation matrices produced by this program, the data were reduced to F$^2$ values using the two-component version of SAINT-Plus (v. 7.0). Integration of the data in the orthorhombic cell yielded a total of 41904 reflections of which 20536 were greater than 4σ(I). The range of θ was from 1.92 to 29.63°. The structure was solved in the monoclinic P21/n space group with Z=4 using direct methods. All non-hydrogen atoms were refined anisotropically with hydrogen atoms generated as spheres riding the coordinates of their parent atoms. Final full matrix least-squares refinement on F$^2$ converged to R1=0.0423 (F>2σF)) and wR2=0.0632 (all data) with GOF=1.053. Most residual electron density in the final F-map was closely associated with the guest dimethylacetamide molecule within the pore of ZIF-1. However, the largest peak lies directly on Zn1, and is an artifact of refinement of structure with a twinned dataset. Crystal data and structure refinement for ZIF-1: Empirical formula, C16 H21 N9 O Zn2; Formula weight, 486.16; Temperature, 223(2) K; Wavelength, 0.71073 Å; Crystal system, Monoclinic; Space group, P21/n; Unit cell dimensions, a=9.7405(19) Å; α=90°, b=15.266(3) Å, β=98.62(3) Å, c=14.936(3) Å; γ=90°; Volume, 2195.8 Å$^3$; Z, 4; Density (calculated), 1.471 Mg/m3; Absorption coefficient, 2.209 mm–1; F(000), 992; Crystal size, 0.15×0.10×0.10 mm3; Theta range for data collection, 1.92 to 29.63°. Index ranges –13<=h<=13, –21<=k<=21, –20<=l<=20 Reflections collected 41776 Independent reflections 41904 [R(int)=0.0000] Completeness to theta=29.63° 99.2% Absorption correction Semi-empirical from equivalents Max. and min. transmission 0.8093 and 0.7329 Refinement method Full-matrix least-squares on F$^2$ Data/restraints/parameters 41904/0/257 Goodness-of-fit on F$^2$ 1.053 Final R indices [I>2sigma(I)] R1=0.0423, wR2=0.0603 R indices (all data) R1=0.0985, wR2=0.0632 Largest diff. peak and hole 1.437 and –0.583 e.E$^{-3}$.

Atomic coordinates (×10$^4$) and equivalent isotropic displacement parameters (Å$^2$×10$^3$) for ZIF-1. U(eq) is defined as one third of the trace of the orthogonalized U$^{ij}$ tensor.

| | x | y | z | U(eq) |
|---|---|---|---|---|
| C(1S) | 1733(3) | 8647(2) | 9015(2) | 228(2) |
| C(2S) | 1364(5) | 9681(3) | 9105(3) | 155(2) |
| C(4S) | –808(2) | 9302(2) | 8364(2) | 180(1) |
| C(3S) | 80(4) | 10828(2) | 8893(2) | 226(2) |
| N(1S) | 320(3) | 9815(3) | 8816(2) | 191(2) |
| O(1S) | 2360(2) | 10096(2) | 9471(1) | 177(1) |
| C(1) | 5301(2) | 9080(1) | 8433(1) | 49(1) |
| C(2) | 5492(2) | 8987(1) | 7055(1) | 70(1) |
| C(3) | 5737(2) | 8193(1) | 7443(1) | 72(1) |
| C(4) | 8893(2) | 6816(1) | 9818(1) | 72(1) |
| C(5) | 8137(2) | 6361(1) | 8521(1) | 52(1) |
| C(6) | 4565(2) | 5453(1) | 8838(1) | 62(1) |
| C(7) | 4441(2) | 7184(1) | 10838(1) | 67(1) |
| C(8) | 1680(2) | 10102(1) | 6505(1) | 65(1) |
| C(9) | 1756(2) | 11462(1) | 6762(1) | 48(1) |
| C(10) | 5040(2) | 11479(1) | 5566(1) | 68(1) |
| C(11) | 4271(2) | 11705(1) | 9101(1) | 47(1) |
| C(12) | 5691(2) | 12362(1) | 8402(1) | 69(1) |
| N(1) | 5608(1) | 8250(1) | 8336(1) | 46(1) |
| N(2) | 5194(1) | 9558(1) | 7686(1) | 46(1) |
| N(3) | 7723(1) | 6753(1) | 9222(1) | 44(1) |
| N(4) | 4522(1) | 6328(1) | 8680(1) | 45(1) |
| N(5) | 5345(1) | 7599(1) | 10387(1) | 45(1) |
| N(6) | 2511(1) | 10755(1) | 6902(1) | 46(1) |
| N(7) | 4871(1) | 11644(1) | 8368(1) | 44(1) |
| N(8) | 5533(1) | 11177(1) | 6399(1) | 44(1) |
| Zn(1) | 4532(1) | 10761(1) | 7390(1) | 45(1) |
| Zn(2) | 5845(1) | 7261(1) | 9205(1) | 46(1) |

Experimental and Refinement Details for ZIF2 CRB—Orthorhombic. A colorless rod-shaped crystal (0.15×0.05×0.03 mm$^3$) of ZIF-2 was placed in a 0.3 mm diameter borosilicate capillary along with a small amount of mother liquor, which was flame sealed, and mounted on a Bruker SMART APEX CCD diffractometer while being flash frozen to 153(2) K in a liquid N2 cooled stream of nitrogen gas. Integration of the data in the orthorhombic cell yielded a total of 12384 reflections of which 4094 were unique and 1936 were greater than 4σ(I). The range of θ was from 1.67 to 23.25°. Analysis of the data showed negligible decay during collection. The structure was solved in the monoclinic Pbca space group with Z=8 using direct methods. All non-hydrogen atoms were refined anisotropically with hydrogen atoms generated as spheres riding the coordinates of their parent atoms. Final full matrix least-squares refinement on F$^2$ converged to R1=0.0591 (F>2σF)) and wR2=0.1523 (all data) with GOF=0.924. All residual electron density in the final F-map was closely associated with the guest dimethylformamide molecule within the pore of ZIF-2. Crystal data and structure for ZIF2: Empirical formula, C21 H12 N11 O3 Zn2; Formula weight, 597.16; Temperature, 153 K; Wavelength, 0.71073 Å; Crystal system, Orthorhombic; Space group, P b c a; Unit cell dimensions, a=9.679(3) Å, α=90°, b=24.114(6) Å, β=90°, c=24.450(6) Å, γ=90°; Volume, 5707 Å$^3$, Z, 8; Density (calculated) 1.390 Mg/m$^3$; Absorption coefficient, 1.722 mm$^{-1}$; F(000), 2392; Crystal size, 0.15×0.05×0.03 mm$^3$; Theta range for data collection, 1.67 to 23.25°. Index ranges –10<=h<=10, –26<=k<=19, –13<=l<=27 Reflections collected 12384 Independent reflections 4094 [R(int)=0.0809] Completeness to theta=23.25° 99.9% Absorption correction Semi-empirical from equivalents Max. and min. transmission 0.950 and 0.902 Refinement method Full-matrix least-squares on F$^2$ Data/restraints/parameters 4094/0/334 Goodness-of-fit on F$^2$ 0.924 Final R indices [I>2sigma(I)] R1=0.0591, wR2=0.1299 R indices (all data) R1=0.1317, wR2=0.1523 Largest diff. peak and hole 0.600 and –0.447 e.E$^{-3}$ Atomic coordinates (×10$^4$) and equivalent isotropic displacement parameters (Å$^2$×10$^3$) for ZIF-2. U(eq) is defined as one third of the trace of the orthogonalized U$^{ij}$ tensor.

|       | x        | y       | z       | U(eq)  |
|-------|----------|---------|---------|--------|
| Zn(1) | −151(1)  | 1747(1) | 5012(1) | 21(1)  |
| Zn(2) | −20(1)   | 18(1)   | 3239(1) | 21(1)  |
| N(4)  | 1184(7)  | 2346(3) | 4819(3) | 21(2)  |
| N(3)  | −1968(6) | 2106(3) | 5213(3) | 19(2)  |
| C(1)  | −172(8)  | 810(4)  | 4181(4) | 23(2)  |
| C(7)  | −2534(9) | 124(3)  | 2492(4) | 19(2)  |
| C(4)  | 1034(9)  | 2722(4) | 4402(4) | 34(3)  |
| N(5)  | −1215(6) | −51(3)  | 2572(3) | 20(2)  |
| C(9)  | −919(8)  | −340(4) | 2116(4) | 25(2)  |
| C(5)  | 2416(8)  | 2463(4) | 5033(4) | 24(2)  |
| N(6)  | 1941(6)  | −55(3)  | 2982(3) | 15(2)  |
| C(8)  | −2016(8) | −341(4) | 1779(4) | 27(2)  |
| C(10) | −78(8)   | 818(4)  | 5818(4) | 23(2)  |
| C(6)  | −2847(8) | 1943(4) | 5618(4) | 26(2)  |
| N(1)  | −500(7)  | 1313(3) | 4336(3) | 20(2)  |
| C(2)  | −1026(10)| 1548(4) | 3873(4) | 40(3)  |
| C(11) | 1358(9)  | 1058(4) | 6445(4) | 32(3)  |
| N(2)  | −433(7)  | 702(3)  | 3654(3) | 19(2)  |
| C(3)  | −995(10) | 1172(4) | 3457(4) | 37(3)  |
| C(12) | 1351(10) | 1457(4) | 6055(4) | 38(3)  |
| N(8)  | 451(7)   | 1309(3) | 5646(3) | 22(2)  |
| N(7)  | 432(7)   | 651(3)  | 6307(3) | 21(2)  |
| O(1S) | 7587(7)  | −43(4)  | 5355(3) | 62(1)  |
| N(1S) | 6465(9)  | 225(5)  | 4596(4) | 74(4)  |
| C(11S)| 7204(12) | −109(7) | 4880(6) | 88(5)  |
| C(12S)| 6097(16) | 806(6)  | 4852(7) | 104(6) |
| C(13S)| 6066(12) | 176(6)  | 4022(4) | 76(4)  |
| O(2S) | 5735(9)  | 1399(4) | 2944(3) | 81(3)  |
| N(2S) | 4192(8)  | 1504(3) | 3619(4) | 38(2)  |
| C(21S)| 4593(11) | 1225(5) | 3172(5) | 56(4)  |
| C(22S)| 4968(10) | 1941(5) | 3893(5) | 61(4)  |
| C(23S)| 2875(10) | 1302(5) | 3872(5) | 60(4)  |
| O(3S) | 3673(8)  | 2156(4) | 6660(3) | 66(3)  |
| N(3S) | 2886(9)  | 2179(4) | 7527(4) | 52(3)  |
| C(31S)| 2976(11) | 2383(5) | 7019(5) | 57(4)  |
| C(32S)| 1992(12) | 2496(6) | 7918(5) | 79(4)  |
| C(33S)| 3664(15) | 1688(5) | 7707(5) | 86(5)  |

Experimental and Refinement Details for ZIF-3. A colorless prismatic crystal (0.20×0.20×0.15 mm$^3$) of ZIF-3 was placed in a 0.3 mm diameter borosilicate capillary along with a small amount of mother liquor, which was flame sealed, and mounted on a Bruker SMART APEX CCD diffractometer while being flash frozen to 258(2) K in a liquid N2 cooled stream of nitrogen gas. Integration of the data in a primitive tetragonal cell yielded a total of 50492 reflections of which 3091 were unique and 1349 were greater than 4σ(I). The range of θ was from 1.62 to 25.72°. Analysis of the data showed negligible decay during collection. The structure was solved in the monoclinic P42/mnm space group with Z=16 using direct methods. All non-hydrogen atoms were refined anisotropically except for electron density within the pores which were modeled as isotropic oxygen atoms, hydrogen atoms were generated as spheres riding the coordinates of their parent atoms. Final full matrix least-squares refinement on F$^2$ converged to R1=0.0610 (F>2σF)) and wR2=0.1878 (all data) with GOF=1.012. All residual electron density in the final F-map was closely associated with the guest molecules within the pore of ZIF-3. Crystal data and structure refinement for ZIF-3: Empirical formula, C6 H6 N4 O3 Zn; Formula weight, 247.52; Temperature, 258 K; Wavelength, 0.71073 Å; Crystal system, Tetragonal; Space group, P42/mnm; Unit cell dimensions, a=18.9701 Å, α=90°, b=18.9701 Å, β=90°, c=16.740 Å, γ=90°; Volume, 6024.3 Å$^3$, Z, 16; density (calculated), 1.092 Mg/m$^3$; Absorption coefficient, 1.622 mm$^{-1}$; F(000), 1984; Crystal size, 0.20×0.20×0.15 mm$^3$; Theta range for data collection, 1.62 to 25.72°. Index ranges −23<=h<=23, −23<=k<=23, −20<=l<=20 Reflections collected 50942 Independent reflections 3091 [R(int) =0.1647] Completeness to theta=25.72° 99.3% Max. and min. transmission 0.7929 and 0.7373 Refinement method Full-matrix least-squares on F$^2$ Data/restraints/parameters 3091/0/146 Goodness-of-fit on F$^2$ 1.012 Final R indices [I>2sigma(I)] R1=0.0610, wR2=0.1736 R indices (all data) R1=0.1293, wR2=0.1878 Largest diff. peak and hole 0.963 and −0.485 e.E$^{-3}$.

Atomic coordinates (×10$^4$) and equivalent isotropic displacement parameters (Å$^2$×10$^3$) for ZIF-3. U(eq) is defined as one third of the trace of the orthogonalized U$^{ij}$ tensor.

|       | x        | y        | z        | U(eq)   |
|-------|----------|----------|----------|---------|
| O(1S) | 4194(19) | 630(20)  | 0        | 240(20) |
| O(2S) | 4590(40) | 190(50)  | 0        | 500(50) |
| O(3S) | 5240(20) | 4090(30) | 0        | 780(110)|
| O(4S) | 5000     | 0        | 0        | 470(100)|
| O(5S) | 5000     | 0        | 1113(17) | 252(12) |
| O(6S) | 5815(12) | 4185(12) | 0        | 330(30) |
| O(7S) | 9005(10) | 995(10)  | 1863(16) | 408(16) |
| O(8S) | 5480(30) | 3610(20) | 0        | 630(50) |
| Zn(1) | 6055(1)  | 1734(1)  | 1792(1)  | 58(1)   |
| C(1)  | 7107(4)  | 2893(4)  | 1727(6)  | 66(3)   |
| C(2)  | 6398(4)  | 3092(4)  | 2656(6)  | 110(3)  |
| C(3)  | 6382(4)  | 326(4)   | 2505(4)  | 59(2)   |
| C(4)  | 6992(4)  | 1093(4)  | 3066(5)  | 91(3)   |
| C(5)  | 6812(4)  | 1088(5)  | 422(5)   | 101(3)  |
| C(6)  | 5971(5)  | 1711(5)  | 0        | 65(3)   |
| C(7)  | 4527(4)  | 2173(4)  | 1623(5)  | 87(3)   |
| N(1)  | 6522(3)  | 2646(3)  | 2044(3)  | 57(1)   |
| N(2)  | 6492(3)  | 1006(3)  | 2488(3)  | 59(2)   |
| N(3)  | 6280(3)  | 1499(3)  | 671(3)   | 57(1)   |
| N(4)  | 5021(3)  | 1779(3)  | 1992(3)  | 61(2)   |

Experimental and Refinement Details for ZIF-4 (CAG). A colorless prismatic crystal (0.20×0.1×0.1 mm$^3$) of ZIF-4 was placed in a 0.3 mm diameter borosilicate capillary along with a small amount of mother liquor, which was flame sealed, and mounted on a Bruker SMART APEX CCD diffractometer while being flash frozen to 233(2) K in a liquid N2 cooled stream of nitrogen gas. Integration of the data in the orthorhombic cell yielded a total of 45791 reflections of which 6074 were unique and 3960 were greater than 4σ(I). The range of θ was from 2.18 to 29.63°. Analysis of the data showed negligible decay during collection. The structure was solved in the monoclinic Pbca space group with Z=8 using direct methods. Atoms C4 and C9 were found to be disordered and with each group modeled as its own independent free variable. All non-hydrogen atoms were refined anisotropically with hydrogen atoms generated as spheres riding the coordinates of their parent atoms. Final full matrix least-squares refinement on F$^2$ converged to R1=0.0406 (F>2σF)) and wR2=0.1109 (all data) with GOF=1.020. All residual electron density in the final F-map was closely associated with the guest dimethylformamide molecule within the pore of ZIF-4. Crystal data and structure refinement for ZIF-4: Empirical formula, C15 H19 N9 O Zn2; Formula weight, 472.13; Temperature, 233 K; Wavelength, 0.71073 Å; Crystal system, Orthorhombic; Space group, Pbca; Unit cell dimensions, a=15.3950 Å, α=90°, b=15.3073 Å, β=90°, c=18.426 Å, γ=90°; Volume, 4342.2 Å$^3$, Z, 8; Density (calculated), 1.444 Mg/m$^3$; Absorption coefficient, 2.232 mm−1; F(000), 1920; Crystal size, 0.20×0.15×0.15 mm$^3$; Theta range for data collection, 2.18 to 29.63°. Index ranges −21<=h<=21, −20<=k<=20, −25<=l<=25 Reflections collected 45791 Independent reflections 6074 [R(int)=0.1045] Completeness to theta=29.63° 99.2% Absorption correction Semi-empirical from equivalents Max. and min. transmission 0.7307 and 0.6638 Refinement method Full-matrix least-squares on F$^2$ Data/restraints/parameters 6074/0/243 Goodness-of-fit on F$^2$ 1.020 Final R indices [I>2sigma(I)] R1=0.0406, wR2=0.1041 R indices (all data) R1=0.0682, wR2=0.1109 Largest diff. peak and hole 0.575 and −0.483 e.E$^{-3}$.

Atomic coordinates (×10$^4$) and equivalent isotropic displacement parameters (Å$^2$×10$^3$) for ZIF-4. U(eq) is defined as one third of the trace of the orthogonalized U$^{ij}$ tensor.

|       | x        | y        | z        | U(eq)   |
|-------|----------|----------|----------|---------|
| C(1)  | 8577(2)  | 7339(2)  | 8602(1)  | 46(1)   |
| C(2)  | 8991(2)  | 6132(2)  | 9057(2)  | 66(1)   |
| C(3)  | 9708(2)  | 6582(2)  | 8837(2)  | 64(1)   |
| C(5)  | 6911(2)  | 5137(2)  | 7830(2)  | 84(1)   |
| C(6)  | 6198(2)  | 8224(2)  | 8907(2)  | 68(1)   |
| C(7)  | 5982(2)  | 7372(2)  | 8018(1)  | 49(1)   |
| C(8)  | 11059(2) | 8460(2)  | 9536(1)  | 47(1)   |
| C(10) | 10760(2) | 8659(2)  | 6609(2)  | 68(1)   |
| C(11) | 9053(2)  | 9871(2)  | 8616(1)  | 47(1)   |
| C(12) | 8628(3)  | 9499(2)  | 7571(2)  | 79(1)   |
| C(4A) | −2725(5) | 5951(6)  | 10703(4) | 50(2)   |
| C(9B) | 1830(5)  | 8976(6)  | 8675(4)  | 48(2)   |
| C(9A) | 1651(4)  | 9323(5)  | 8788(3)  | 54(2)   |
| C(4B) | −2920(4) | 5619(5)  | 10570(3) | 56(2)   |
| C(1S) | 2528(6)  | 3362(5)  | 4095(8)  | 304(9)  |
| C(2S) | 1571(12) | 2932(9)  | 3358(6)  | 368(9)  |
| C(3S) | 1240(9)  | 3195(15) | 4567(7)  | 541(17) |
| N(1)  | 8270(2)  | 6615(2)  | 8901(1)  | 48(1)   |
| N(2)  | 9438(1)  | 7351(1)  | 8540(1)  | 48(1)   |
| N(3)  | 6742(2)  | 6226(2)  | 10115(1) | 48(1)   |
| N(4)  | 6637(1)  | 5369(2)  | 8501(1)  | 49(1)   |
| N(5)  | 6349(1)  | 7393(1)  | 8668(1)  | 46(1)   |
| N(6)  | 11009(1) | 8676(2)  | 8847(1)  | 48(1)   |
| N(7)  | 10621(2) | 8120(2)  | 7181(1)  | 48(1)   |
| N(8)  | 9245(2)  | 9329(1)  | 8077(1)  | 48(1)   |
| N(1S) | 1799(3)  | 3208(3)  | 4021(2)  | 113(1)  |
| O(1S) | 3116(2)  | 3661(3)  | 4296(3)  | 143(2)  |
| Zn(1) | 7021(1)  | 6395(1)  | 9083(1)  | 44(1)   |
| Zn(2) | 10096(1) | 8360(1)  | 8137(1)  | 44(1)   |

Experimental and Refinement Details for ZIF-5 (GARNET). A colorless prism (0.15×0.12×0.10 mm$^3$) of ZIF-5 was placed in a 0.3 mm diameter borosilicate capillary along with a small amount of mother liquor, which was flame sealed, and mounted on a Bruker SMART APEX CCD diffractometer while being flash frozen to 196(2) K in a liquid N2 cooled stream of nitrogen. A total of 35102 reflections were collected of which 1107 were unique and 997 were greater than 4σ(I). The range of θ was from 2.27 to 28.26°. Analysis of the data showed negligible decay during collection. The structure was solved in the cubic Ia-3d space group with Z=8 using direct methods. All non-hydrogen atoms were refined anisotropically with hydrogen atoms generated as spheres riding the coordinates of their parent atoms. Final full matrix least-squares refinement on F$^2$ converged to R1=0.0191 (F>2σF)) and wR2=0.0553 (all data) with GOF=1.121. Crystal data and structure refinement for ZIF-5: Empirical formula, C36 H36 In2 N24 Zn3; Formula weight, 1230.64; Temperature, 153 K; Wavelength, 0.71073 Å; Crystal system, Cubic Space group, Ia-3d; Unit cell dimensions, a=21.9619 Å, α=90°, b=21.9619(6) Å, β=90°; c=21.9619 Å, γ=90°; Volume, 10592.8 Å$^3$, Z, 8; Density (calculated), 1.543 Mg/m$^3$; Absorption coefficient, 2.247 mm−1; F(000), 4864; Crystal size, 0.15×0.12×0.10 mm$^3$; Theta range for data collection, 2.27 to 28.26°. Index ranges −29<=h<=27, −29<=k<=21, −29<=l<=25 Reflections collected 35102 Independent reflections 1107 [R(int)=0.0245] Completeness to theta=28.26° 100.0% Absorption correction Semi-empirical from equivalents Max. and min. transmission 0.799 and 0.703 Refinement method Full-matrix least-squares on F$^2$ Data/restraints/parameters 1107/0/62 Goodness-of-fit on F$^2$ 1.121 Final R indices [I>2sigma(I)] R1=0.0191, wR2=0.0531 R indices (all data) R1=0.0221, wR2=0.0553 Largest diff. peak and hole 0.762 and −0.155 e.E$^{-3}$.

Atomic coordinates (×10$^4$) and equivalent isotropic displacement parameters (Å$^2$×10$^3$) for ZIF-5. U(eq) is defined as one third of the trace of the orthogonalized U$^{ij}$ tensor.

|       | x       | y      | z        | U(eq)  |
|-------|---------|--------|----------|--------|
| In(1) | 10000   | 0      | 10000    | 20(1)  |
| Zn(1) | 7500    | 1250   | 10000    | 21(1)  |
| N(2)  | 8182(1) | 748(1) | 9684(1)  | 25(1)  |
| N(1)  | 9065(1) | 243(1) | 9695(1)  | 24(1)  |
| C(1)  | 8677(1) | 595(1) | 10003(1) | 24(1)  |
| C(2)  | 8797(1) | 164(1) | 9135(1)  | 31(1)  |
| C(3)  | 8261(1) | 469(1) | 9128(1)  | 33(1)  |

Experimental and Refinement Details for ZIF-6 (GIS). A colorless block-shaped crystal (0.12×0.1×0.08 mm$^3$) of ZIF-6 was placed in a 0.3 mm diameter borosilicate capillary along with a small amount of mother liquor, which was flame sealed, and mounted on a Bruker SMART APEX CCD diffractometer while being flash frozen to 258(2) K in a liquid N2 cooled stream of nitrogen 8840 reflections of which 1582 were unique and 821 were greater than 4σ(I). The range of θ was from 1.49 to 24.71°. Analysis of the data showed negligible decay during collection. The structure was solved in the monoclinic I41/amd (origin choice No. 2) space group with Z=16 using direct methods. Atoms C4A and C4B were the two components of a disordered carbon atom. The sof of C4A was refined as a free variable to converge at 0.53. Atoms C3A and C3B were two independent carbon atoms in an imidazole ring. This portion of the ring was disordered over two sites related by a two-fold axis. Therefore, the sofs of both C3A and C3B were fixed at 0.50. To treat the diffuse electron density, a protein diffuse scattering correction (SWAT) command was applied. The two variables g and U were refined to converge at 1.1 and 2.9, respectively. All non-hydrogen atoms were refined anisotropically with hydrogen atoms generated as spheres riding the coordinates of their parent atoms. Final full matrix least-squares refinement on F$^2$ converged to R1=0.0642 (F>2σF)) and wR2=0.2394 (all data) with GOF=1.013. All residual electron density in the final F-map was closely associated with the guest molecules within the pore of ZIF-6. Absorption corrections did not improve the quality of the data and was not applied. Crystal data and structure refinement for ZIF-6: Empirical formula, C6 H6 N4 O0.50 Zn; Formula weight, 207.52; Temperature, 258 K; Wavelength, 0.71073 Å; Crystal system, Tetragonal; Space group, I4(1)/amd; Unit cell dimensions, a=18.515 Å, α=90°, b=18.515 Å, β=90°, c=20.245 Å, γ=90°; Volume, 6940.2 Å$^3$, Z, 16; Density (calculated), 0.794 Mg/m$^3$; Absorption coefficient, 1.390 mm−1; F(000), 1664; Crystal size, 0.12×0.10× 0.08 mm$^3$; Theta range for data collection, 1.49 to 24.71°. Index ranges −6<=h<=21, −21<=k<=20, −23<=l<=21 Reflection collected 8840 Independent reflections 1582 [R(int)=0.0826] Completeness to theta=24.71° 99.4% Refinement method Full-matrix least-squares on F$^2$ Data/restraints/parameters 1582/0/58 Goodness-of-fit on F$^2$ 1.013 Final R indices [I>2sigma(I)] R1=0.0642, wR2=0.2260 R indices (all data) R1=0.1037, wR2=0.2394 Largest diff. peak and hole 0.735 and −0.318 e.E$^{-4}$.

Atomic coordinates (×10$^4$) and equivalent isotropic displacement parameters (Å$^2$×10$^3$) for ZIF-6. U(eq) is defined as one third of the trace of the orthogonalized U$^{ij}$ tensor.

|       | x        | y        | z        | U(eq)   |
|-------|----------|----------|----------|---------|
| C(1)  | 3409(5)  | 5000     | 0        | 70(3)   |
| C(2)  | 3477(6)  | 2500     | 1276(4)  | 75(3)   |
| C(3A) | 2317(9)  | 4963(9)  | 396(8)   | 82(5)   |
| C(3B) | 2316(9)  | 5323(8)  | −183(8)  | 79(4)   |
| C(4A) | 2410(10) | 2869(8)  | 1020(9)  | 95(7)   |
| C(4B) | 2660(13) | 2882(11) | 590(17)  | 144(11) |
| N(1)  | 3019(3)  | 4683(3)  | 470(3)   | 81(2)   |
| N(2)  | 3138(4)  | 3101(3)  | 1127(3)  | 86(2)   |
| Zn(1) | 3365(1)  | 4135(1)  | 1250     | 72(1)   |
| O(1)  | 5000     | 2500     | 2250(20) | 363(18) |

Experimental and Refinement Details for ZIF-7 (SOD). A colorless prismatic crystal (0.10×0.07×0.05 mm$^3$) of ZIF-7 was placed in a 0.3 mm diameter borosilicate capillary along with a small amount of mother liquor, which was flame sealed, and mounted on a Bruker SMART APEX CCD diffractometer while being flash frozen to 233 K in a liquid N2 cooled stream of nitrogen. A total of 8134 reflections were collected of which 4035 were unique and 1782 were greater than 4σ(I). The range of θ was from 1.65 to 29.55°. Analysis of the data showed negligible decay during collection. The structure was solved in the rhombohedral R-3 space group with Z=18 using direct methods. All non-hydrogen atoms were refined anisotropically with hydrogen atoms generated as spheres riding the coordinates of their parent atoms. Final full matrix least-squares refinement on F$^2$ converged to R1=0.0707 (F>2σF)) and wR2=0.1270 (all data) with GOF=1.038. All residual electron density in the final F-map was closely associated with the guest molecules within the pore of ZIF-7. Crystal data and structure refinement for ZIF-7: Empirical formula, C14 H10 N4 O2.24 Zn; Formula weight, 335.47; Temperature, 258 K; Wavelength, 0.71073 Å; Crystal system, Hexagonal; Space group, R-3; Unit cell dimensions, a=22.989 Å, α=90°, b=22.989 Å, β=90°, c=15.763 Å, γ=120°; Volume, 7214 Å$^3$, Z, 18; Density (calculated), 1.390 Mg/m$^3$; Absorption coefficient, 1.542 mm−1; F(000), 3059; Crystal size, 0.10×0.07×0.05 mm$^3$; Theta range for data collection, 1.65 to 29.55°. Index ranges −28<=h<=26, −26<=k<=14, −21<=l<=17 Reflections collected 8134 Independent reflections 4035 [R(int)=0.0998] Completeness to theta=29.55° 89.8% Absorption correction Semi-empirical from equivalents Max. and min. transmission 0.9269 and 0.8611 Refinement method Full-matrix least-squares on F$^2$ Data/restraints/parameters 4035/0/195 Goodness-of-fit on F$^2$ 1.038 Final R indices [I>2sigma(I)] R1=0.0707, wR2=0.1157 R indices (all data) R1=0.1711, wR2=0.1270 Largest diff. peak and hole 0.623 and −0.549 e.E$^{-3}$.

Atomic coordinates (×10$^4$) and equivalent isotropic displacement parameters (Å$^2$×10$^3$) for ZIF-7. U(eq) is defined as one third of the trace of the orthogonalized U$^{ij}$ tensor.

|       | x       | y        | z       | U(eq)  |
|-------|---------|----------|---------|--------|
| C(1)  | 6995(3) | 285(3)   | 1763(3) | 42(1)  |
| C(2)  | 6088(3) | −548(3)  | 2264(3) | 44(1)  |
| C(3)  | 5529(3) | −986(3)  | 2722(3) | 55(2)  |
| C(4)  | 5117(3) | −1604(3) | 2370(4) | 72(2)  |
| C(5)  | 5251(3) | −1785(3) | 1563(4) | 75(2)  |
| C(6)  | 7393(3) | 282(3)   | 4796(3) | 43(1)  |
| C(7)  | 8013(3) | 480(3)   | 4434(4) | 59(2)  |
| C(8)  | 5345(3) | 596(3)   | 3269(3) | 47(1)  |
| C(9)  | 5903(3) | 1202(3)  | 4306(3) | 52(2)  |
| C(10) | 6372(3) | 1565(3)  | 4966(4) | 72(2)  |
| C(11) | 7443(3) | 1972(3)  | 2400(3) | 54(2)  |
| C(12) | 6905(4) | 1797(3)  | 1802(4) | 74(2)  |
| C(13) | 6219(4) | 1915(4)  | 5529(4) | 94(2)  |
| C(14) | 7017(4) | 2271(4)  | 1175(4) | 91(2)  |
| N(1)  | 6589(2) | 113(2)   | 2433(2) | 40(1)  |
| N(2)  | 7480(2) | 1604(2)  | 3092(2) | 46(1)  |
| N(3)  | 6848(2) | 327(2)   | 4485(2) | 44(1)  |
| N(4)  | 5923(2) | 811(2)   | 3661(2) | 46(1)  |
| O(1S) | 0       | 0        | 6420(20)| 530(50)|
| O(2S) | 8416    | 1646     | 6568    | 75     |
| O(3S) | 6667    | 3333     | 3333    | 169(15)|
| O(4S) | 7832(7) | 1794(8)  | 6104(17)| 512(15)|
| O(5S) | 8167(13)| 1389(6)  | 7535(12)| 273(14)|
| Zn(1) | 6719(1) | 705(1)   | 3416(1) | 40(1)  |

Experimental and Refinement Details for ZIF-8 (SOD—Methyl Derivative). A colorless block crystal (0.16×0.10×0.0 mm$^3$) of ZIF-8 was placed in a 0.3 mm diameter borosilicate capillary along with a small amount of mother liquor, which was flame sealed, and mounted on a Bruker SMART APEX CCD diffractometer while being flash frozen to 258(2) K in a liquid N2 cooled stream of nitrogen. A total of 27202 reflections were collected of which 1302 were unique and 1009 were greater than 4σ(I). The range of θ was from 2.94 to 29.61°. Analysis of the data showed negligible decay during collection. The structure was solved in the cubic I-43m space group with Z=4 using direct methods. All non-hydrogen atoms were refined anisotropically with hydrogen atoms generated as spheres riding the coordinates of their parent atoms. Final full matrix least-squares refinement on F$^2$ converged to R1=0.0314 (F>2σF)) and wR2=0.0840 (all data) with GOF=0.546. All residual electron density in the final F-map was closely associated with the guest molecules within the pore of ZIF-8. Crystal data and structure refinement for ZIF-8: Empirical formula, C24 H30 N12 O10 Zn3; Formula weight, 842.71; Temperature, 258 K; Wavelength, 0.71073 Å; Crystal system, Cubic; Space group, I-43m; unit cell dimensions, a=16.9910 Å, α=90°; b=16.9910 Å, β=90°, c=16.9910 Å, γ=90°; Volume, 4905.2 Å$^3$, Z, 4; Density (calculated), 1.141 Mg/m$^3$; Absorption coefficient, 1.503 mm$^{-1}$; F(000), 1712; Crystal size, 0.16×0.10×0.10 mm$^3$; Theta range for data collection, 2.94 to 29.61°. Index ranges −23<=h<=23, −23<=k<=23, −23<=l<=23 Reflections collected 27202 Independent reflections 1302 [R(int)=0.0922] Completeness to theta=29.61° 98.9% Refinement method Full-matrix least-squares on F$^2$ Data/restraints/parameters 1302/0/46 Goodness-of-fit on F$^2$ 0.546 Final R indices [I>2sigma(I)] R1=0.0314, wR2=0.0758 R indices (all data) R1=0.0418, wR2=0.0840 Absolute structure parameter −0.01(2) Largest diff. peak and hole 0.428 and −0.216 e.E$^{-3}$.

Atomic coordinates (×10$^4$) and equivalent isotropic displacement parameters (Å$^2$×10$^3$) for ZIF-8. U(eq) is defined as one third of the trace of the orthogonalized U$^{ij}$ tensor.

|       | x        | y         | z         | U(eq)   |
|-------|----------|-----------|-----------|---------|
| C(1)  | 3771(1)  | 10079(3)  | 6230(1)   | 50(1)   |
| C(2)  | 3685(2)  | 8991(2)   | 6875(2)   | 71(1)   |
| C(3)  | 4061(2)  | 10855(2)  | 5939(2)   | 73(1)   |
| N(1)  | 4097(1)  | 9683(1)   | 6828(1)   | 55(1)   |
| O(1S) | 3043(13) | 6957(13)  | 6957(13)  | 315(16) |
| O(2S) | 1845(8)  | −410(30)  | 8155(8)   | 620(40) |
| O(3S) | 1763(17) | 8237(17)  | 8237(17)  | 480(30) |
| Zn(1) | 5000     | 10000     | 7500      | 50(1)   |

Experimental and Refinement Details for ZIF-9 (SOD—Cobalt Form). A purple cubic crystal (0 17×0.17×0.17 mm$^3$) of ZIF-9 was placed in a 0.3 mm diameter borosilicate capillary along with a small amount of mother liquor, which was flame sealed, and mounted on a Bruker SMART APEX CCD diffractometer while being flash frozen to 233(2) K in a liquid N2 cooled stream of nitrogen. A total of 24864 reflections were collected of which 3953 were unique and 2221 were greater than 4σ(I). The range of θ was from 2.42 to 28.35°. Analysis of the data showed negligible decay during collection. The structure was solved in the rhombohedral R-3 space group with Z=18 using direct methods. All non-hydrogen atoms were refined anisotropically with hydrogen atoms generated as spheres riding the coordinates of their parent atoms. Final full matrix least-squares refinement on F$^2$ converged to R1=0.0979 (F>2σF)) and wR2=0.2784 (all data) with GOF=1.032. All residual electron density in the final F-map was closely associated with the guest molecules within the pore of ZIF-9. Crystal data and structure refinement for ZIF-9: Empirical formula, C14 H10 N4 O2.24 Co; Formula weight, 251.89; Temperature, 258 K; Wavelength, 0.71073 Å; Crystal system, Hexagonal; Space group, R-3; Unit cell dimensions, a=22.9437 Å, α=90°, b=22.9437 Å, β=90°, c=15.747 Å, γ=120°; Volume, 7178.8 Å$^3$, Z, 18; Density (calculated), 1.398 Mg/m$^3$; Absorption coefficient, 1.089 mm$^{-1}$; F(000), 3066; Crystal size, 0.17×0.17×0.17 mm$^3$; Theta range for data collection, 2.42 to 28.35°. Index ranges −30<=h<=4, −16<=k<=25, −20<=l<=21 Reflections collected 24864 Independent reflections 3953 [R(int)=0.1010] Completeness to theta=28.35° 99.1% Max. and min. transmission 0.8365 and 0.8365 Refinement method Full-matrix least-squares on F$^2$ Data/restraints/parameters 3953/0/198 Goodness-of-fit on F$^2$ 1.032 Final R indices [I>2sigma(I)] R1=0.0979, wR2=0.2321 R indices (all data) R1=0.1700, wR2=0.2784 Largest diff. peak and hole 0.726 and −0.727 e.E$^{-3}$.

Atomic coordinates (×10$^4$) and equivalent isotropic displacement parameters (Å$^2$×10$^3$) for ZIF-9. U(eq) is defined as one third of the trace of the orthogonalized U$^{ij}$ tensor.

|  | x | y | z | U(eq) |
|---|---|---|---|---|
| C(1) | 3294(4) | 288(4) | 1756(4) | 44(2) |
| C(2) | 3367(3) | −544(3) | 2234(5) | 45(2) |
| C(3) | 3476(4) | −994(4) | 2714(5) | 53(2) |
| C(4) | 3270(5) | −1606(4) | 2345(7) | 69(2) |
| C(5) | 3926(4) | 2006(4) | 3394(4) | 45(2) |
| C(6) | 4522(4) | 1957(4) | 2377(5) | 47(2) |
| C(7) | 4870(4) | 1794(4) | 1800(5) | 61(2) |
| C(8) | 5228(6) | 2258(5) | 1181(7) | 82(3) |
| C(9) | 5291(4) | 1191(4) | 4339(4) | 48(2) |
| C(10) | 5183(5) | 1554(5) | 4965(6) | 70(3) |
| C(11) | 5696(6) | 1893(6) | 5538(7) | 90(3) |
| C(12) | 2903(4) | 293(3) | 4787(5) | 44(2) |
| C(13) | 2481(4) | 496(4) | 4439(6) | 57(2) |
| C(14) | 1923(4) | 381(5) | 4897(7) | 69(2) |
| Co(1) | 3988(1) | 701(1) | 3408(1) | 39(1) |
| N(1) | 3526(3) | 112(3) | 2427(4) | 43(1) |
| N(2) | 4124(3) | 1597(3) | 3063(4) | 47(1) |
| N(3) | 4880(3) | 796(3) | 3668(3) | 46(1) |
| N(4) | 3487(3) | 329(3) | 4482(3) | 42(1) |
| O(1) | 1667 | 8333 | 3333 | 90(3) |
| O(2) | 1775(15) | 7817(13) | 3890(40) | 480(30) |
| O(3) | 1965(9) | 8550(20) | 4160(30) | 500(30) |
| O(4) | 6667 | 3333 | 3333 | 260(20) |

Experimental and Refinement Details for ZIF-10 (MER). A colorless prismatic crystal (0.20×0.10×0.10 mm$^3$) of ZIF-10 was placed in a 0.3 mm diameter borosilicate capillary along with a small amount of mother liquor, which was flame sealed, and mounted on a Bruker SMART APEX CCD diffractometer while being flash frozen to 233(2) K in a liquid N2 cooled stream of nitrogen. At total of 66076 reflections were collected of which 3376 were unique and 1771 were greater than 4σ(I). The range of θ was from 1.06 to 26.37°. Analysis of the data showed negligible decay during collection. The structure was solved in the monoclinic I4/mmm space group with Z=32 using direct methods. Atoms C5 and C8 were found to be disordered and with each group modeled as its own independent free variable. All non-hydrogen atoms were refined anisotropically with hydrogen atoms generated as spheres riding the coordinates of their parent atoms. Final full matrix least-squares refinement on F$^2$ converged to R1=0.0636 (F>2σF)) and wR2=0.2457 (all data) with GOF=1.059. All residual electron density in the final F-map was closely associated with the guest molecules within the pore of ZIF-10. Crystal data and structure refinement for ZIF-10: Empirical formula, C6 H6 N4 O0.69 Zn; Formula weight, 210.52; Temperature, 223 K; Wavelength, 0.71073 Å; Crystal system, Tetragonal; Space group, I4/mmm; Unit cell dimensions, a=27.0608(18) Å, α=90°, b=27.0608 Å, β=90°, c=19.406 Å, γ=90°; Volume, 14211 Å$^3$, Z, 32; Density (calculated), 0.787 Mg/m$^3$; Absorption coefficient, 1.359 mm$^{-1}$; F(000), 3376; Crystal size, 0.2×0.1×0.1 mm$^3$; Theta range for data collection, 1.06 to 26.37°. Index ranges −33<=h<=33, −33<=k<=33, −24<=l<=24 Reflections collected 66076 Independent reflections 3998 [R(int)=0.1371] Completeness to theta=26.37° 99.2% Absorption correction Semi-empirical from equivalents Max. and min. transmission 0.873 and 0.850 Refinement method Full-matrix least-squares on F$^2$ Data/restraints/parameters 3998/0/118 Goodness-of-fit on F$^2$ 1.059 Final R indices [I>2sigma(I)] R1=0.0636, wR2=0.2183 R indices (all data) R1=0.1291, wR2=0.2457 Largest diff. peak and hole 0.557 and −0.501 e.E$^{-3}$.

Atomic coordinates (×10$^4$) and equivalent isotropic displacement parameters (Å$^2$×10$^3$) for ZIF-10. U(eq) is defined as one third of the trace of the orthogonalized U$^{ij}$ tensor.

|  | x | y | z | U(eq) |
|---|---|---|---|---|
| C(1) | 3671(3) | 1045(3) | 2279(5) | 109(3) |
| C(2) | 3282(3) | 1718(3) | 2500 | 72(3) |
| C(3) | 1874(2) | 1874(2) | 1477(5) | 64(2) |
| C(4) | 1918(3) | 1576(3) | 2479(4) | 103(3) |
| C(5A) | 2136(10) | 255(8) | 2226(19) | 166(14) |
| C(5B) | 2009(8) | 250(6) | 1709(11) | 103(8) |
| C(8A) | 3158(8) | 1635(10) | 354(8) | 80(7) |
| C(8B) | 3327(10) | 1419(10) | 358(8) | 103(8) |
| C(6) | 2684(4) | 0 | 1521(5) | 76(3) |
| C(7) | 2654(4) | 1075(4) | 0 | 68(3) |
| N(1) | 3242(2) | 1300(2) | 2134(3) | 69(2) |
| N(2) | 2114(2) | 1538(2) | 1832(3) | 67(2) |
| N(3) | 2488(2) | 409(2) | 1668(3) | 81(2) |
| N(4) | 2861(2) | 1233(2) | 571(3) | 68(2) |
| Zn(1) | 2679(1) | 1110(1) | 1546(1) | 61(1) |
| O(1) | 3917(15) | 0 | 0 | 224(18) |
| O(2) | 3924(9) | 0 | 1341(13) | 183(10) |
| O(3) | 5000 | 0 | 2500 | 240(30) |
| O(4) | 3060(20) | 0 | 3800(30) | 200(20) |
| O(5) | 3030(20) | 3030(20) | 0 | 200(30) |
| O(6) | 1270(18) | 1270(18) | 0 | 180(20) |

Experimental and Refinement Details for ZIF-11 (RHO). A colorless cubic crystal (0.08×0.08×008 mm$^3$) of ZIF-11 was placed in a 0.3 mm diameter borosilicate capillary along with a small amount of mother liquor, which was flame sealed, and mounted on a Bruker SMART APEX CCD diffractometer while being flash frozen to 233(2) K in a liquid N2 cooled stream of nitrogen. A total of 119088 reflections were collected of which 2415 were unique and 1300 were greater than 4σ(I). The range of θ was from 0.71 to 20.81°. Analysis of the data showed negligible decay during collection. The structure was solved in the cubic Pm-3m space group with Z=12 using direct methods. Atoms C7, C8, C12, C13, C14, and C16 were found to be disordered and with each group modeled as its own independent free variable. All non-hydrogen atoms were refined anisotropic ally with hydrogen atoms generated as spheres riding the coordinates of their parent atoms. To treat the diffuse electron density, a protein diffuse scattering correction (SWAT) command was applied. The two variables g and U were refined to converge at 1.1 and 3.6, respectively. Final full matrix least-squares refinement on $F^2$ converged to R1=0.0778 (F>2σF)) and wR2=0.2382 (all data) with GOF=1.006. All residual electron density in the final F-map was closely associated with the guest molecules within the pore of ZIF-11. Crystal data and structure refinement for ZIF-11: Empirical formula, C56 H40 N16 O3.77 Zn4; Formula weight, 1258.84; Temperature, 258 K; Wavelength, 0.71073 Å; Crystal system, Cubic; Space group, Pm-3m; Unit cell dimensions, a=28.7595 Å, α=90°, b=28.7595 Å, β=90°, c=28.7595 Å, γ=90°; Volume, 23787.2 $Å^3$; Z, 12; Density (calculated), 1.055 Mg/m³; Absorption coefficient, 1.238 $mm^{-1}$; F(000), 7658; Crystal size, 0.08× 0.08×0.08 $mm^3$; Theta range for data collection, 0.71 to 20.81°. Index ranges −28<=h<=28, −28<=k<=28, −28<=l<=28 Reflections collected 119088 Independent reflections 2415 [R(int)=0.1688] Completeness to theta=20.81° 96.8% Max. and min. transmission 0.9074 and 0.9074 Refinement method Full-matrix least-squares on $F^2$ Data/restraints/parameters 2415/3/195 Goodness-of-fit on $F^2$ 1.056 Final R indices [I>2sigma(I)] R1=0.0787, wR2=0.2246 R indices (all data) R1=0.1322, wR2=0.2498 Largest diff. peak and hole 0.579 and −0.395 $e.E^{-3}$.

Atomic coordinates ($\times 10^4$) and equivalent isotropic displacement parameters ($Å^2 \times 10^3$) for ZIF-11. U(eq) is defined as one third of the trace of the orthogonalized $U^{ij}$ tensor.

| | x | y | z | U(eq) |
|---|---|---|---|---|
| Zn(1) | 3962(1) | 1043(1) | 2520(1) | 95(1) |
| C(1) | 3950(4) | 0 | 2560(4) | 94(4) |
| C(2) | 3356(3) | 256(3) | 2215(3) | 96(3) |
| C(3) | 2991(4) | 500(4) | 1998(4) | 144(4) |
| C(4) | 2652(5) | 247(5) | 1803(6) | 235(9) |
| C(5) | 3908(4) | 1793(3) | 1793(3) | 98(4) |
| C(6A) | 4230(8) | 1201(7) | 1563(8) | 73(7) |
| C(7A) | 4423(7) | 744(6) | 1466(6) | 65(6) |
| C(8A) | 4611(6) | 703(6) | 1038(6) | 91(8) |
| C(6B) | 4071(8) | 1096(7) | 1447(7) | 104(8) |
| C(7B) | 4120(7) | 632(7) | 1331(7) | 102(7) |
| C(8B) | 4150(7) | 533(6) | 867(6) | 122(8) |
| C(9) | 3189(3) | 1113(5) | 3189(3) | 89(4) |
| C(10) | 3554(4) | 1738(4) | 3197(3) | 116(3) |
| C(11) | 3825(5) | 2137(5) | 3139(5) | 161(5) |
| C(12A) | 3877(15) | 2389(18) | 3503(16) | 122(19) |
| C(12B) | 3723(14) | 2564(16) | 3374(11) | 145(14) |
| C(13A) | 4747(8) | 1015(10) | 3231(4) | 64(8) |
| C(14A) | 4499(7) | 957(8) | 3647(7) | 59(7) |
| C(16A) | 4762(8) | 913(9) | 4054(9) | 96(11) |
| C(13B) | 4770(7) | 808(7) | 3169(5) | 111(7) |
| C(14B) | 4501(6) | 584(7) | 3529(6) | 134(7) |
| O(16B) | 4769(5) | 334(6) | 3857(6) | 147(8) |
| C(15) | 5000 | 1106(5) | 2533(5) | 102(4) |
| N(1) | 3751(3) | 394(3) | 2440(3) | 92(2) |
| N(2) | 3992(2) | 1358(3) | 1906(3) | 96(2) |
| N(3) | 3529(3) | 1312(3) | 2975(2) | 95(2) |
| N(4) | 4607(2) | 1022(3) | 2768(3) | 99(2) |
| O(1S) | 5000 | 2563(19) | 2563(19) | 210(20) |
| O(2S) | 4320(40) | 4320(40) | 4320(40) | 220(80) |
| O(3S) | 5000 | 2329(14) | 2329(14) | 174(18) |
| O(4S) | 5000 | 2630(30) | 3960(30) | 200(40) |
| O(5S) | 2090(30) | 535(19) | 535(19) | 200(30) |
| O(6S) | 2351(18) | 2351(18) | 2351(18) | 110(20) |
| O(7S) | 1550(40) | 1550(40) | 1550(40) | 140(60) |
| O(8S) | 5000 | 2592(7) | 3028(8) | 309(11) |

Experimental and Refinement Details for ZIF-12(RHO—Cobalt Form). A purple cubic crystal (0.08×0.08×0.08 $mm^3$) of ZIF-12 was placed in a 0.3 mm diameter borosilicate capillary along with a small amount of mother liquor, which was flame sealed, and mounted on a Bruker SMART APEX CCD diffractometer while being flash frozen to 233(2) K in a liquid N2 cooled stream of nitrogen. A total of 21631 reflections were collected of which 1204 were unique and 398 were greater than 4σ(I). The range of θ was from 0.71 to 15.94°. Analysis of the data showed negligible decay during collection, however the amount of reliable data which could be collected was very limited due to the small crystal size of this sample and its lowered crystallinity. The structure was solved in the cubic Pm-3m space group with Z=12 using direct methods. Atoms C7, C8, C13, C14, and C16 were found to be disordered and with each group modeled as its own independent free variable. All non-hydrogen (except Co) and hydrogen atoms were refined isotropically with hydrogen atoms generated as spheres riding the coordinates of their parent atoms. Cobalt atoms was refined anisotropically. It should be noted that the precision of this model is low, and is reported to demonstrate that ZIF-12 can be isolated in crystalline form. Other supporting characterization data (vide infra Materials and Methods) also support this conclusion. Final full matrix least-squares refinement on $F^2$ converged to R1=0.1064 (F>2σF)) and wR2=0.23712 (all data) with GOF=1.202. All residual electron density in the final F-map was closely associated with the guest molecules within the pore of ZIF-12. Crystal data and structure refinement for ZIF-12: Empirical formula, C13.58 H9.58 Co N4 O0.92; Formula weight, 280.176; Temperature, 258 K; Wavelength, 0.71073 Å; Crystal system, Cubic Space group, Pm-3m; Unit cell dimensions, a=28.7595 Å, α=90°, b=28.7595 Å, β=90°, c=28.7595 Å, γ=90°; Volume, 23787.2 $Å^3$, Z, 12; Density (calculated), 1.014 Mg/m³; Absorption coefficient, 0.864 $mm^{-1}$; F(000), 7366; Crystal size, 0.08×0.08×0.08 $mm^3$; Theta range for data collection, 1.00 to 15.94°. Index ranges −16<=h<=22, −21<=k<=21, −22<=l<=16 Reflections collected 21631 Independent reflections 1204 [R(int)=0.4632] Completeness to theta=15.94° 99.0% Absorption correction Semi-empirical from equivalents Max. and min. transmission 0.9341 and 0.9341 Refinement method Full-matrix least-squares on $F^2$ Data/restraints/parameters 1204/8/124 Goodness-of-fit on $F^2$ 1.202 Final R indices [I>2sigma(I)] R1=0.1064, wR2=0.3393 R indices (all data) R1=0.2328, wR2=0.3712 Largest diff. peak and hole 0.907 and −0.439 $e.E^{-3}$.

Atomic coordinates ($\times 10^4$) and equivalent isotropic displacement parameters ($Å^2 \times 10^3$) for ZIF-12. U(eq) is defined as one third of the trace of the orthogonalized $U^{ij}$ tensor.

| | x | y | z | U(eq) |
|---|---|---|---|---|
| Co(1) | 3965(2) | 1044(2) | 2515(2) | 65(3) |
| C(1) | 4001(14) | 0 | 2599(16) | 70(20) |
| C(2) | 3359(9) | 232(12) | 2221(13) | 110(20) |

-continued

| | x | y | z | U(eq) |
|---|---|---|---|---|
| C(3) | 3090(20) | 535(18) | 2010(20) | 160(20) |
| C(4) | 2663(14) | 290(20) | 1800(20) | 270(40) |
| C(5) | 3930(20) | 1793(15) | 1793(15) | 80(20) |
| C(6A) | 4270(40) | 1180(30) | 1530(30) | 20(30) |
| C(7A) | 4450(40) | 760(30) | 1460(30) | 10(30) |
| C(8A) | 4610(30) | 710(20) | 1030(30) | 40(40) |
| C(6B) | 4020(30) | 1140(30) | 1480(20) | 60(30) |
| C(7B) | 4100(30) | 690(30) | 1390(20) | 70(30) |
| C(8B) | 4140(30) | 540(20) | 880(30) | 140(50) |
| C(9) | 3203(12) | 1090(18) | 3203(12) | 52(19) |
| C(10) | 3554(12) | 1729(15) | 3194(10) | 71(14) |
| C(11) | 3848(13) | 2117(15) | 3144(14) | 78(14) |
| C(12B) | 3747(13) | 2499(16) | 3428(14) | 10(30) |
| C(13A) | 4747 | 1015 | 3231 | 64 |
| C(14A) | 4499 | 957 | 3647 | 59 |
| C(16A) | 4750(20) | 930(30) | 4060(30) | 90(40) |
| C(13B) | 4770(18) | 770(20) | 3140(20) | 50(30) |
| C(14B) | 4530(30) | 580(30) | 3480(30) | 120(40) |
| C(16B) | 4780(20) | 320(20) | 3870(20) | 90(30) |
| C(15) | 5000 | 1065(18) | 2534(18) | 54(18) |
| N(1) | 3767(8) | 385(4) | 2427(10) | 66(10) |
| N(2) | 3986(10) | 1339(10) | 1903(11) | 60(10) |
| N(3) | 3536(9) | 1301(10) | 2972(10) | 57(10) |
| N(4) | 4606(10) | 1006(11) | 2768(4) | 71(11) |
| O(1S) | 5000 | 2480(60) | 2480(60) | 110(100) |
| O(2S) | 5000 | 2340(50) | 2340(50) | 150(100) |
| O(3S) | 5000 | 2100(50) | 4190(50) | 10(50) |
| O(4S) | 2860(80) | 560(60) | 560(60) | 130(100) |
| O(5S) | 1730(60) | 1730(60) | 1730(60) | 70(120) |
| O(6S) | 24900(200) | 24900(200) | 24900(200) | 0(600) |
| O(7S) | 5000 | 2620(20) | 3060(30) | 320(40) |

Experimental and Refinement Details for ZIF-20 and -21. For ZIF-21 all non-hydrogen (except Co) and hydrogen atoms were refined isotropically. Cobalt atoms were refined anisotropically. ZIF-20 can be isolated in crystalline form. Note that the same solvent disorder model was employed for this structure as was for ZIF-20. Crystal data and structure refinement for ZIF-20: Empirical formula C20 H12 N16 O8.88 Zn2; Formula weight 749.20; Temperature 153 K; Wavelength 1.54178 Å; Crystal system, Cubic; Space group, Fm-3m; Unit cell dimensions, a=45.4725 Å, α=90°, b=45.4725 Å, β=90°, c=45.4725 Å, γ=90°; Volume 94025.7 Å$^3$, Z, 96; Density (calculated), 1.270 Mg/m$^3$; absorption coefficient 2.027 mm$^{-1}$; F(000) 36000; Crystal size, 0.20×0.20×0.15 mm$^3$; Theta range for data collection 1.68 to 50.37°. Index ranges −45<=h<=36, −40<=k<=33, −43<=l<=41; Reflections collected 34673; Independent reflections 2446 [R(int)=0.0466]; Completeness to theta=50.37° 99.6%; Absorption correction Semi-empirical from equivalents; Max. and min. transmission 0.742 and 0.706; Refinement method Full-matrix least-squares on F$^2$; Data/restraints/parameters: 2446/0/184; Goodness-of-fit on F$^2$ 1.467; Final R indices [I>2sigma(I)] R1=0.0871, wR2=0.3160; R indices (all data) R1=0.0949, wR2=0.3261; Largest diff. peak and hole 1.717 and −0.805 e.Å$^{-3}$ Atomic coordinates (×10$^4$) and equivalent isotropic displacement parameters (Å$^2$×10$^3$) for ZIF-20. U(eq) is defined as one third of the trace of the orthogonalized U$^{ij}$ tensor.

| | x | y | z | U(eq) |
|---|---|---|---|---|
| C(1) | 2971(1) | 2029(1) | 689(2) | 57(2) |
| C(2) | 2988(1) | 2229(1) | 1108(2) | 58(2) |
| C(3) | 3046(2) | 2392(2) | 1348(2) | 100(4) |
| N(5) | 2875(2) | 2328(3) | 1581(2) | 147(5) |
| N(6) | 3046(2) | 2392(2) | 1348(2) | 100(4) |
| C(4) | 2875(2) | 2328(3) | 1581(2) | 147(5) |

-continued

| | x | y | z | U(eq) |
|---|---|---|---|---|
| C(5) | 3379(2) | 2484(2) | 0 | 49(3) |
| C(6) | 3606(2) | 2105(2) | 151(1) | 71(2) |
| C(7) | 3734(2) | 1890(2) | 310(2) | 131(5) |
| N(7) | 3852(3) | 1675(2) | 140(2) | 220(8) |
| N(8) | 3734(2) | 1890(2) | 310(2) | 131(5) |
| C(8) | 3852(3) | 1675(2) | 140(2) | 220(8) |
| C(9) | 3873(2) | 2454(2) | 1127(2) | 53(2) |
| C(10) | 4072(1) | 2564(2) | 715(2) | 56(2) |
| C(11) | 4130(2) | 2642(2) | 430(1) | 86(3) |
| N(9) | 4420(2) | 2710(2) | 378(1) | 101(3) |
| N(10) | 4130(2) | 2642(2) | 430(1) | 86(3) |
| C(12) | 4420(2) | 2710(2) | 378(1) | 101(3) |
| C(13) | 2962(1) | 2962(1) | 640(2) | 46(2) |
| C(14) | 3380(1) | 3167(1) | 695(1) | 65(2) |
| C(15) | 3673(2) | 3232(2) | 729(2) | 94(3) |
| N(11) | 3726(2) | 3522(2) | 754(2) | 107(4) |
| N(12) | 3673(2) | 3232(2) | 729(2) | 94(3) |
| C(16) | 3726(2) | 3522(2) | 754(2) | 107(4) |
| N(1) | 3118(1) | 2234(1) | 838(1) | 54(2) |
| N(2) | 3459(1) | 2348(1) | 249(1) | 57(1) |
| N(3) | 3806(1) | 2491(1) | 843(1) | 56(2) |
| N(4) | 3248(1) | 2894(1) | 657(1) | 55(1) |
| O(1) | 3197 | 3197 | 0 | 80 |
| O(2) | 2500 | 2500 | 2500 | 144 |
| O(3) | 3335 | 3335 | 1665 | 146 |
| O(4) | 3246 | 3839 | 0 | 223 |
| O(5) | 3565 | 3565 | 0 | 251 |
| O(6) | 2500 | 2500 | 244 | 248 |
| O(7) | 2500 | 2500 | 737 | 500 |
| O(8) | 0 | 5000 | 0 | 407 |
| O(9) | 5000 | 3279 | 0 | 335 |
| O(10) | 4294 | 4294 | 706 | 486 |
| O(11) | 2500 | 2500 | 0 | 591 |
| O(12) | 3758 | 3758 | 0 | 367 |
| O(13) | 2860 | 3762 | 0 | 905 |
| O(14) | 1923 | 3077 | 0 | 982 |
| O(15) | 2973 | 3495 | 1505 | 238 |
| O(17) | 5000 | 3464 | 0 | 1011 |
| O(18) | 2855 | 2855 | 2145 | 874 |
| O(19) | 3387 | 1613 | 1613 | 257 |
| O(20) | 3340 | 3471 | 0 | 312 |
| Zn(1) | 3417(1) | 2495(1) | 656(1) | 54(1) |

Crystal data and structure refinement for ZIF-21: Empirical formula, C20 H12 Co2 N16 O8.88; Formula weight 736.32; Temperature, 153 K; Wavelength, 1.54178 Å; Crystal system, Cubic; Space group, Fm-3m; Unit cell dimensions a=45.4725 Å, α=90°, b=45.4725 Å, β=90°, c=45.4725 Å, γ=90°; Volume, 94025.7 Å$^3$, Z, 96; Density (calculated), 1.248 Mg/m$^3$; Absorption coefficient 7.154 mm$^{-1}$; F(000), 35424; Crystal size, 0.20×0.10×0.10 mm$^3$; Theta range for data collection, 1.68 to 30.87°; Index ranges, −30<=h<=29, −30<=k<=30, −29<=l<=30; Reflections collected 47463; Independent reflections, 794 [R(int)=0.0818]; Completeness to theta=30.87°, 100.0%; Absorption correction, Semi-empirical from equivalents; Refinement method, Full-matrix least-squares on F$^2$; Data/restraints/parameters, 794/1/91; Goodness-of-fit on F$^2$ 2.636; Final R indices, [I>2sigma(I)] R1=0.1386, wR2=0.4752; R indices (all data) R1=0.1423, wR2=0.4838; Largest diff. peak and hole 0.663 and −0.788 e.Å$^{-3}$ Atomic coordinates (×10$^4$) and equivalent isotropic displacement parameters (Å$^{2\times 10^3}$) for ZIF-21. U(eq) is defined as one third of the trace of the orthogonalized U$^{ij}$ tensor.

| | x | y | z | U(eq) |
|---|---|---|---|---|
| C(1) | 2980(2) | 2020(2) | 687(2) | 48(4) |
| C(2) | 2987(1) | 2227(2) | 1108(2) | 42(3) |

| | x | y | z | U(eq) |
|---|---|---|---|---|
| C(3) | 3048(2) | 2389(2) | 1352(2) | 70(3) |
| N(5) | 2866(2) | 2335(2) | 1582(2) | 141(4) |
| N(6) | 3048(2) | 2389(2) | 1352(2) | 70(3) |
| C(4) | 2866(2) | 2335(2) | 1582(2) | 141(4) |
| C(5) | 3376(3) | 2487(2) | 0 | 38(4) |
| C(6) | 3605(2) | 2095(2) | 153(2) | 63(3) |
| C(7) | 3728(2) | 1877(2) | 311(2) | 104(4) |
| N(7) | 3865(2) | 1678(2) | 143(2) | 178(5) |
| N(8) | 3728(2) | 1877(2) | 311(2) | 104(4) |
| C(8) | 3865(2) | 1678(2) | 143(2) | 178(5) |
| C(9) | 3880(2) | 2453(2) | 1120(2) | 49(5) |
| C(10) | 4073(2) | 2561(2) | 718(2) | 49(4) |
| C(11) | 4127(2) | 2652(2) | 437(2) | 90(3) |
| N(9) | 4423(2) | 2721(2) | 379(1) | 66(3) |
| N(10) | 4127(2) | 2652(2) | 437(2) | 90(3) |
| C(12) | 4423(2) | 2721(2) | 379(1) | 66(3) |
| C(13) | 2965(1) | 2965(1) | 633(2) | 50 |
| C(14) | 3380(1) | 3170(1) | 698(2) | 60(3) |
| C(15) | 3676(2) | 3226(2) | 727(2) | 63(3) |
| N(11) | 3725(2) | 3523(2) | 760(2) | 119(4) |
| N(12) | 3676(2) | 3226(2) | 727(2) | 63(3) |
| C(16) | 3725(2) | 3523(2) | 760(2) | 119(4) |
| N(1) | 3122(1) | 2232(1) | 835(1) | 40(2) |
| N(2) | 3458(1) | 2349(2) | 253(1) | 44(2) |
| N(3) | 3810(2) | 2493(1) | 837(1) | 43(3) |
| N(4) | 3247(1) | 2894(1) | 661(1) | 51(2) |
| O(1) | 3197 | 3197 | 0 | 80 |
| O(2) | 2500 | 2500 | 2500 | 144 |
| O(3) | 3335 | 3335 | 1665 | 146 |
| O(4) | 3246 | 3839 | 0 | 223 |
| O(5) | 3565 | 3565 | 0 | 251 |
| O(6) | 2500 | 2500 | 244 | 248 |
| O(7) | 2500 | 2500 | 737 | 2000 |
| O(8) | 0 | 5000 | 0 | 407 |
| O(9) | 5000 | 3279 | 0 | 335 |
| O(10) | 4294 | 4294 | 706 | 486 |
| O(11) | 2500 | 2500 | 0 | 591 |
| O(12) | 3758 | 3758 | 0 | 367 |
| O(13) | 2860 | 3762 | 0 | 905 |
| O(14) | 1923 | 3077 | 0 | 982 |
| O(15) | 2973 | 3495 | 1505 | 238 |
| O(17) | 5000 | 3464 | 0 | 1011 |
| O(18) | 2855 | 2855 | 2145 | 874 |
| O(19) | 3387 | 1613 | 1613 | 257 |
| O(20) | 3340 | 3471 | 0 | 312 |
| Co(1) | 3416(1) | 2494(1) | 656(1) | 48(1) |

Experimental and Refinement Details for ZIF-22. Crystal data and structure refinement for ZIF-22: Empirical formula, C24 H16 N12 O8.33 Zn2; Formula weight, 736.56; Temperature, 293 K; Wavelength, 1.54178 Å; Crystal system, Cubic; Space group, Fm-3m; Unit cell dimensions, a=45.6001 Å, α=90°, b=45.6001 Å, β=90°, c=45.6001 Å, γ=90°; Volume, 94819.4 Å$^3$, Z, 96; Density (calculated), 1.238 Mg/m$^3$; Absorption coefficient, 1.960 mm$^{-3}$; F(000), 35584; Crystal size, 0.16×014×013 mm$^3$; Theta range for data collection, 1.68 to 50.44°; Index ranges, −45<=h<=45, −40<=k<=45, −45<=l<=43; Reflections collected, 101868; Independent reflections, 2456 [R(int)=0.1384]; Completeness to theta=50.44° 99.1%; Refinement method, Full-matrix least-squares on F$^2$; Data/restraints/parameters, 2456/0/213; Goodness-of-fit on F$^2$ 1.355; Final R indices [I>2sigma(I)] R1=0.1087, wR2=0.3634; R indices (all data) R1=0.1402, wR2=0.4071; Largest diff. peak and hole 2.663 and −0.835 e.Å$^{-3}$.

Atomic coordinates (×10$^4$) and equivalent isotropic displacement parameters (Å$^2$×10$^3$) for ZIF-22. U(eq) is defined as one third of the trace of the orthogonalized U$^{ij}$ tensor.

| | x | y | z | U(eq) |
|---|---|---|---|---|
| C(1) | 2030(2) | 2030(2) | 687(3) | 67(4) |
| C(2) | 2238(2) | 2019(2) | 1104(2) | 59(3) |
| C(3) | 2395(3) | 1968(3) | 1347(3) | 92(4) |
| C(4) | 2353(3) | 2128(3) | 1585(3) | 117(4) |
| N(5) | 2353(3) | 2128(3) | 1585(3) | 117(4) |
| C(5) | 2483(3) | 1625(3) | 0 | 60(4) |
| C(6) | 2109(3) | 1386(2) | 153(2) | 78(4) |
| C(7) | 1880(3) | 1246(3) | 282(4) | 123(5) |
| C(8) | 1664(3) | 1139(4) | 139(3) | 167(8) |
| N(6) | 1664(3) | 1139(4) | 139(3) | 167(8) |
| C(9) | 2969(2) | 2031(2) | 656(3) | 60(4) |
| C(10) | 3173(2) | 1614(2) | 679(2) | 75(3) |
| C(11) | 3246(3) | 1331(3) | 708(3) | 116(5) |
| C(12) | 3529(3) | 1249(3) | 728(3) | 128(5) |
| N(7) | 3529(3) | 1249(3) | 728(3) | 128(5) |
| C(13) | 2447(3) | 1123(3) | 1123(2) | 63(4) |
| C(14) | 2547(3) | 928(2) | 718(2) | 69(3) |
| C(15) | 2610(3) | 851(3) | 431(2) | 102(4) |
| C(16) | 2679(3) | 584(3) | 364(2) | 114(4) |
| N(8) | 2679(3) | 584(3) | 364(2) | 114(4) |
| N(1) | 2237(2) | 1891(2) | 830(2) | 71(3) |
| N(2) | 2348(2) | 1537(2) | 248(2) | 67(2) |
| N(3) | 2898(2) | 1747(2) | 663(2) | 66(2) |
| N(4) | 2476(2) | 1193(2) | 847(2) | 65(3) |
| O(1) | 1474(7) | 1474(7) | 1474(7) | 270(20) |
| O(2) | 2500 | 2500 | 366(11) | 243(18) |
| O(5) | 1871(8) | 3129(8) | 1871(8) | 290(20) |
| O(6) | 3487(8) | 1513(8) | 0 | 275(17) |
| O(9) | 3237(6) | 1763(6) | 0 | 208(11) |
| O(10) | 1662(4) | 3338(4) | 1662(4) | 130(8) |
| O(11) | 2500 | 2500 | 0 | 320(40) |
| O(12) | 3773(7) | 1797(8) | 0 | 328(16) |
| O(13) | 1657(6) | 1657(6) | 1657(6) | 206(14) |
| O(14) | 3665(8) | 1098(9) | 0 | 410(20) |
| O(15) | 3430(20) | 0 | 0 | 460(50) |
| O(16) | 1915(12) | 3085(12) | 2318(18) | 640(50) |
| O(17) | 2044(8) | 3546(5) | 1454(5) | 330(16) |
| O(18) | 2960(30) | 2040(30) | 0 | 830(140) |
| O(21) | 2754(15) | 2246(15) | 0 | 420(30) |
| Zn(1) | 2498(1) | 1588(1) | 655(1) | 66(1) |

Experimental and Refinement Details for ZIF-23. Crystal data and structure refinement for ZIF-23: Empirical formula, C12 H8 N6 Zn; Formula weight, 301.61; Temperature, 153 K; Wavelength, 1.54178 Å; Crystal system, Orthorhombic; Space group, P212121; Unit cell dimensions, a=9.5477 Å, α=90°, b=10.1461 Å, β=90°, c=12.4459 Å, γ=90°; Volume, 1205.66 Å$^3$, Z, 4; Density (calculated), 1.662 Mg/m$^3$; Absorption coefficient, 2.791 mm$^{-1}$; F(000), 608; Crystal size, 0.11×0.05×0.03 mm$^3$; Theta range for data collection, 5.63 to 50.41°. Index ranges, −9<=h<=9, −10<=k<=9, −10<=l<=12; Reflections collected, 5183; Independent reflections, 1257 [R(int)=0.0706]; Completeness to theta=50.41° 99.3%; Absorption correction, Semi-empirical from equivalents; Max. and min. transmission, 0.9111 and 0.7470; Refinement method, Full-matrix least-squares on F$^2$; Data/restraints/parameters, 1257/0/172; Goodness-of-fit on F$^2$ 0.783; Final R indices [I>2sigma(I)] R1=0.0242, wR2=0.0618; R indices (all data) R1=0.0271, wR2=0.0640; Absolute structure parameter −0.06(4); Largest diff. peak and hole 0.159 and −0.171 e.Å$^{-3}$.

Atomic coordinates (×10$^4$) and equivalent isotropic displacement parameters (Å$^2$×10$^3$) for ZIF-23. U(eq) is defined as one third of the trace of the orthogonalized U$^{ij}$ tensor.

| | x | y | z | U(eq) |
|---|---|---|---|---|
| C(1) | 1960(5) | 2496(5) | 4975(4) | 24(1) |
| C(2) | 513(5) | 3547(4) | 3990(3) | 23(1) |
| C(3) | −474(7) | 4604(5) | 2605(5) | 53(2) |

-continued

| | x | y | z | U(eq) |
|---|---|---|---|---|
| C(4) | 636(8) | 4263(6) | 1933(4) | 54(2) |
| C(5) | −3260(5) | 1489(5) | 7697(3) | 31(1) |
| C(6) | −3324(4) | 1824(4) | 6641(3) | 23(1) |
| C(7) | 70(5) | 802(4) | 7483(4) | 22(1) |
| C(8) | 1532(4) | 1108(4) | 8783(3) | 20(1) |
| C(9) | 2454(5) | 1034(4) | 9622(4) | 27(1) |
| C(10) | 3109(6) | 2218(5) | 9877(5) | 42(2) |
| C(11) | 2823(5) | 3367(6) | 9305(4) | 47(1) |
| C(12) | 1326(5) | 2297(4) | 8238(3) | 23(1) |
| N(1) | 718(4) | 3092(3) | 5020(3) | 23(1) |
| N(2) | −2402(4) | 2502(3) | 5978(3) | 23(1) |
| N(3) | −722(4) | 5152(3) | 6727(2) | 21(1) |
| N(4) | 368(4) | 2097(3) | 7416(3) | 22(1) |
| N(5) | −583(4) | 4254(4) | 3643(3) | 41(1) |
| N(6) | 1912(4) | 3454(4) | 8487(3) | 41(1) |
| Zn(1) | −509(1) | 3268(1) | 6317(1) | 19(1) |

Powder X-ray diffraction (PXRD) data were collected using a Bruker D8-Advance θ-2θ diffractometer in reflectance Bragg-Brentano geometry employing Ni filtered Cu Kα line focused radiation at 1600 W (40kV, 40 mA) power and equipped with a Na(Tl) scintillation detector fitted a 0.2 mm radiation entrance slit. All samples were ground to ensure mono-dispersity in the bulk, then mounted onto a zero-background sample holder by dropping powders from a wide-blade spatula and then leveling the sample surface with a razor blade. The best counting statistics were achieved by using a 0.02° 2θ step scan from 1.5-60° with an exposure time of 10 s per step.

Comparison of positions and indices of diffraction lines in the experimental and simulated PXRD patterns of ZIF-1(crb). Deviations from perfect correspondence primarily arise from difference in data collection temperatures (cryogenic for single crystal data and room temperature for bulk powder):

| Observed PXRD | | Simulated PXRD | | Indices |
|---|---|---|---|---|
| 2-Theta | d | 2-Theta | d | hkl |
| 10.16 | 8.698 | 10.18 | 8.684 | −101 |
| 11.19 | 7.899 | 11.71 | 7.548 | −1-11 |
| 11.93 | 7.384 | 11.98 | 7.384 | 002 |
| 12.96 | 6.825 | 13.05 | 6.781 | 021 |
| 13.26 | 6.674 | 13.31 | 6.647 | 012 |
| 15.02 | 5.893 | 15.12 | 5.852 | −112 |
| 15.39 | 5.753 | 15.44 | 5.733 | −1-21 |
| 16.42 | 5.394 | 16.48 | 5.373 | 121 |
| 16.64 | 5.323 | 16.69 | 5.307 | 022 |
| 17.23 | 5.142 | 17.19 | 5.155 | 112 |
| 18.34 | 4.835 | 18.41 | 4.815 | 200 |
| 25.04 | 3.554 | 25.08 | 3.548 | 140 |

Comparison of positions and indices of diffraction lines in the experimental and simulated PXRD patterns of ZIF-4 (cag). Deviations from perfect correspondence primarily arise from difference in data collection temperatures (cryogenic for single crystal data and room temperature for bulk powder):

| Observed PXRD | | Simulated PXRD | | Indices |
|---|---|---|---|---|
| 2-Theta | d | 2-Theta | d | hkl |
| 9.38 | 9.420 | 9.45 | 9.353 | 111 |
| 11.03 | 8.019 | 11.18 | 7.906 | 102 |
| 11.37 | 7.778 | 11.55 | 7.654 | 020 |
| 12.53 | 7.058 | 12.51 | 7.068 | 021 |
| 12.60 | 7.020 | 12.59 | 7.024 | 112 |
| 13.63 | 6.493 | 13.77 | 6.423 | 121 |
| 14.86 | 5.957 | 14.98 | 5.907 | 202 |
| 16.09 | 5.503 | 16.07 | 5.511 | 212 |
| 16.50 | 5.367 | 16.57 | 5.345 | 113 |
| 16.84 | 5.259 | 17.01 | 5.206 | 221 |
| 18.22 | 4.866 | 18.51 | 4.790 | 023 |
| 18.76 | 4.726 | 18.85 | 4.704 | 311 |
| 19.24 | 4.609 | 19.25 | 4.606 | 004 |

Comparison of positions and indices of diffraction lines in the experimental and simulated PXRD patterns of ZIF-7 (sod). Deviations from perfect correspondence primarily arise from difference in data collection temperatures (cryogenic for single crystal data and room temperature for bulk powder):

| Observed PXRD | | Simulated PXRD | | Indices |
|---|---|---|---|---|
| 2-Theta | d | 2-Theta | d | hkl |
| 7.12 | 12.413 | 7.14 | 12.358 | −111 |
| 7.60 | 11.629 | 7.68 | 11.494 | 110 |
| 12.16 | 7.271 | 12.07 | 7.329 | 012 |
| 13.21 | 6.691 | 13.33 | 6.636 | 030 |
| 15.29 | 5.791 | 15.41 | 5.747 | 220 |
| 16.25 | 5.450 | 16.27 | 5.443 | −132 |
| 18.61 | 4.765 | 18.55 | 4.779 | 113 |
| 19.57 | 4.533 | 19.61 | 4.522 | 312 |
| 21.11 | 4.206 | 21.09 | 4.208 | 042 |
| 21.64 | 4.104 | 21.55 | 4.119 | −333 |
| 22.93 | 3.875 | 22.91 | 3.878 | −243 |
| 31.78 | 2.814 | 31.87 | 2.806 | −663 |

Comparison of positions and indices of diffraction lines in the experimental and simulated PXRD patterns of ZIF-8 (sod). Deviations from perfect correspondence primarily arise from difference in data collection temperatures (cryogenic for single crystal data and room temperature for bulk powder).

| Observed PXRD | | Simulated PXRD | | Indices |
|---|---|---|---|---|
| 2-Theta | d | 2-Theta | d | hkl |
| 7.31 | 12.085 | 7.35 | 12.015 | 011 |
| 10.24 | 8.629 | 10.40 | 8.496 | 002 |
| 12.65 | 6.994 | 12.75 | 6.937 | 112 |
| 14.67 | 6.035 | 14.73 | 6.007 | 022 |
| 16.03 | 5.433 | 16.48 | 5.373 | 013 |
| 17.84 | 4.905 | 18.07 | 4.905 | 222 |
| 22.02 | 4.033 | 22.18 | 4.005 | 114 |
| 24.38 | 3.648 | 24.55 | 3.623 | 233 |
| 26.64 | 3.343 | 26.73 | 3.332 | 134 |
| 29.72 | 3.004 | 29.72 | 3.004 | 044 |
| 30.44 | 2.934 | 30.65 | 2.914 | 334 |
| 31.69 | 2.821 | 31.57 | 2.832 | 244 |
| 32.41 | 2.760 | 32.46 | 2.756 | 235 |

Comparison of positions and indices of diffraction lines in the experimental and simulated PXRD patterns of ZIF-11 (rho). Deviations from perfect correspondence primarily arise from difference in data collection temperatures (cryogenic for single crystal data and room temperature for bulk powder).

| Observed PXRD | | Simulated PXRD | | Indices |
|---|---|---|---|---|
| 2-Theta | d | 2-Theta | d | Hkl |
| 3.09 | 28.564 | 3.07 | 28.759 | 001 |
| 4.31 | 20.466 | 4.34 | 20.336 | 011 |
| 6.03 | 14.655 | 6.14 | 14.380 | 002 |
| 7.53 | 11.727 | 7.52 | 11.741 | 112 |
| 8.63 | 10.240 | 8.69 | 10.168 | 022 |
| 9.72 | 9.089 | 9.72 | 9.095 | 013 |
| 11.09 | 7.970 | 11.08 | 7.977 | 023 |
| 12.33 | 7.175 | 12.30 | 7.190 | 004 |
| 12.74 | 6.945 | 12.68 | 6.975 | 223 |
| 13.01 | 6.799 | 13.05 | 6.779 | 033 |
| 13.83 | 6.3971 | 13.76 | 6.431 | 024 |
| 15.75 | 5.622 | 15.70 | 5.640 | 015 |
| 17.05 | 5.196 | 17.42 | 5.084 | 044 |
| 18.42 | 4.813 | 18.50 | 4.793 | 006 |

ZIF-7, 8, and 11 were tested for their stability in benzene, methanol and water. These solvents were chosen to compare the relative effects of non-polar to polar solvents. The tests were performed at room temperature, 50° C. and at the boiling point of each solvent (methanol 65° C., benzene 80° C. and water 100° C.) for up to 7 days. The structural stability of the frameworks were monitored by aliquoting portions of the samples for PXRD analysis after every 24 hour period.

All samples were run on a TA Instruments Q-500 series thermal gravimetric analyzer with samples held in platinum pans in a continuous flow nitrogen atmosphere. Samples were heated at a constant rate of 5° C./min during all TGA experiments.

Treatment with methanol or dichloromethane simplified the thermogravimetric behavior of ZIF-8, indicative of effective solvent-exchange. In particular, in the TGA trace of methanol-exchanged ZIF-8 sample, the original gradual weight-loss step of 28.3% up to 450° C. were replaced by a very small initial step at near-ambient temperature, a plateau up to 200° C. and a gradual step of 7.6% in the temperature range 200-450° C. ZIF-11 could be much more effectively solvent-exchanged, in the case of methanol-exchanged sample whose TGA trace only showed a tiny weight-loss step of 0.4% in the temperature range 150-250° C. Once again, ZIF-11 appears to be a more dynamic structure than ZIF-8.

All low-pressure gas-sorption experiments (up to 1 atm) were performed on a Quantachrome Autosorb-1C automatic volumetric instrument. High-pressure hydrogen sorption experiments (up to 80 bar) were performed on a VTI HPA-100 volumetric instrument equipped with a home-made liquid nitrogen cooling system to sustain a constant coolant bath level. The compressibility factors of high-pressure gases were determined by using the NIST RefProp program (version 7.0) and the NIST Standard Reference Data Base 23 (for details of high-pressure hydrogen sorption measurements, see Wong-Foy, A. G., Matzger, A. J. & Yaghi, O. M. (2006) *J. Am. Chem. Soc.* 128, 3494-3495).

Figure 35:
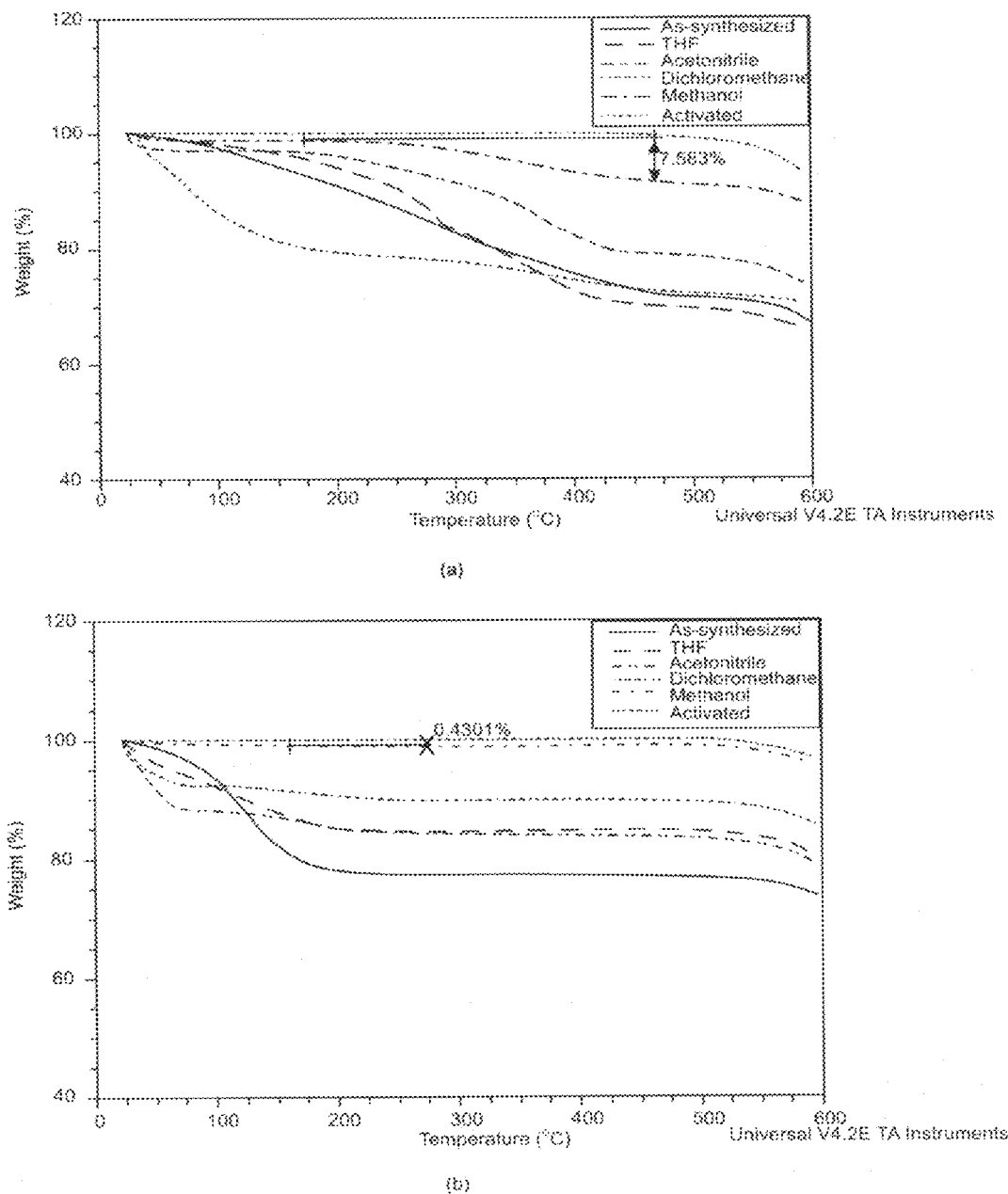
FIG. 35 shows The overlay of TGA traces of as-synthesized, solvent-exchanged, and evacuated (activated) samples of (a) ZIF-8 and (b) ZIF-11.

In light of the TGA results shown in the previous section, ZIF-8 and ZIF-11 were evacuated in the following way prior to gas-sorption analysis. The as-synthesized ZIF samples were immersed in methanol at ambient temperature for 48 hours, evacuated at ambient temperature for 5 h, then at an elevated temperature (300° C. for ZIF-8, 180° C. for ZIF-11) for 2 h. ZIF samples thus obtained were optimally evacuated, as evidenced by their well-maintained PXRD patterns and the long plateau (ambient temperature to 550° C.) in their TGA traces, shown in FIG. 35.

The microporous nature of evacuated ZIF-8 was proven by this compound's Type I nitrogen sorption isotherm. In the logarithmic-scale plot of the same isotherm, two consecutive N2 uptake steps in the micropore region were revealed, occurring at $P/P0=1\times10^{-4}-2\times10^{-3}$ and $5\times10^{-3}-1\times10^{-2}$, respectively. The two-step feature was found in the argon sorption isotherm at 87 K for ZIF-8 as well. Interestingly, the two steps in the argon isotherm were much more separated, occurring at $P/P0=1\times10^{-3}-3\times10^{-3}$ and 0.25-0.35, respectively. With the latter step being a quite steep hysteresis loop, this argon isotherm should be classified as a typical Type IV. However, the hysteresis loop cannot be explained by capillary condensation of argon into mesopores because of its low closure point, and more importantly, because of the lack of any step and hysteresis feature in the mesopore range of the nitrogen isotherm for ZIF-8. Neither is it plausible to attribute the two-step features to a change in the structure of ZIF-8 that allows further accommodation of significant amount of gas molecules because such effect was not observed in ZIF-11, which has been shown to be a more dynamic structure than ZIF-8 at elevated temperatures or in solvents. Therefore, the two-step features in both nitrogen and argon isotherms as a result of a rearrangement of the adsorbed gas molecules occurred at a certain threshold pressure, and this effect is significant in the case of ZIF-8 because its aperture size is very close to the sizes of nitrogen and argon molecules. Further, the large difference between the threshold pressures for the second steps in nitrogen and argon isotherms could be due to the different polarizabilities and molecular shapes of nitrogen and argon, which in turn determine how the adsorbed gas molecules distribute and rearrange after the completion of the first steps.

Apparent surface areas of 1,810 m$^2$/g (Langmuir) and 1,630 m$^2$/g (BET) for ZIF-8 were obtained by using the data points on the adsorption branch in the range of P/P0=0.01-0.10, and a micropore volume of 0.636 cm$^3$/g for ZIF-8 was obtained based on a single data point at P/P0=0.10. The linearity of fitting to Langmuir equation is 1.000000, to BET equation is 0.999710, and the C constant derived from BET equation is −663. Therefore, Langmuir model appears to be more suitable for evaluating the surface area of ZIF-8.

Using the data points on the nitrogen isotherm in the range of $P/P0=7\times10^{-4}-4\times10^{-3}$, i.e. at the completion of the first step, a Langmuir surface area of 1334 m$^2$/g (linearity 0.999997), a BET surface area of 1328 m$^2$/g (linearity 0.999998, C constant 3900), and a micropore volume of 0.443 cm$^3$/g (at $P/P0=4\times10^{-3}$) were obtained. Using the data points on the argon isotherm in the range of $P/P0=5\times10^{-3}-5\times10^{-2}$, i.e. at the completion of the first step, a Langmuir surface area of 1430 m$^2$/g (linearity 0.999996), a BET surface area of 1353 m$^2$/g (linearity 0.999961, C constant -7890), and a micropore volume of 0.481 (at P/P0=0.10) were obtained. The values derived from nitrogen isotherm and argon isotherm match well. Using a single data point on the adsorption branch of argon isotherm at P/P=0.42, i.e. at the completion of the second step, a micropore volume of 0.656 cm$^3$/g was obtained. Again, the value matches the one derived from the counterparts in the nitrogen isotherm. These calculations show the similarity between the two-step features in nitrogen and argon isotherms.

Figure 36:
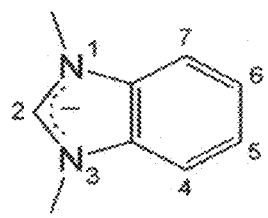
FIG. 36 depicts the position of the nitrogen atoms in the imidazolate-type linkers is significant in the selection of which zeolite imidazolate framework (ZIF) topology (SOD, RHO, dia, and LTA) is produced. The numbering of all linkers is the same as indicated for benzimidazolate.
Figure 36:
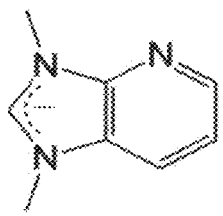
Figure 36:
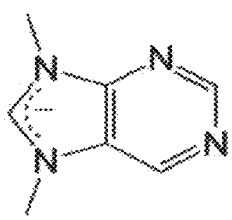
Figure 36:
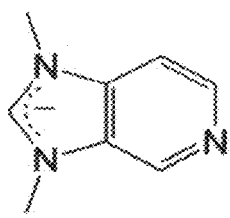

For materials with both the RHO and SOD zeolite topologies, the same framework composition is obtained using benzimidazolate as a linker (FIG. 36). In each of these structures there is one type of cage. In efforts to prepare a ZIF with zeolite A (LTA) topology, which has two type of cages (α and β), replacing key carbon atom positions with nitrogen had a profound impact on whether or not an LTA structure is achieved (FIG. 36). Replacing carbon in position 4 of benzimidazolate gave ZIF-23 with a diamond dia topology. However, replacing carbon atoms in position(s) 5 or 5 and 7 gave ZIFs based on LTA structures. These positions are ideally suited for introducing link-link interactions and together with the geometric control imparted by the nitrogen atoms in positions 1 and 3 direct the structure specifically to LTA (FIG. 36). This approach is a new way to exploit structure-directing agents which also serve as linkers in contrast to the addition of alkylammonium ions and some organic molecules that are well studied in the synthesis of aluminosilicate zeolites.

The ZIFs with LTA topology were synthesized by a solvothermal reaction of $Zn(NO_3)_2 \cdot 4H_2O$ or $Co(NO_3)_2 \cdot 6H_2O$ and excess amount of purine in N,N-dimethylformamide (DMF) at 65° C. or 85° C., respectively, to give crystalline $Zn(Pur)_2 \cdot (DMF)_{0.75}(H_2O)_{1.5}$ (ZIF-20, Pur=purinate) and its Co(II) analogue (ZIF-21).

Figure 37:
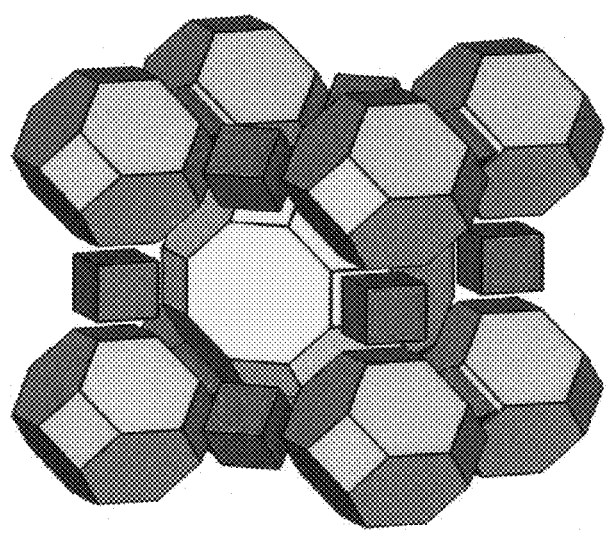
FIG. 37 depicts cage constituents of the LTA topology. The structure is shown as an exploded tiling of cubes, truncated octahedral and truncated cuboctahedra.
Figure 38:
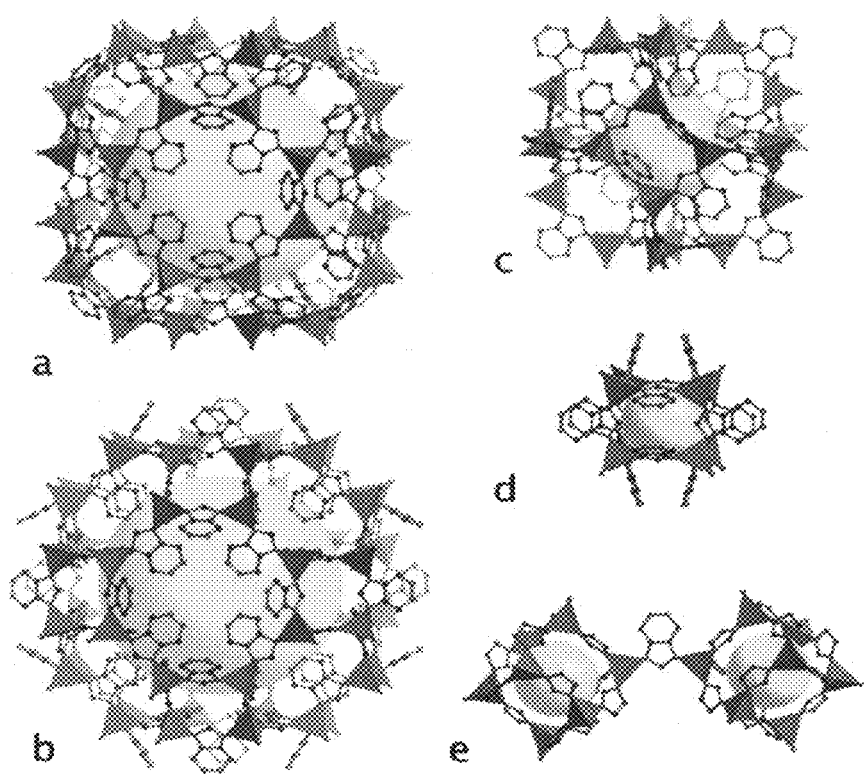
FIG. 38A-E show an X-ray single crystal structure of ZIF-20 having the same LTA topology as zeolite A. Here the oxygen and silicon atoms in zeolite A are replaced by benzimidazolates and tetrahedral zinc atoms, respectively, to give an expanded two α-cages, a and b, β-cage, c, and cube, d. Linkage between two cubes, e, is important in the reticulation of the structure. Notice the close approach of pairs of C/N atoms. $ZnN_4$ tetrahedra, carbon and nitrogen.

The framework of the LTA structure is illustrated in FIG. 37, which shows just the vertices (T atoms) and edges (links between the T atoms). It is simply made up of a tiling of cubes, truncated octahedra (β-cages), and truncated cuboctahedra (α-cages) in the ratio 3:1:1. In ZIF-20, the T atoms are Zn and the linkers are Pur bonding to Zn via the N atoms of the five-membered imidazolate ring (FIG. 38). In this structure the linkers are disordered. The N and C atoms in the 6-membered ring span a crystallographic mirror plane perpendicular to the ring, therefore C and N atoms are indistinguishable. A cubic unit cell of ZIF-20 with a=45.4725 Å contains 192 zinc ions within a unit cell volume of 94025.7(7) Å$^3$. The density (T/V) of metal atoms per unit volume is 2.04 nm$^{-3}$ which is much less than that of zeolite A (12.9 nm$^{-3}$). An identical structure was found for ZIF-21 in which Co replaces Zn.

FIG. 38 shows the separate cages in the structure of ZIF-20; notice that, because of the way the Pur linkers are oriented, there are two kinds of α-cage as depicted in FIGS. 38a and 38b. The α-cage comprises 48 Zn and 72 Pur (360 C, 216 H, 288 N). The large pore with a diameter of 14.5 Å (FIG. 38a) or 15.4 Å (FIG. 38b) is surrounded by twelve 8-membered rings, eight 12-membered rings, and six 16-membered rings, in which Zn and C atoms in position 2 of Pur were taken as points on rings. The largest 16-membered ring has a pore aperture of 2.8 Å in diameter. The T . . . T distance (ca. 5.9 Å) in ZIF-20 is extended by replacement of oxide ion into imidazolate linker (the corresponding Si . . . Si distance in an aluminosilicate is ca. 3.0 Å), which resulted in the larger maximum pore size of the α-cage compared to that in zeolite A (11.4 Å). The β-cage [24 Zn and 36 Pur (180 C, 108 H, 144 N)] (FIG. 38c) and the cube [8 Zn and 12 Pur (60 C, 36 H, 48 N)] (FIG. 38d) have smaller cavities (5.3 and 4.5 Å, respectively) and smaller pore aperture (2.0 Å and 1.5 Å, respectively). Thus the β-cage can be accessed by some small molecules through the 16-membered window.

In order to elucidate the reason for the production of the LTA topology rather than the SOD and RHO (both obtained with benzimidazolate), either 4-azabenzimidazolate or 5-azabenzimidazolate was employed as a linker (FIG. 36). The former gave a new structure (ZIF-23) of dia topology, but the latter lead again to the LTA structure (ZIF-22) with essentially identical atomic coordinates, both of which were identified by single crystal X-ray crystallography.

To produce the LTA structure it is necessary to have N atom at the position 5 of the linker. Indeed, careful examination of all these structures shows that a unique feature of the structure is (see especially FIG. 38d) that pairs of pairs of atoms of the six-membered ring at the positions 5 and 6 approach each other closely (3.39 and 3.52 Å). This appears to be caused by an electrostatic interaction and a dipole-dipole interaction between the CH—N . . . N—CH pair at the positions 5 and 6 of two linkers. In the case of 4-azabenzimidazolate, however, the distances between two linkers at positions 4 and 7 are too far to make a favorable interaction as may be seen from FIG. 38d. Such interactions favor forming the cube, presumably at an early stage in crystallization of the LTA structure. The importance of the initial formation of the cube has also been proposed for zeolite A LTA synthesis.

Once a cube is formed, the LTA structure is the primary topological candidate which can propagate. As has been discussed elsewhere, there are two ways of linking cubes through one kind of edge and these lead to the LTA and ACO topologies, so these are expected to be the default topologies. The LTA structure is already tailored to 145° T-X-T links (in this case X=Im), but in the maximum symmetry form of ACO that angle must be 180°. One can decrease the angle in an ACO-derived structure by lowering the symmetry, but, and this is a key point, to make an imidazolate ACO the T-Im bonds would have to be distorted significantly away from the plane of the linking molecule, in this case the five-membered $C_3H_1N_2$ imidazolate ring. In fact for imidazolates the T-Im bonds are coplanar with the imidazolate ring; for example, in ZIF-20 the Zn—N—N—Zn dihedral angles are 0.00-0.15° and the cubes can be linked with a 145° angle and a planar linker (FIG. 38e).

Figure 39:
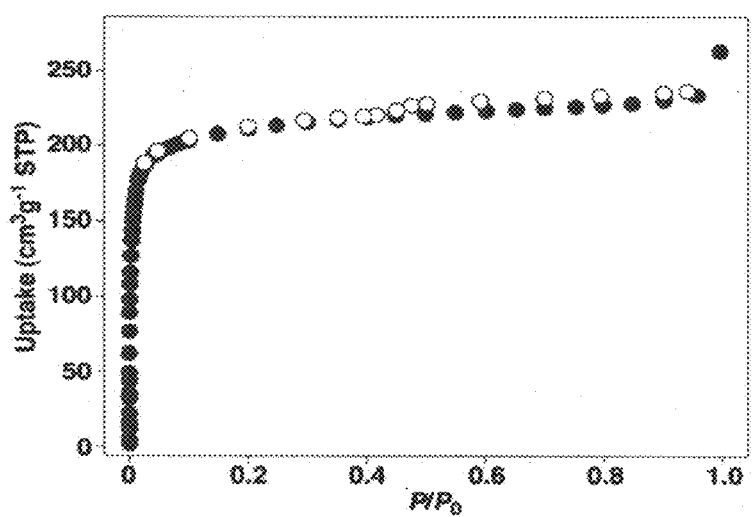
FIG. 39 shows argon adsorption measured at 87K for ZIF-20 showing type I behavior indicative of a permanently porous material, and a high surface area compared to zeolite A. Filled and open circles represent adsorption and desorption, respectively.
Figure 40:
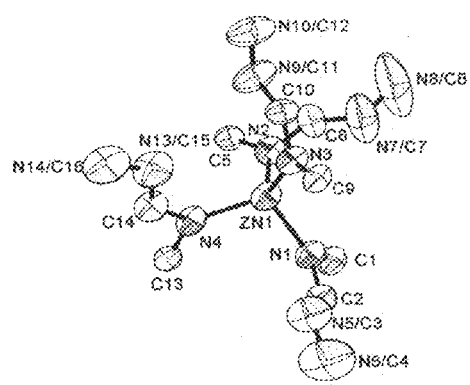
FIG. 40 shows ORTEP drawing of the asymmetric unit of ZIF-20, excluding the guest entities and hydrogen atoms are excluded also for clarity. Ellipsoids are displayed at the 50% probability level.
Figure 41:
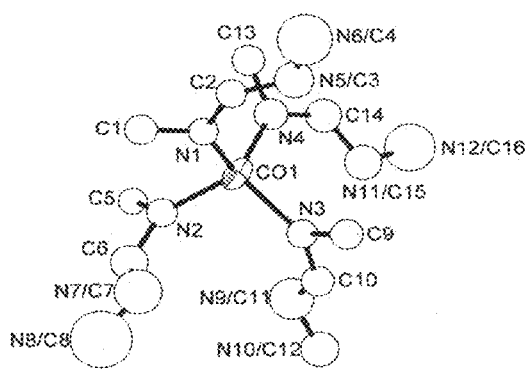
FIG. 41 shows ORTEP drawing of the asymmetric unit of ZIF-21, excluding the guest entities and hydrogen atoms are excluded also for clarity. Ellipsoids are displayed at the 50% probability level. Note that the organic purinate ligands have been refined isotropically.
Figure 42:
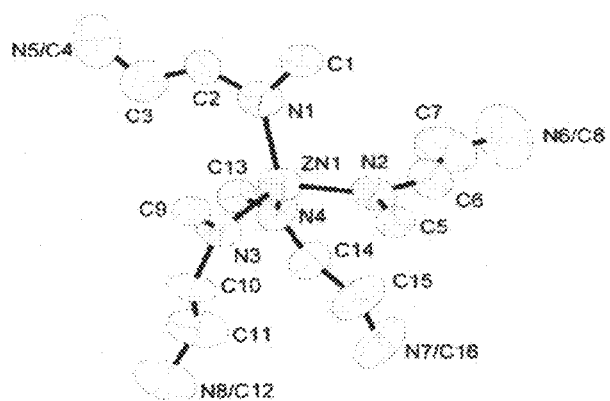
FIG. 42 shows ORTEP drawing of the asymmetric unit of ZIF-22, excluding the guest entities and hydrogen atoms are excluded also for clarity. Ellipsoids are displayed at the 50% probability level.
Figure 43:
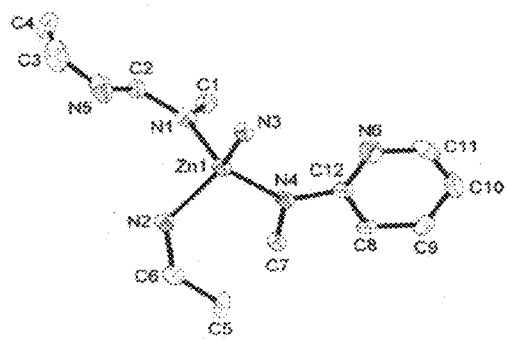
FIG. 43 shows ORTEP drawing of the asymmetric unit of ZIF-23, hydrogen atoms are excluded also for clarity. Ellipsoids are displayed at the 50% probability level.

The permanent porosity of guest-free (activated) ZIF-20 was proven by measurement of argon gas adsorption. As-synthesized ZIF-20 includes approximately 21 wt % of DMF and $H_2O$ estimated by an elemental analysis and a thermogravimetric analysis (TGA, FIG. 39). The activated sample was prepared by exchanging the solvent in as-synthesized ZIF-20 with methanol, followed by evacuation at room temperature. The methanol-exchanged and activated compounds were characterized by a TGA and powder X-ray diffraction (PXRD) measurement (see, FIGS. 48 and 44, respectively).

A type I isotherm (IUPAC classification) observed for Ar adsorption at 87 K (FIG. 39) indicates the microporosity of activated ZIF-20. The small $H_4$ hysteresis at $P/P_0 > 0.4$ can be attributed to intercrystalline voids in the sample. The maximum pore aperture (2.8 Å) of ZIF-20 determined from the crystal structure is smaller than the kinetic diameter of Ar (3.40 Å). However, the space inside the structure is accessible through a dynamic pore widening process wherein the Pur swing out of the way to allow gas molecules through. The apparent surface area and pore volume were calculated to be 800 m$^2$ g$^{-1}$ and 0.27 cm$^3$ g$^{-1}$ by applying the Langmuir and Dubinin-Radushkevitch (DR) equation, respectively.

The sample for the gas adsorption measurement was prepared as follows. The as-synthesized sample of ZIF-20 was immersed in anhydrous methanol in a glove box for 3 days; during the exchange the methanol was refreshed six times. The resulting methanol-exchanged sample of ZIF-20 in methanol was transferred to quartz cell in a glove box and the solvent was roughly decanted by pipette. The wet sample then was evacuated at ambient temperature for 12 hours to yield an activated sample (ca. 200 mg) for gas adsorption measurements. The sample cell with a filler rod was attached to a valve in a glove box, which was kept closed until the start of the measurement, and then attached to the instrument without exposing the sample to air.

Low-pressure Ar adsorption experiment (up to 1 atm) was performed on a Quantachrome AUTOSORB-1 automatic volumetric instrument at 87K using a liquid argon bath. Apparent surface areas of 800 m$^2$ g$^{-1}$ (Langmuir, the linearity of fitting, 0.999967) was obtained by using the data points on the adsorption branch in the range of P/P0=0.02-0.10. Micropore volume of 0.27 cm$^3$ g$^{-1}$ was obtained by applying the Dubinin-Radushkevitch (DR) equation (the linearity of fitting, 0.999781) in the range of P/P$_0$=0.02-0.10. Surface adsorption due to the quartz cell and filler rod was below 0.4% of the observed uptake with sample.

Data was collected on a Bruker SMART APEXII three circle diffractometer equipped with a CCD area detector and operated at 1200 W power (40 kV, 30 mA) to generate Cu Kα radiation (λ=1.5418 Å) radiation. The incident X-ray beam was focused and monochromated using Bruker Excalibur Gobel mirror optics. All crystals were mounted on nylon CryoLoops (Hampton Research) with Paraton-N (Hampton Research). Initial scans of each specimen were taken to gain preliminary unit cell parameters and to assess the mosaicity (i.e. breadth of spots between frames) of the crystal to select the required frame width for data collection. For all cases frame widths of 0.3° were judged to be appropriate and full hemispheres of data were collected using the Bruker APEX2$^1$ software suite to carry out overlapping Φ and ω scans at three different detector (2θ) settings (2θ=28, 60, 100°). Following data collection, reflections were sampled from all regions of the Ewald sphere to redetermine unit cell parameters for data integration and to check for rotational twinning using CELL_NOW. No evidence for crystal decay was ever encountered. Following exhaustive review of collected frames the resolution of the dataset was judged, and if necessary regions of the frames where no coherent scattering was observed were removed from consideration for data integration using the Bruker SAINTplus program. Data was integrated using a narrow frame algorithm and subsequently corrected for absorption. Space group determination and tests for merohedral twinning were carried out using XPREP. In all cases the highest possible space group was chosen and no indications of merohedral twinning observed.

Figure 44:
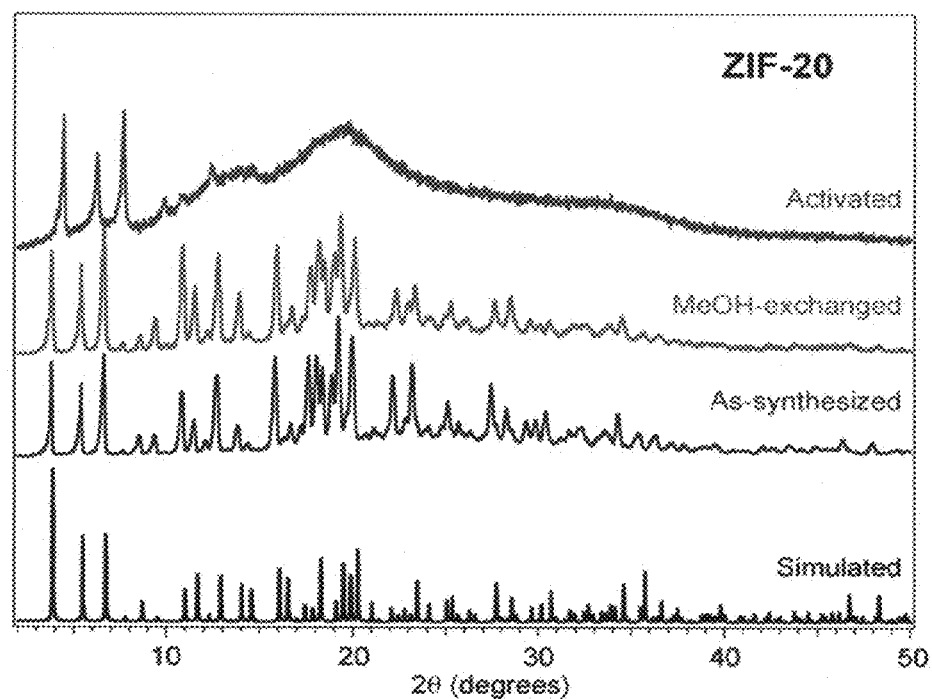
FIG. 44 shows a comparison of the experimental PXRD pattern of as-synthesized, MeOH-exchanged and activated ZIF-20 along with the simulated pattern from the single X-ray crystal structure.
Figure 45:
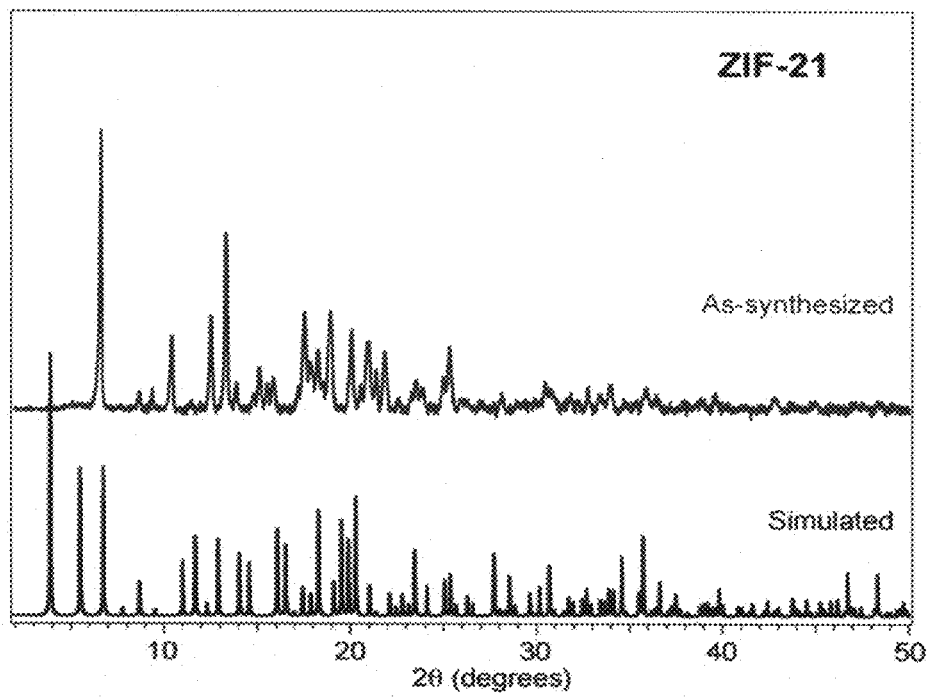
FIG. 45 shows a comparison of the experimental PXRD pattern of as-synthesized ZIF-21 along with the simulated pattern from the single X-ray crystal structure.
Figure 46:
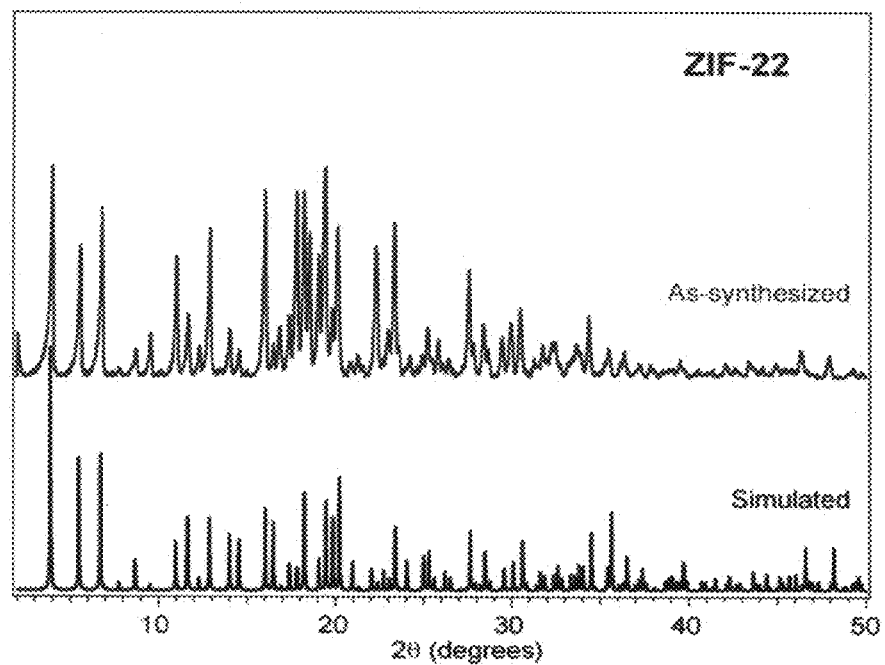
FIG. 46 shows a comparison of the experimental PXRD pattern of as-synthesized ZIF-22 along with the simulated pattern from the single X-ray crystal structure.
Figure 47:
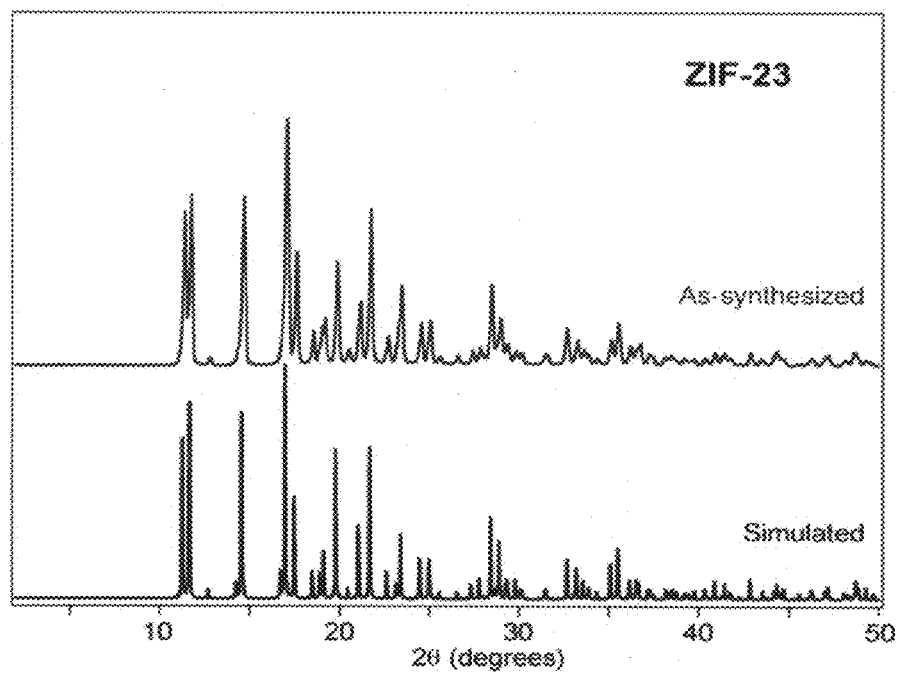
FIG. 47 shows a comparison of the experimental PXRD pattern of as synthesized ZIF-23 along with the simulated pattern from the single X-ray crystal structure.

The diffraction pattern collected for as-synthesized ZIFs are shown in FIG. 44-47 along with the simulated ones from their single X-ray crystal structures. The data for MeOH-exchanged and activated materials of ZIF-20 were also included as shown in FIG. 44.

Figure 48:
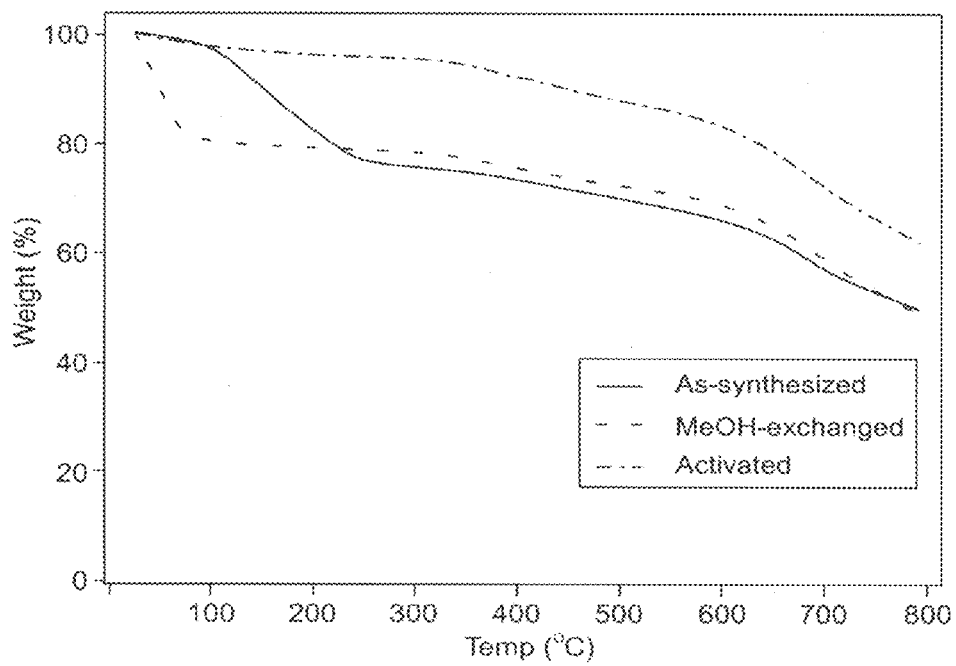
FIG. 48 is an overlay of TGA traces of as-synthesized, solvent-exchanged, and activated samples of ZIF-20.
Figure 49:
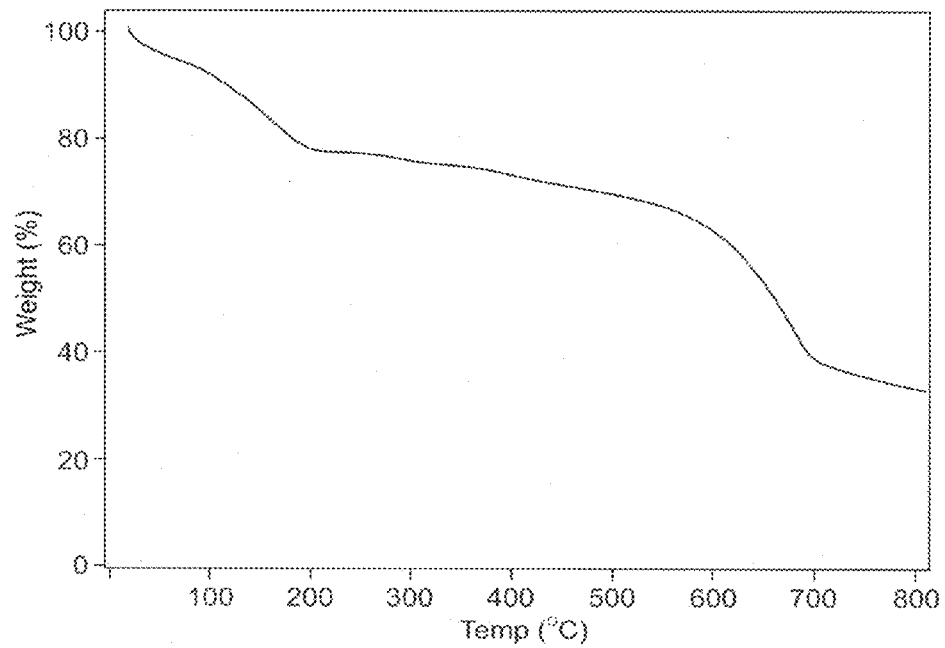
FIG. 49 shows a TGA trace of as-synthesized sample of ZIF-21.
Figure 50:
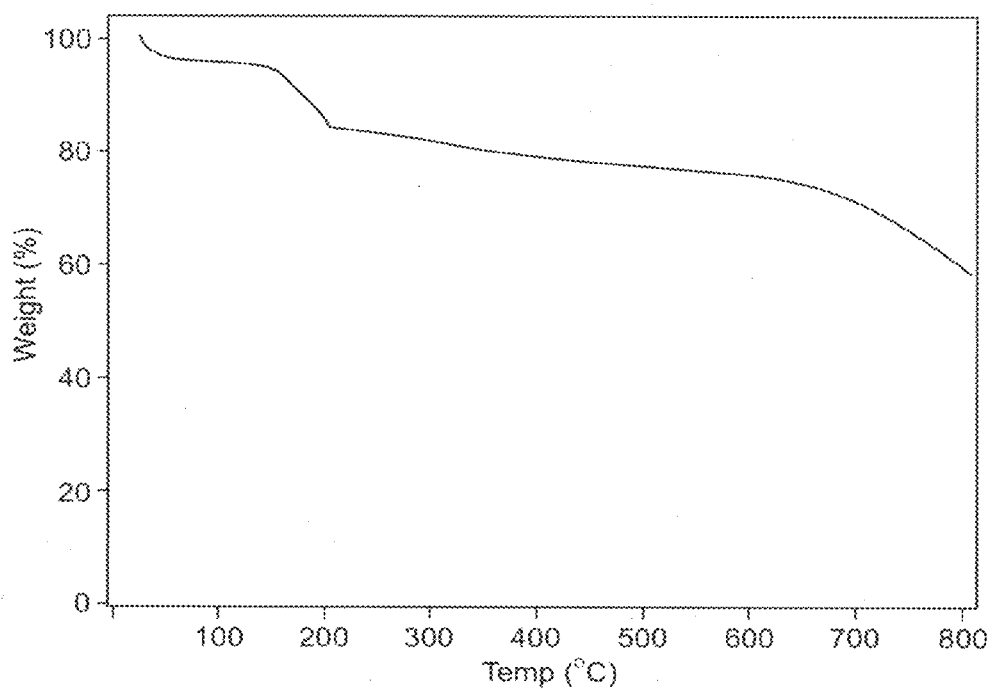
FIG. 50 shows a TGA trace of as-synthesized sample of ZIF-22.

The TGA traces of as-synthesized ZIF-20, -21, and -22 are shown in FIG. 48-50, respectively. The weight-loss of 23% up to 250° C. in ZIF-20 corresponds to the release of guest molecules (0.75 DMF and 1.5 H$_2$O; calcd. 21%), despite the fact that DMF is actually much larger than the aperture of ZIF-20 in size. The weight-loss of 23% up to 210° C. in ZIF-21 corresponds to the release of guest molecules (1 DMF and 1 H$_2$O; calcd. 23%). The weight-loss of 20% up to 250° C. in ZIF-22 corresponds to the release of guest molecules (0.75 DMF and 2 H$_2$O; calcd. 23%).

FIG. 48 also shows the TGA traces of a MeOH-exchanged and an activated ZIF-20. The original weight-loss up to 250° C. in as-synthesized material was replaced by an initial step of 20% around ambient temperature, indicative of the effective solvent-exchange by methanol. Although DMF molecule is actually much larger than the aperture of ZIF-20 in size, the solvent-exchange behavior can be explained by a dynamic structure of ZIF-20 as discussed for ZIF-11 in previous report. The profile for an activated material indicates that the solvent molecules captured in the pore were mostly removed, although slight weight-loss (~3%, probably due to H$_2$O) was observed.

Although a number of embodiments and features have been described above, it will be understood by those skilled in the art that modifications and variations of the described embodiments and features may be made without departing from the teachings of the disclosure or the scope of the invention as defined by the appended claims.

What is claimed is:

1. A framework, comprising a general structure:
M-L-M, wherein M comprises comprises zinc, L is a linking moiety and M-L-M has structure I:

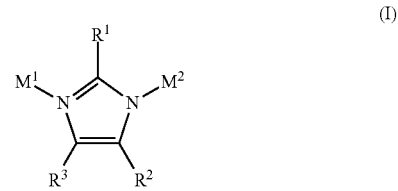

wherein R$^1$ is hydrogen,
R$^2$, R$^3$ are each individually hydrogen, an aryl, an alkyl, halo-, cyano-, or nitro-, and
M$^1$, M$^2$ are each independently zinc, the framework having a zeolitic topology selected from the group consisting of BCT, DFT, GIS, and MER.

2. The framework of claim 1, wherein L is selected from the group consisting of IV:

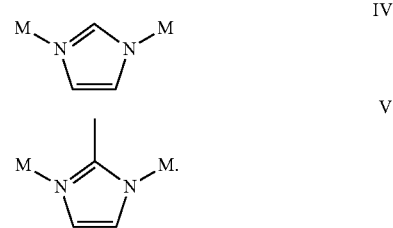

3. The framework of claim 1, wherein zinc increases cationic charge of the framework compared to a framework lacking zinc thereby increasing gas selectivity.

4. The framework of claim 1, wherein the framework comprises a plurality of pores, each of the plurality of pores having accessible sites for atomic or molecular adsorption.

5. The framework of claim 4, wherein a surface area of a surface defining a pore of the plurality of pores is greater than about 2000 m$^2$/g.

6. The framework of claim 4, wherein a surface area of a surface defining a pore of the plurality of pores is about 3,000-18,000 m$^2$/g.

7. The framework of claim 4, wherein a surface area of a surface defining a pore of the plurality of pores is about 3,000-6,000 m$^2$/g.

8. The framework of claim 4, wherein a surface defining a pore of the plurality of pores encloses a pore volume 0.1 to 0.99 cm$^3$/cm$^3$.

9. The framework of claim 4, wherein a surface defining a pore of the plurality of pores encloses a pore volume of 0.4-0.5 cm$^3$/cm$^3$.

10. The framework of claim 1, wherein the framework has a framework density of about 0.17 g/cm$^3$.

11. A gas storage device comprising the framework of claim 1.

12. A catalyst substrate comprising the framework of claim 1.

13. A framework, comprising a general structure:
M-L-M, wherein M comprises zinc, L is a linking moiety and M-L-M has structure I:

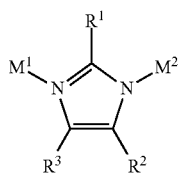
(I)

wherein R¹ is hydrogen,
R², R³ are each independently hydrogen or alkyl,
M¹, M² are each independently zinc, the framework having a zeolitic topology selected from the group consisting of BCT, DFT, GIS, and MER.

14. The framework of claim 13, wherein zinc increases cationic charge of the framework compared to a framework lacking zinc thereby increasing gas selectivity.

15. The framework of claim 13, wherein the framework comprises a plurality of pores, each of the plurality of pores having accessible sites for atomic or molecular adsorption.

16. The framework of claim 15, wherein a surface area of a surface defining a pore of the plurality of pores is greater than about 2000 m²/g.

17. The framework of claim 15, wherein a surface area of a surface defining a pore of the plurality of pores is about 3,000-18,000 m²/g.

18. The framework of claim 15, wherein a surface area of a surface defining a pore of the plurality of pores is about 3,000-6,000 m²/g.

19. The framework of claim 15, wherein a surface defining a pore of the plurality of pores encloses a pore volume of 0.1 to 0.99 cm³/cm³.

20. The framework of claim 15, wherein a surface defining a pore of the plurality of pores encloses a pore volume of 0.4-0.5 cm³/cm³.

21. The framework of claim 13, wherein the framework has a framework density of about 0.17 g/cm³.

22. The framework of claim 13, wherein R², R³ are each independently hydrogen or methyl.

23. The framework of claim 13, wherein R¹, R², R³ are each hydrogen.

24. The framework of claim 13, wherein R¹ is hydrogen and R², R³ are each alkyl.

25. The framework of claim 13, wherein R¹ is hydrogen and R², R³ are each methyl.

* * * * *

UNITED STATES PATENT AND TRADEMARK OFFICE
CERTIFICATE OF CORRECTION

PATENT NO. : 8,314,245 B2
APPLICATION NO. : 11/680386
DATED : November 20, 2012
INVENTOR(S) : Omar M. Yaghi et al.

It is certified that error appears in the above-identified patent and that said Letters Patent is hereby corrected as shown below:

Column 44, Line 35, Claim 2:

Delete formula V:

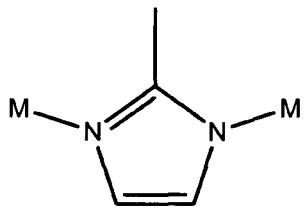

"       V       "

Signed and Sealed this
Twenty-sixth Day of February, 2013

Teresa Stanek Rea
*Acting Director of the United States Patent and Trademark Office*